(12) United States Patent
Markosyan

(10) Patent No.: US 9,562,064 B2
(45) Date of Patent: *Feb. 7, 2017

(54) HIGH-PURITY STEVIOL GLYCOSIDES

(71) Applicant: PureCircle Sdn Bhd, Kuala Lumpur (MY)

(72) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 14/603,941

(22) Filed: Jan. 23, 2015

(65) Prior Publication Data

US 2015/0141632 A1    May 21, 2015

Related U.S. Application Data

(63) Continuation of application No. 13/580,098, filed as application No. PCT/US2011/028028 on Mar. 11, 2011, now Pat. No. 8,981,081.

(60) Provisional application No. 61/313,375, filed on Mar. 12, 2010, provisional application No. 61/313,388, filed on Mar. 12, 2010, provisional application No. 61/373,491, filed on Aug. 13, 2010, provisional application No. 61/385,215, filed on Sep. 22, 2010.

(51) Int. Cl.

| | | |
|---|---|---|
| C07H 1/08 | (2006.01) | |
| B01D 15/18 | (2006.01) | |
| A61K 8/60 | (2006.01) | |
| A23L 1/236 | (2006.01) | |
| A61K 31/7034 | (2006.01) | |
| A61Q 11/00 | (2006.01) | |
| C07H 1/06 | (2006.01) | |
| A61K 31/704 | (2006.01) | |
| A61K 36/28 | (2006.01) | |
| A21D 2/18 | (2006.01) | |
| A23C 9/13 | (2006.01) | |
| A23G 1/40 | (2006.01) | |
| A23G 3/42 | (2006.01) | |
| A23G 9/34 | (2006.01) | |
| A23L 2/02 | (2006.01) | |
| A23L 2/60 | (2006.01) | |

(52) U.S. Cl.
CPC .............. *C07H 1/08* (2013.01); *A23L 27/36* (2016.08); *A61K 8/602* (2013.01); *A61K 31/704* (2013.01); *A61K 31/7034* (2013.01); *A61K 36/28* (2013.01); *A61Q 11/00* (2013.01); *B01D 15/1871* (2013.01); *C07H 1/06* (2013.01); *A21D 2/181* (2013.01); *A23C 9/1307* (2013.01); *A23G 1/40* (2013.01); *A23G 3/42* (2013.01); *A23G 9/34* (2013.01); *A23L 2/02* (2013.01); *A23L 2/60* (2013.01); *A23L 27/50* (2016.08); *A61K 2236/00* (2013.01)

(58) Field of Classification Search
None
See application file for complete search history.

(56) References Cited

U.S. PATENT DOCUMENTS

| | | | | |
|---|---|---|---|---|
| 5,962,678 A | * | 10/1999 | Payzant | A23L 1/2366 536/127 |
| 8,891,081 B1 | * | 11/2014 | Chen | G01N 21/65 356/301 |
| 2007/0082103 A1 | * | 4/2007 | Magomet | A23C 9/1307 426/548 |

FOREIGN PATENT DOCUMENTS

IN    WO 2006038221 A1 * 4/2006    ......... C07N 15/256

* cited by examiner

*Primary Examiner* — Frederick Krass
*Assistant Examiner* — Michael P Cohen
(74) *Attorney, Agent, or Firm* — Briggs and Morgan, P.A.; Audrey J. Babcock

(57) ABSTRACT

Methods of preparing highly purified steviol glycosides, particularly Rebaudioside D, are described. The methods include purification from the extraction stage of the *Stevia rebaudiana* Bertoni plant, purification of steviol glycoside mixtures, Rebaudioside D and Rebaudioside A from a commercial *Stevia* extract, and purification of Rebaudioside D from remaining solutions obtained after isolation and purification of Rebaudioside A and a high purity mixture of steviol glycosides. The methods are useful for producing high purity Rebaudioside D, Rebaudioside A, and steviol glycoside mixtures. The high purity steviol glycosides are useful as non-caloric sweeteners in edible and chewable compositions such as any beverages, confectioneries, bakery products, cookies, and chewing gums.

7 Claims, 17 Drawing Sheets

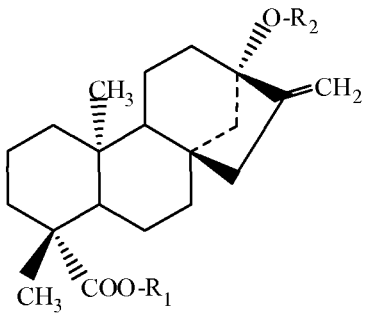

| Compound name | $R_1$ (C-19) | $R_2$ (C-13) |
| --- | --- | --- |
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1)<br>   |<br>β-Glc(3→1) |
| 7. Rebaudioside B | H | β-Glc-β-Glc(2→1)<br>   |<br>β-Glc(3→1) |
| 8. Rebaudioside C (Dulcoside B) | β-Glc | β-Glc-α-Rha(2→1)<br>   |<br>β-Glc(3→1) |
| 9. Rebaudioside D | β-Glc-β-Glc(2→1) | β-Glc-β-Glc(2→1)<br>   |<br>β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1)<br>   |<br>β-Glc(3→1) |
| 12. Dulcoside A | β-Glc | β-Glc-α-Rha(2→1) |

FIG. 1

Steviol

Stevioside

Rebaudioside A

Rebaudioside B

Rebaudioside C

Rebaudioside D

Rebaudioside E

Rebaudioside F

Dulcoside A

Steviolbioside

Rubusoside

HIGH-PURITY STEVIOL GLYCOSIDES

RELATED APPLICATIONS

This application is a continuation of, and claims the benefit of priority to, U.S. application Ser. No. 13/580,098, filed on Nov. 6, 2012, which is a U.S. National Phase application under 35 USC 371 of PCT Application Number PCT/US2011/028028 filed on Mar. 11, 2011, which claims the benefit of U.S. Provisional Patent Application No. 61/313,375, filed on Mar. 12, 2010, U.S. Provisional Patent Application No. 61/313,388, filed on Mar. 12, 2010, U.S. Provisional Patent Application No. 61/373,491, filed on Aug. 13, 2010, and U.S. Provisional Patent Application No. 61/385,215, filed on Sep. 22, 2010, the contents of which applications are incorporated herein by reference in their entireties.

TECHNICAL FIELD

The present invention relates to a process for the treatment of various steviol glycoside sources in order to isolate purified sweet glycosides, either as a mixture or as individual steviol glycosides such as Rebaudioside A or Rebaudioside D.

BACKGROUND OF THE INVENTION

High intensity sweeteners possess a sweetness level that is many times greater than the sweetness level of sucrose. They are essentially non-caloric and are used widely in the manufacturing of diet and reduced calorie food. Although natural caloric sweetener compositions, such as sucrose, fructose, and glucose, provide a desirable taste to consumers, they have a caloric content. High intensity sweeteners, being essentially non-caloric, do not affect the blood glucose level and provide little or no nutritive value.

However, the high intensity sweeteners generally used as sugar (sucrose) substitutes possess taste characteristics different from those of sugar. The taste characteristics that differ from those of sugar may include the temporal profile of the sweet taste, maximal response, flavor profile, mouthfeel, and adaptation behavior. For example, the sweet taste of some high-potency sweeteners are slower in onset and longer in duration than the sweet taste produced by sugar and thus change the taste balance of a food composition. Because of these differences, the use of high-potency sweeteners to replace a bulk sweetener such as sugar, in a food or beverage, may cause an imbalance in the temporal and/or flavor profile. If the taste profile of high-potency sweeteners could be modified to impart desired taste characteristics, high-potency sweeteners could be used to provide more desirable taste characteristics to low calorie beverages and food products.

On the other hand, high-potency sweeteners may have some cost and functional advantages compared to sugar. There is significant competition among sugar and non-sugar sweeteners in the soft drink industry, in countries where the use and production of high-potency sweeteners is permitted, and in countries with overvalued sugar prices.

At present high intensity sweeteners are used worldwide. They can be both synthetic and natural origin.

Examples of synthetic sweeteners include, but are not limited to, sucralose, potassium acesulfame, aspartame, alitame, saccharin, neohesperidin dihydrochalcone, cyclamate, neotame, dulcin, suosan, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L- phenylalanine 1-methyl ester, N—[N-[3-(3-methoxy-4-hydroxyphenyl)propyl]-L-α-aspartyl]-L-phenylalanine 1-methyl ester, salts thereof, and the like.

Examples of natural high intensity sweeteners include, but are not limited to, Stevioside, Rebaudioside A, Rebaudioside B, Rebaudioside C, Rebaudioside E, Rebaudioside F, Steviolbioside, Dulcoside A, Rubusoside, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, and siamenoside.

High intensity sweeteners can be derived from the modification of natural high intensity sweeteners by, for example, fermentation, contact with enzymes, or derivatization.

At present about twelve high intensity sweeteners are used worldwide. These are acesulfame-K, alitame, aspartame, cyclamate, glycyrrhizin, neohesperidin dihydrochalcone (NHDC), saccharin, Stevioside, sucralose, thaumatin, neotame, and Rebaudioside A.

The high intensity sweeteners can be grouped into a few different generations. The first generation, represented by cyclamate, glycyrrhizin and saccharin, has a long history of use in food. The second generation includes acesulfame-K, aspartame, NHDC and thaumatin. Alitame, neotame, sucralose, Stevioside, and Rebaudioside A belong to the third generation.

The standard sweetening power associated with each high intensity sweetener is given in TABLE 1. However, when they are used in blends, the sweetening power can change significantly.

TABLE 1

| Sweetener | Sweetness power |
| --- | --- |
| Saccharose (sucrose) | 1 |
| Acesulfame-K | 200 |
| Alitame | 2000 |
| Aspartame | 200 |
| Cyclamate | 30 |
| Glycyrrhizin | 50 |
| NHDC | 1000 |
| Saccharin | 300 |
| Stevioside | 200 |
| Rebaudioside A | 450 |
| Thaumatin | 3000 |
| Sucralose | 600 |

"Natural" and "organic" foods and beverages have become the "hottest area" in the food industry. The combination of consumers' desire, advances in food technology, and new studies linking diet to disease and disease prevention have created an unprecedented opportunity to address public health through diet and lifestyle.

A growing number of consumers perceive the ability to control their health by enhancing their current health and/or hedging against future diseases. This creates a demand for food products with enhanced characteristics and associated health benefits, and creates a food and consumer market trend towards a "whole health solutions" lifestyle. The term "natural" is highly emotive in the world of sweeteners and has been identified as a term that is highly trusted by consumers, along with "whole grain", "heart-healthy" and "low-sodium". Among many consumers, the term "natural" is closely related to "healthier". In this respect, natural high intensity sweeteners can have better commercial potential than artificial sweeteners.

Stevia rebaudiana Bertoni is a perennial shrub of the Asteraceae (Compositae) family native to certain regions of South America. The leaves of the plant contain diterpene glycosides in an amount ranging from about 10 to 20%. These diterpene glycosides are about 150 to 450 times sweeter than sugar. The leaves of the Stevia rebaudiana Bertoni plant have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia, and Paraguay.

At present more than 230 Stevia species have been discovered, including one Stevia species that has significant sweetening properties. The plant has been successfully grown under a wide range of conditions from its native subtropics to the cold northern latitudes.

The extract of the Stevia rebaudiana plant contains a mixture of different sweet diterpene glycosides which have a single base, steviol, and differ by the presence of carbohydrate residues at positions C13 and C19. These glycosides accumulate in Stevia leaves and compose approximately 10%-20% of the total dry weight. Typically, on a dry weight basis, the four major glycosides found in the leaves of Stevia are Dulcoside A (0.3%), Rebaudioside C (0.6-1.0%), Rebaudioside A (3.8%) and Stevioside (9.1%). Other glycosides identified in Stevia extract include Rebaudioside B, C, D, E, and F, Steviolbioside and Rubusoside. Among steviol glycosides only Stevioside and Rebaudioside A are available on a commercial scale.

Steviol glycosides have zero calories and can be used wherever sugar is used. They are ideal for diabetic and low calorie diets. In addition, the sweet steviol glycosides possess functional and sensory properties superior to those of many high potency sweeteners.

The chemical structures of the diterpene glycosides of Stevia rebaudiana Bertoni are presented in FIGS. 2a-2k.

The physical and sensory properties of steviol glycosides are well studied only for Stevioside and Rebaudioside A. Stevioside is about 210 times sweeter than sucrose, and Rebaudioside A is between 200 and 400 times sweeter than sucrose. Rebaudioside A is considered to have the most favorable sensory attributes of the four major steviol glycosides.

Amongst the sweet diterpenoid glycosides of Stevia, Rebaudioside D has been identified as the least bitter, and with the least persistent aftertaste. Impurities can significantly increase the bitterness of diterpenoid glycosides.

The glycosides can be extracted from leaves using either water or organic solvent extraction. Supercritical fluid extraction and steam distillation methods have also been described. Methods for the recovery of diterpene sweet glycosides from Stevia rebaudiana using supercritical $CO_2$, membrane technology, and water or organic solvents, such as methanol and ethanol, may also be used.

Generally the production of an extract includes extraction of plant material with water or a water-organic solvent mixture, precipitation of high molecular weight substances, deionization, and decolorization, purification on specific macroporous polymeric adsorbents, concentration and drying.

All of the existing methods for the recovery of steviol glycosides involve the isolation and purification of a steviol glycoside from the initial plant extract, and do not include a method for the further treatment of residual solutions or the purification of minor compounds. Thus, there is a need for an efficient and economical method for the comprehensive retreatment of extract produced from the Stevia rebaudiana Bertoni plant.

Due to regulatory requirements, only materials containing more than 95% total steviol glycosides are allowed to be used as sweeteners for human consumption. The majority of commercially available Stevia rebaudiana raw extracts contain 80-90% total steviol glycosides. Hence further purification is necessary to obtain highly purified products with more than 95% total steviol glycoside content. Therefore, there is a need for a commercially viable process for enhancing steviol glycoside content in low purity steviol glycoside preparations, to the levels which allow their usage in food.

Among sweet glycosides existing in Stevia rebaudiana, only Stevioside and Rebaudioside A are available at moderate cost at <80% purity and at high cost at >80% purity. There are no commercial quantities of Rebaudiosides B, D, E, F and C available in the market.

Rebaudioside D (CAS No: 63279-13-0) is one of the sweet glycosides found in Stevia rebaudiana. Its isolation and purification is a very challenging task due to its low content in Stevia leaves. The average Rebaudioside D content in dry leaves ranges from about 0.01-0.20%. Moreover, many analytical techniques often fail to detect Rebaudioside D in Stevia leaves or steviol glycoside preparations, due to its low content.

Only recently have highly purified Rebaudioside D reference materials become available on the market. Due to the high cost of the purification techniques employed, the price of such materials makes it impractical to use them in any area other than analytical chemistry.

However, studies show that highly purified forms of Rebaudioside D possess a very desirable taste profile, almost lacking in bitterness and in the lingering licorice aftertaste typical for other steviol glycosides. These properties multiply the significance of Rebaudioside D and attract great interest for methods of preparation of highly purified forms of Rebaudioside D.

The methods of Rebaudioside D preparation described in the literature employ costly chromatographic techniques which are only applicable for laboratory or pilot scale production. There is no published data on the commercial isolation and purification of Rebaudioside D.

Sakamoto et al. describe a process of isolation of rebaudioside D from the glycosidic fraction of Stevia leave methanolic extract prepared according to Kohda et al. Sakamoto I., Yamasaki Tanaka O. (1977), "Application of $^{13}C$ NMR Spectroscopy to Chemistry of Natural Glycosides: Rebaudioside-C, a New Sweet Diterpene Glycoside of Stevia rebaudiana." Chem. Pharm. Bull., 25(4), p. 844; Kohda H., Kasai R., Yamasaki K., Murakami K., Tanaka O. (1976), "New sweet diterpene glucosides from Stevia rebaudiana." Phytochemisty, 15, p. 981. The process comprises recrystallization of a glycosidic fraction from methanol and further chromatography on silica gel. The described process employs solvent extraction and chromatographic techniques which are useful in laboratory and pilot scale, but have limited scale-up potential due to the high cost of the process and toxicity of the extraction solvents.

Hence, there is a need for a simple, efficient, and economical method for the production of high purity Rebaudioside D.

There is also a need for a commercially viable process for enhancing steviol glycoside content in low purity steviol glycoside preparations to the levels which allow their usage in food.

Any technological scheme which can effect the purification of a mixture of low purity steviol glycosides, into a mixture of highly purified steviol glycosides and highly purified Rebaudioside D, will have a certain advantage over the techniques currently known in the art.

SUMMARY OF THE INVENTION

The present invention provides a method for the preparation of highly purified mixtures of steviol glycosides, or individual glycosides, from low purity steviol glycoside mixtures, from *Stevia* extracts, and from the *Stevia rebaudiana* Bertoni plant, and the products resulting from the method.

An object of the invention is to provide an efficient method for isolating and purifying different steviol glycosides, particularly Rebaudioside D, from various mixtures of steviol glycosides, from *Stevia* extracts, and from the *Stevia rebaudiana* Bertoni plant, and a high purity Rebaudioside D resulting from this method.

The present invention is directed to a method for purifying steviol glycosides, which includes passing a solution of steviol glycosides through a multi-column system including a plurality of columns packed with an adsorbent resin, to obtain at least one column having adsorbed steviol glycosides. The method further includes removing impurities from the multi-column system. The adsorbed steviol glycosides are then eluted from the column or columns having adsorbed steviol glycosides, to obtain an eluted solution of steviol glycosides. The eluted solution of steviol glycosides may then be dried to obtain a purified mixture of steviol glycosides.

The present invention is also directed to a method for purifying Rebaudioside D, which includes passing a solution of steviol glycosides through a multi-column system including a plurality of columns packed with an adsorbent resin, to obtain at least one column having adsorbed steviol glycosides. The method further includes removing impurities from the multi-column system. Fractions with a high Rebaudioside D content are then eluted with an aqueous alcohol solution. Rebaudioside D may be further purified by mixing the high Rebaudioside D fractions with a first aqueous alcohol solution to obtain a Rebaudioside D solution, inducing crystallization to obtain first crystals of Rebaudioside D, and separating the first crystals of Rebaudioside D from the Rebaudioside D solution, wherein the first crystals have a purity level greater than about 60% (w/w) on a dry basis. The first crystals may then be suspended in a second aqueous alcohol solution, to obtain second crystals of Rebaudioside D and a third aqueous alcohol solution. The second crystals of Rebaudioside D may be separated from the third aqueous alcohol solution. These second crystals may have a purity level greater than about 95% (w/w) on a dry basis.

In accordance with the present invention, the solution of steviol glycosides which is passed through a multi-column system may be prepared from a biomass of the *Stevia rebaudiana* Bertoni plant. To obtain a solution of steviol glycosides from a biomass of the *Stevia rebaudiana* Bertoni plant, a crude extract may be produced by contacting the biomass with water, separating insoluble material from the crude extract to obtain a filtrate containing steviol glycosides, and treating the filtrate to remove high molecular weight compounds and insoluble particles to obtain the solution of steviol glycosides.

The solution of steviol glycosides prepared from a biomass of the *Stevia rebaudiana* Bertoni plant may be passed through a multi-column system including a plurality of columns packed with an adsorbent resin, to obtain at least one column having adsorbed steviol glycosides. Impurities may be removed from the multi-column system by eluting the multi-column system with a washing solution. The adsorbed steviol glycosides are then eluted from the column or columns having adsorbed steviol glycosides, to obtain an eluted solution of steviol glycosides. The eluted solution of steviol glycosides may be further purified, using a method including treating the eluted solution to obtain a decolorized solution, evaporating the solvent from the decolorized solution to obtain a first adsorption solution, passing the first adsorption solution through a column with a macroporous adsorbent to obtain a second adsorption solution, deionizing and concentrating the second adsorption solution, and drying the deionized and concentrated second adsorption solution to obtain a purified steviol glycoside mixture with at least about 95% by weight total steviol glycosides.

Purified steviol glycoside mixtures and purified individual steviol glycosides, prepared in accordance with the present invention, may be used in a variety of products including, but not limited to, foods, beverages, pharmaceutical compositions, tobacco products, nutraceutical compositions, oral hygiene compositions, and cosmetic compositions.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 1 shows the structure of steviol glycosides in the *Stevia rebaudiana* Bertoni leaves.

DETAILED DESCRIPTION OF THE INVENTION

Figure 2A:
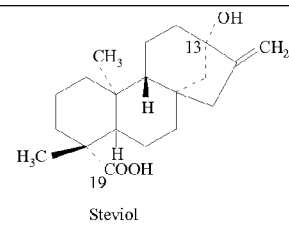
FIGS. 2*a*-2*k* show the chemical structures of *Stevia rebaudiana* Bertoni glycosides.
Figure 2B:
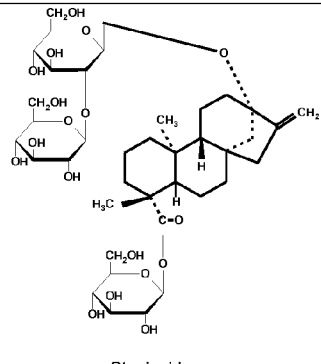
Figure 2C:
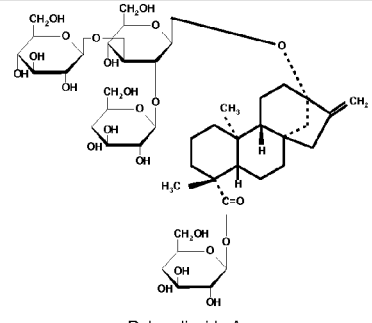
Figure 2D:
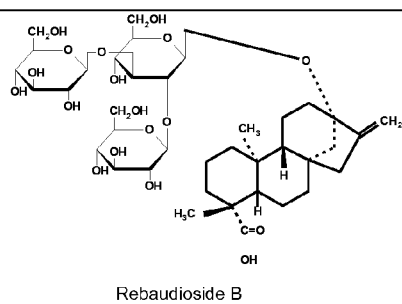
Figure 2E:
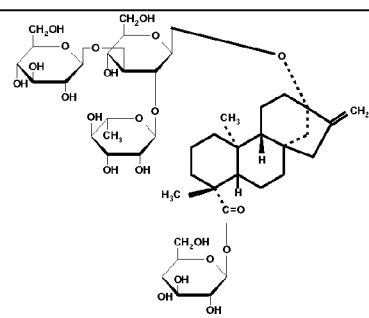
Figure 2F:
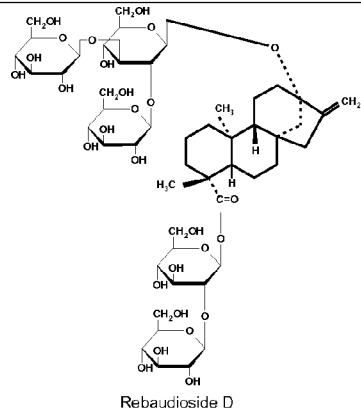
Figure 2G:
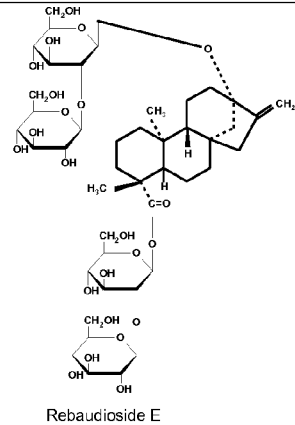
Figure 2H:
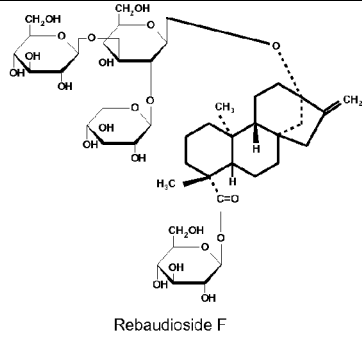
Figure 2I:
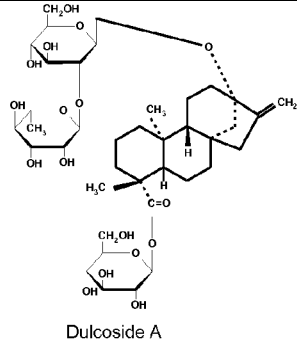
Figure 2J:
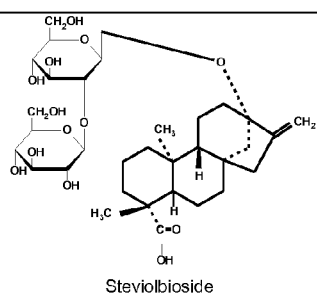
Figure 2K:
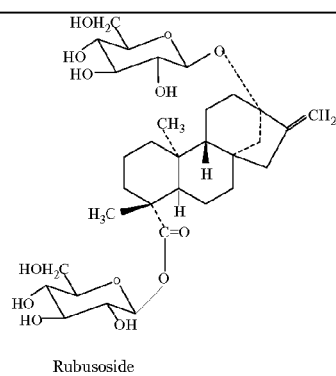

The present invention provides a method for the production of highly purified mixtures of steviol glycosides and of highly purified individual steviol glycosides, such as Rebaudioside D, by various schemes.

The production scheme and priority of the steps can be changed depending on the main goal of the process and the desired business and technological model.

Highly purified steviol glycoside mixtures or individual steviol glycosides, alone or in combination with other sweeteners and/or other ingredients, are useful as non-caloric sweeteners in edible and chewable compositions, such as any beverages, confectioneries, bakery products, cookies, chewing gums, oral hygiene compositions, and the like.

Hereinafter the term "steviol glycoside(s)" will mean Rebaudioside A, Rebaudioside B, Rebaudioside C, Rebaudioside D, Rebaudioside E, Rebaudioside F, Stevioside, Steviolbioside, Dulcoside A, Rubusoside, or other glycosides of steviol and combinations thereof.

Hereinafter the term "TSG content" will mean Total Steviol Glycosides content, and it will be calculated as the sum of the content of all steviol glycosides on a dry basis, including Rebaudioside A, Rebaudioside B, Rebaudioside C, Rebaudioside D, Rebaudioside E, Rebaudioside F, Stevioside, Steviolbioside, Dulcoside A and Rubusoside.

Hereinafter the term "highly purified" or "high purity" will mean a steviol glycoside purity and/or TSG level of at least 95% (w/w) on a dry basis.

Hereinafter the term "low purity" will mean a steviol glycoside purity and/or TSG level of less than 95% (w/w) on a dry basis.

Hereinafter the terms "Reb A", "Reb B", "Reb C", "Reb E", and "Reb F" refer to Rebaudiosides A, B, C, E, and F.

Hereinafter the term "Reb D" refers to Rebaudioside D (CAS No. 63279-13-0).

Hereinafter the term "impurity" will mean any compound other than steviol glycosides which are present in the mixture at more than 0.0001% (w/w) on a dry basis. Examples of impurities include, but are not limited to, typical plant materials, such as pigments and saccharides, phenolic compounds, volatile oil components, sterols, triterpenes, flavonoids, coumarins, non-glycosidic diterpenes (sterebins) spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, and pentacyclic triterpene.

In one embodiment of this invention a column system with the following parameters was used. A system of consecutive (serial) or parallel connected columns, of the same or different volumes, packed with a sorbent with different affinities to impurities and steviol glycosides. When the system is used in parallel connection mode, the inlet of each column may connect to a separate feed source while the outlet of each column connects to a separate receiver. The following description will highlight the mode of column connection specific to each particular case. Within the same stage the system may function as an entity of several parallel and serial connected column groups and separate columns. The number of columns may be 3-15. The ratio of the volume of the first column to the volume of the second column is preferably in the range of about 1:1 to 1:10. The ratio of the volume of the last column to the volume of the previous, or penultimate, column is preferably in the range of about 3:1 to 1:10. The columns may be packed with sorbent up to about 75-100% of their total volume. The columns may be maintained at a temperature in the range of about 5-80° C., and preferably in the range of about 15-25° C.

The alcohols employed in the invention may be selected from the group consisting of alkanols, and are preferably selected from the group including methanol, ethanol, n-propanol, 2-propanol, 1-butanol, and 2-butanol.

The sorbents may be any macroporous polymeric adsorption resins capable of adsorbing steviol glycosides, such as the Amberlite® XAD series (Rohm and Haas), Diaion® HP series (Mitsubishi Chemical Corp), Sepabeads® SP series (Mitsubishi Chemical Corp), Cangzhou Yuanwei YWD series (Cangzhou Yuanwei Chemical Co. Ltd., China), or the equivalent.

In one embodiment of the present invention, an aqueous or aqueous alcoholic solution of a low purity steviol glycoside mixture was passed through the consecutively connected column system. If an aqueous alcoholic solution is used, the water to alcohol ratio (vol/vol) in the aqueous alcoholic solution may be in the range of about 99.9:0.1 to 60:40. As a result impurities and different steviol glycosides are retained in different sections of the column system. Impurities with higher affinities to the sorbent are retained in the first column, impurities with lower affinities to the sorbent are retained in the last column, and different steviol glycosides are retained in different sections of the system at different concentrations, depending on their affinities to the sorbent. As a result, an initial mixture of low purity steviol glycosides separates into different portions retained on different columns. The portions differ from each other both by TSG and individual glycoside (particularly Reb D) content.

In another embodiment of the present invention, columns with retained steviol glycosides are subjected to elution of residual impurities in order to increase further the purity level of the final products. Columns are subsequently eluted with an aqueous or aqueous alcoholic solution of an acid, an aqueous or aqueous alcoholic solution of a base, and an aqueous alcoholic solution, in a specific order. The water to alcohol ratio (vol/vol) in the aqueous alcoholic solution is in the range of about 99.9:0.1 to 60:40. The elution of impurities is carried out either from each column separately (parallel connection) or from two or more consecutively (serially) connected columns.

Another embodiment of the present invention comprises the elution of columns with an aqueous alcoholic solution in which the water to alcohol ratio (vol/vol) is in the range of about 60:40 to 0.1:99.9. The elution is carried out either from each column separately (parallel connection) or from two or more consecutively (serially) connected columns.

One embodiment of the present invention utilizes centrifugation techniques to separate crystals or other suspended solids from a liquid. However any other type of equipment which separates a precipitate from a liquid, such as various types of centrifuges or filtration systems, can be used as well.

Another embodiment utilizes a rotary vacuum dryer to dry separated crystals and/or solids. However different type of dryers such as fluid bed dryers, rotary tunnel dryers, or plate dryers are suitable as well.

Exemplary embodiments of this invention are described in detail below and illustrated in FIGS. 4-16.

Purification of Steviol Glycosides from a Low Purity Steviol Glycosides Mixture

The present invention is directed to a method for preparing a purified steviol glycoside mixture from a steviol glycoside mixture of lower purity, including the steps of providing a steviol glycoside mixture, dissolving the steviol glycosides mixture in a solvent to produce a solution of steviol glycosides, passing the solution of steviol glycosides through a multi-column system including a plurality of columns packed with an adsorbent resin, eluting impurities from the multi-column system with water or an aqueous solution, eluting steviol glycoside mixture fractions from the multi-column system with an aqueous alcohol solution, and drying the steviol glycoside mixture fractions to obtain the purified steviol glycoside mixture.

According to the present invention the purification of steviol glycosides was developed from a steviol glycosides mixture with a TSG content of less than 95% w/w on a dry basis.

In one example, the TSG content of a "low purity" initial mixture was 85.29% (w/w on a dry basis), comprising 0.16% Rubusoside, 0.68% Dulcoside A, 26.20% Stevioside, 9.78% Rebaudioside C, 1.86% Rebaudioside F, 45.92% Rebaudioside A, 0.51% Rebaudioside D, 0.09% Steviolbioside, and 0.09% Rebaudioside B.

A column system as described above was used to purify the "low purity" initial mixture of steviol glycosides in a four-stage process, which is discussed below.

The first stage of purification of the steviol glycoside mixture comprises passing an aqueous or aqueous alcoholic solution of a low purity steviol glycoside mixture through the consecutively connected column system. The water to alcohol ratio (vol/vol) in the aqueous alcoholic solution is in the range of 99.9:0.1 to 60:40. As a result, impurities and different steviol glycosides are retained in different sections of the column system. Impurities with higher affinities to the sorbent are retained in the first column, impurities with lower affinities to the sorbent are retained in the last column, and different steviol glycosides are retained in different sections of the system at different concentrations, depending on their affinities to sorbent. The steviol glycosides are mostly retained in the middle section of the system.

In one example, the total elution of the middle section columns after the first stage resulted in a steviol glycoside mixture with a TSG content of 91.14% (w/w on a dry basis) comprising 0.17% Rubusoside, 0.72% Dulcoside A, 28.05% Stevioside, 10.43% Rebaudioside C, 1.98% Rebaudioside F, 49.07% Rebaudioside A, 0.54% Rebaudioside D, 0.09% Steviolbioside, and 0.09% Rebaudioside B.

In the second stage of purification, the middle section columns with retained steviol glycosides are subjected to elution of residual impurities which still remain after the first stage of separation, in order to increase further the purity level of the final products. Columns are subsequently eluted with an aqueous or aqueous alcoholic solution of an acid, an aqueous or aqueous alcoholic solution of a base, and an aqueous alcoholic solution, in a specific order. The water to alcohol ratio (vol/vol) in the aqueous alcoholic solution is in the range of about 99.9:0.1 to 60:40. Elution of impurities is carried out either from each column separately (parallel connection) or from two or more consecutively (serially) connected columns.

In one example, the total elution of middle section columns after the second stage resulted in a steviol glycoside mixture with a TSG content of 98.05% (w/w on a dry basis) comprising 0.18% Rubusoside, 0.78% Dulcoside A, 30.16% Stevioside, 11.25% Rebaudioside C, 2.14% Rebaudioside F, 52.77% Rebaudioside A, 0.59% Rebaudioside D, 0.09% Steviolbioside, and 0.09% Rebaudioside B.

The third stage of purification comprises elution of middle section columns with an aqueous alcoholic solution in which the water to alcohol ratio (vol/vol) is in the range of about 60:40 to 0.1:99.9. The elution is carried out either from each column separately (parallel connection) or or from two or more consecutively (serially) connected columns.

In one example, the elution of middle section columns at the third stage resulted in a steviol glycoside mixture with a TSG content of 98.56% (w/w on a dry basis) comprising 0.18% Rubusoside, 0.78% Dulcoside A, 30.31% Stevioside, 11.31% Rebaudioside C, 2.15% Rebaudioside F, 53.04% Rebaudioside A, 0.59% Rebaudioside D, 0.10% Steviolbioside, and 0.10% Rebaudioside B.

The fourth stage of the process comprises removal of alcohol from the steviol glycoside eluate obtained after the third stage, and further concentration and drying of the steviol glycoside mixture to obtain a dried highly purified mixture of steviol glycosides. Any method known in the art may be used for ethanol removal, concentration and drying.

Purification of Reb D from a Low Purity Steviol Glycosides Mixture

The present invention is also directed to a method for preparing Rebaudioside D, or a purified steviol glycosides mixture and Rebaudioside D, including the steps of providing a steviol glycosides mixture, dissolving the steviol glycosides mixture in a solvent to produce a solution of steviol glycosides, passing the solution of steviol glycosides through a multi-column system including a plurality of columns packed with an adsorbent resin, eluting impurities from the multi-column system with water or an aqueous solution, eluting high Rebaudioside D fractions from the multi-column system with a first aqueous alcohol solution, crystallizing Rebaudioside D from solutions prepared from the high Rebaudioside D fractions, eluting steviol glycoside mixture fractions from the multi-column system with a second aqueous alcohol solution, and drying the steviol glycoside mixture fractions to obtain the purified steviol glycosides mixture.

According to the present invention the purification of steviol glycosides was developed from a steviol glycosides mixture with a TSG content of less than 95% w/w on a dry basis.

In one example the TSG content of an initial low purity steviol glycoside mixture was 84.3% w/w on a dry basis, and the Rebaudioside D content was 0.5% w/w on dry basis.

A column system as described above was used to purify a mixture of steviol glycosides.

In one embodiment, the method for isolation and purification of Rebaudioside D comprises passing an aqueous or aqueous alcoholic solution of a low purity steviol glycoside mixture through a consecutively connected column system. The water to alcohol ratio (vol/vol) in the aqueous alcoholic solution is 99.9:0.1 to 60:40. As a result different steviol glycosides are retained in different sections of the column system.

In one embodiment the columns with retained steviol glycosides are subjected to elution of compounds with a lower affinity, more specifically compounds other than steviol glycosides, in order to increase the purity level of the final products. Lower affinity compounds are subsequently eluted with an aqueous or aqueous alcoholic solution of an acid, aqueous or aqueous alcoholic solution of a base, and an aqueous alcoholic solution, in a specific order. The water to alcohol ratio (vol/vol) in the aqueous alcoholic solution is 99.9:0.1 to 60:40. The elution of lower affinity compounds is carried out either from each column separately (parallel connection) or from two or more consecutively (serially) connected columns.

A fraction with a high Rebaudioside D content is eluted from columns with an aqueous alcoholic solution. The water to alcohol ratio (vol/vol) in the aqueous alcoholic solution is in the range of 99.9:0.1 to 50:50. The elution of fractions with a high Rebaudioside D content may be carried out either from each column separately (parallel connection) or from two or more consecutively (serially) connected columns.

The remaining steviol glycoside fractions may be eluted from each column separately (parallel connection) or from two or more consecutively (serially) connected columns with an aqueous alcoholic solution. The water to alcohol ratio (vol/vol) in the aqueous alcoholic solution is in the range of 60:40 to 0.1:99.9.

The remaining steviol glycoside fractions may be subjected to drying to yield a highly purified steviol glycoside mixture with at least 95% (w/w) dry basis TSG content.

In one example the actual yield of the highly purified steviol glycoside mixture was 72% from theoretical. The combined Rebaudioside D fractions contained 15.1% Rebaudioside D (w/w) on a dry basis.

Fractions with a high Rebaudioside D content may be combined and mixed with aqueous alcohol. The water to alcohol ratio (vol/vol) in the resulting aqueous alcoholic solution is in the range of 99.9:0.1 to 0.1:99.9. Crystallization of Rebaudioside D is induced by adding Rebaudioside D crystals and maintaining the mixture at 0-60° C. with agitation during a period of from about 30 min to about 7 days. Crystals of Rebaudioside D are separated to yield a product with at least 60% (w/w) Rebaudioside D content on a dry basis.

In another embodiment high Rebaudioside D fractions are combined and dried, and then mixed with aqueous alcohol. The water to alcohol ratio (vol/vol) in the resulting aqueous alcoholic solution is in the range of 99.9:0.1 to 0.1:99.9. Crystallization of Rebaudioside D is induced by adding Rebaudioside D crystals and maintaining the mixture at 0-60° C. with agitation during a period of from about 30 min to about 7 days. Crystals of Rebaudioside D are separated to yield a product with at least 60% (w/w) Rebaudioside D content on a dry basis.

In one example the first crystallization yielded a product with at least 86% (w/w) Rebaudioside D content on a dry basis.

In another embodiment Rebaudioside D is further purified by suspending and agitating in water or aqueous alcohol at 0-60° C. during a period of from about 30 min to about 7 days, and then separating the Rebaudioside D crystals to obtain Rebaudioside D with a 95% (w/w) dry basis purity. The water to alcohol ratio (vol/vol) in the applied aqueous alcoholic solution is 99.9:0.1 to 0.1:99.9. If necessary this step may be repeated several times to obtain highly purified Rebaudioside D with at least 95% (w/w) dry basis purity.

In one example the yield of highly purified Rebaudioside D with 98.2% (w/w) dry basis purity was 70% of the Rebaudioside D content in the initial low purity steviol glycoside mixture.

Purification of Reb D from Plant Biomass

Diterpene glycosides, including sweet-tasting substances, are found in different parts of the *S. rebaudiana* Bertoni plant, being present at the highest concentration in the leaves. The leaves, therefore, are the preferred starting material for recovery of sweet glycosides.

The process of the present invention provides for complete retreatment of *Stevia rebaudiana* Bertoni plant extract, with isolation and purification of a highly purified steviol glycoside mixture or highly purified individual sweet glycosides, such as Rebaudioside D. The plant extract can be obtained using any method such as, but not limited to, the extraction methods described in U.S. Pat. No. 7,862,845, the entire contents of which are incorporated by reference herein.

One method for purifying Rebaudioside D from a *Stevia rebaudiana* Bertoni plant biomass, in accordance with the present invention, includes the steps of providing the biomass of the *Stevia rebaudiana* Bertoni plant, producing a crude extract by contacting the biomass with water, separating insoluble material from the crude extract to obtain a first filtrate containing steviol glycosides, and treating the first filtrate to remove high molecular weight compounds and insoluble particles, thereby obtaining a second filtrate containing steviol glycosides. The second filtrate is then treated with an ion-exchange resin to remove salts, thereby obtaining a resin-treated filtrate. The method further includes passing the resin-treated filtrate through a multi-column system including a plurality of columns packed with an adsorbent resin, to obtain at least one column having adsorbed steviol glycosides; treating the at least one column having adsorbed steviol glycosides with a washing solution to remove impurities; eluting the adsorbed steviol glycosides from the at least one column having adsorbed steviol glycosides, to obtain an eluted solution; treating the eluted solution to obtain a decolorized solution; evaporating solvent from the decolorized solution to obtain a high Rebaudioside D content mixture; combining the high Rebaudioside D content mixture with solvent to form a Rebaudioside D solution or suspension; and crystallizing Rebaudioside D from the Rebaudioside D solution or suspension to obtain Rebaudioside D crystals.

In one embodiment of the present invention, Rebaudioside D was isolated and purified at the extraction stage as follows. The dried and ground biomass of *Stevia rebaudiana* Bertoni was extracted by water, and remaining solids were separated by filtration. The filtrate was subjected to deionization and decolorization. Then, the resulting filtrate was passed through a series of chromatographic columns to separate high and low Rebaudioside D fractions. The resulting solutions were deionized, decolorized, concentrated and dried. Highly purified Rebaudioside D was obtained from the concentrate by treating with alcohol or alcohol-water solutions at various temperatures and times. Low Rebaudioside D fractions were combined, evaporated, deionized, decolorized, concentrated, and dried to produce a mixture of steviol glycosides with not less than 95% purity.

According to one aspect of the invention, a method for producing purified Reb D comprises the steps of: providing a biomass of *Stevia rebaudiana* Bertoni; producing a crude extract by contacting the biomass of *Stevia rebaudiana* Bertoni with an extracting solvent, such as water; separating insoluble material from the first extract to obtain a filtrate containing steviol glycosides; deionizing the filtrate; passing the filtrate feed over a series of columns packed with polar resin and eluting steviol glycosides to obtain eluates containing high Reb D and low Reb D fractions; decolorizing the solutions; evaporating and deionizing; concentrating by nano-filters and drying.

The process comprises drying of plant material at temperatures between about 20-60° C. for a period of about 2-3 hours to a moisture content of about 5-8% before extraction. The drying temperatures between 40-45° C. are more preferable because under those conditions the sweet glycosides are not decomposed. The dried plant material is milled. A particle size between about 10-20 mm is preferred. The plant material is then extracted by water in a continuous reflux extractor. The proportion of extraction water preferably is from about 20 liters to about 25 liters to one kilogram of leaves. The pH of water can be between about pH 2.0 and 7.0, however between pH 2.0 and 3.0 is preferable. A larger amount of water may be used; however, it is not preferable from a practical standpoint. The extraction temperature can be in the limits of about 25-90° C.; however, the temperatures between 50-60° C. are more preferable for the neutral pH of the extraction solvent. The extraction can be carried out in batch conditions; however, a continuous reflux extractor is more preferable as the extraction and separation of the residue is carried out simultaneously. Moreover, the volume of extract is less and the steviol glycoside content is higher in the case of a continuous reflux extractor. For the batch process the duration of extraction may range from about 0.5 hours to 24 hours, preferably from 1 hour to 6 hours. The contact time for a continuous process is in the range of about 2.5-3.0 hours.

At the extraction stage the pH of water is critical. In a crude *Stevia* extract there are many kinds of pigments and it is difficult to characterize the decolorization capacity for each pigment quantitatively. The visible absorption spectrum of the transparent solution of crude extracts is usually tested by a spectrophotometer. There are strong absorption peaks at 420 and 670 nm. The absorption peak at 420 nm results from red and yellow pigments, and the absorption at 670 nm results from chlorophyll. The concentration of chlorophyll in the transparent solution of crude extracts is very low due to its low solubility in water. However, the absorption at the wavelength of 370 nm is stronger than that at 420 nm. Thus, the content of pigments in the product is often characterized by measuring $E_{370}$, which is the absorption at the wavelength of 370 nm for a 1.0% aqueous product solution with 1.0 cm of thickness.

HPLC analysis was performed on an "Agilent 1100 series" (USA) liquid chromatograph equipped with a four channel solvent delivery system, autosampler, thermostatted column compartment and UV detector (210 nm) interfaced with "Chemstation" data acquisition software. Separation of steviol glycosides was performed on a "Zorbax $NH_2$ 150× 4.6 mm; 5 µm" chromatographic column. The flow rate was 1.0 mL/min and the mobile phase was an 80:20 (vol/vol.) acetonitrile and water (containing 0.025% acetic acid) mixture. The reference materials for steviol glycoside quantitation were Reb A, Reb C, Stevioside, and Dulcoside A standards produced by Chromadex Inc. (USA). Reb B, Reb D (also available from Chromadex), Reb E, Reb F, Rubusoside and Steviolbioside reference materials were prepared and characterized at the PureCircle R&D center. The steviol glycosides were identified by their retention times. The concentrations were calculated by an external standards method and reported on a dry weight basis.

It was shown that at the lower pH at 20° C. the amount of colored compounds is lower while the quantity of extracted steviol glycosides remain at the same level. The effect of pH on steviol glycosides and color extraction is summarized in TABLE 2.

TABLE 2

| pH | Total extracted steviol glycosides, mg/g of leaves | $E_{370}$ of the filtrate |
|---|---|---|
| 2.0 | 10.4 | 3.4 |
| 5.0 | 10.2 | 4.2 |
| 7.0 | 10.0 | 6.5 |
| 9.0 | 9.8 | 7.9 |

Thus, an acidic pH is preferable for the preparation of extract with a low content of pigments. For the acidification of extracting water, any mineral or organic acid can be used. However, citric and phosphoric acids are preferable because they can be removed during further treatment by calcium oxide.

The variation of extraction rates of individual glycosides at different pH values and temperatures is summarized in TABLE 3.

TABLE 3

| Conditions | | St* | RebA | RebC | RebD | RebB | RebE | RebF | StBio | DulA |
|---|---|---|---|---|---|---|---|---|---|---|
| pH 2.0 | 4° C. | 23.6 | 60.7 | 11.7 | 1.7 | 0.1 | 0.2 | 1.2 | 0.4 | 0.4 |
| | 22° C. | 21.1 | 62.0 | 12.1 | 1.8 | 0.1 | 0.3 | 1.4 | 0.7 | 0.5 |
| | 50° C. | 18.0 | 64.1 | 12.2 | 1.9 | 0.1 | 0.5 | 1.6 | 1.0 | 0.6 |

TABLE 3-continued

| Conditions | | St* | RebA | RebC | RebD | RebB | RebE | RebF | StBio | DulA |
|---|---|---|---|---|---|---|---|---|---|---|
| pH 5.0 | 4° C. | 20.2 | 61.1 | 13.4 | 2.3 | 0.1 | 0.3 | 2.0 | 0.1 | 0.5 |
|  | 22° C. | 20.8 | 61.8 | 11.5 | 2.4 | 0.1 | 0.4 | 2.3 | 0.1 | 0.6 |
|  | 50° C. | 21.0 | 62.5 | 9.8 | 2.5 | 0.1 | 0.5 | 2.4 | 0.1 | 1.1 |
| pH 7.0 | 4° C. | 21.1 | 63.0 | 10.1 | 2.4 | 0.1 | 0.5 | 2.2 | 0.1 | 0.5 |
|  | 22° C. | 21.0 | 63.1 | 9.5 | 2.6 | 0.1 | 0.6 | 2.4 | 0.1 | 0.6 |
|  | 50° C. | 20.1 | 62.6 | 9.6 | 2.8 | 0.1 | 0.6 | 3.0 | 0.1 | 1.1 |
| pH 9.0 | 4° C. | 24.6 | 58.7 | 10.2 | 2.9 | 0.6 | 0.1 | 1.9 | 0.3 | 0.7 |
|  | 22° C. | 25.5 | 55.3 | 11.1 | 3.2 | 0.8 | 0.1 | 2.3 | 0.5 | 1.2 |
|  | 50° C. | 29.6 | 48.8 | 10.2 | 3.9 | 1.1 | 0.2 | 4.0 | 0.8 | 1.4 |

*St - Stevioside; StBio - Steviolbioside; DulA - Dulcoside A; Rub - Rubusoside.

Within the pH range of 2.0-7.0, the extraction rate of Stevioside remains practically the same; however, at alkaline pH values it increases with increasing temperature. The extraction rate of Reb A generally increases with the increase of temperature and remains practically the same at the pH range of 2.0-7.0, while at alkaline pH values it is significantly lower. At alkaline pH values the content of minor glycosides such as Reb B, D, and F, Steviolbioside, and Dulcoside A are considerably higher as well. While not intending to be bound by theory, it is likely that at alkaline conditions the transformation of Reb A to Reb B and conversion of Stevioside to the Steviolbioside also takes place. The transformation of Stevioside to the Steviolbioside may occur at acidic pH as well. Extraction rates of Reb D, E, and F increase at higher temperatures.

Thus, the application of acidic pH values and moderate temperatures is preferable with respect to a high content of Reb A, and low contents of Reb B, Reb D and Reb F; however the quantity of Steviolbioside is higher in these conditions. In the case of acidic pH values the extraction temperature has to be as low as possible to prevent the formation of Steviolbioside. In the case of alkaline pH values the content of coloring compounds is higher. However, if the extract will be used for further production of highly purified individual glycosides such as Reb A and especially Reb D, the moderate temperatures and pH values around 5.0-7.0 are more preferable. In that case the content of Reb B and Steviolbioside in the final extract is low.

The ratio of leaves and water is also important. The higher the ratio, the higher the extracted amount of non-glycosidic compounds, while at the very low ratios the quantity of solvent is insufficient for the complete extraction of sweet glycosides. At continuous conditions and 35-40° C. the preferable ratio of leaves to water is within the limits of about 1:20 to 1:25, wt/vol. (pH 4.5) (TABLE 4). The contact time is around 150-160 min. An increase in process duration leads to higher levels of undesirable compounds in the extract, while a short time is not enough for complete extraction of sweet glycosides (TABLE 5).

TABLE 4

| Leaves:Water ratio | Total steviol glycosides, mg/g leaves | $E_{370}$ of the filtrate |
|---|---|---|
| 1:3.0 | 50.1 | 7.1 |
| 1:5.0 | 51.3 | 5.9 |
| 1:7.0 | 68.2 | 5.3 |
| 1:10.0 | 74.4 | 4.4 |
| 1:15.0 | 85.6 | 3.8 |
| 1:20.0 | 87.2 | 3.5 |

TABLE 4-continued

| Leaves:Water ratio | Total steviol glycosides, mg/g leaves | $E_{370}$ of the filtrate |
|---|---|---|
| 1:25.0 | 88.4 | 3.6 |
| 1:30.0 | 89.0 | 4.1 |
| 1.35.0 | 93.5 | 4.4 |

TABLE 5

| Time, min | Total steviol glycosides, mg/g leaves | $E_{370}$ of the filtrate |
|---|---|---|
| 50 | 67.2 | 3.0 |
| 100 | 81.4 | 3.0 |
| 150 | 88.4 | 3.5 |
| 180 | 89.1 | 3.9 |
| 200 | 91.2 | 4.3 |

Extraction can be done either at batch conditions or by continuous countercurrent technique. Alternatively, any other types of extraction techniques can be applied for the primary isolation of *Stevia* sweet glycosides, such as ultrasonic extraction, pressurized extraction, microwave conditions or combinations thereof.

The plant material is separated from the solution by filtration and the pH of the filtrate is adjusted to about 8.5-10.0 with calcium oxide or hydroxide (about 1.0% from the volume of filtrate) with slow continuous agitation for about 10-15 min. A lower amount of calcium oxide is not sufficient for satisfactory decolorization of the extract, while high concentrations will require a larger capacity of ion-exchange resins and more activated carbon in further stages. The concentrations between 1.0-2.0% are preferable. The process is preferably carried out in a fast manner, as high pH promotes the formation of Reb B, which further will impact the efficiency of the purification of individual glycosides and the taste profile of the extract.

The pH of the suspension obtained after treatment with calcium oxide is adjusted to pH 3.0-4.0, preferably to pH 3.0-3.5, by adding $FeCl_3$. Other soluble trivalent ferrous salts may be used. The mixture is maintained for 10-15 min with slow agitation. The process is preferably carried out in a fast manner, as low pH promotes the conversion of Stevioside to Steviolbioside, which further will affect the efficiency of the purification of individual glycosides and the taste profile of the extract.

A small amount of calcium oxide is further added to adjust the pH to around 8.5-9.0, and the mixture is maintained for about 15-40 min, preferably 25-30 min, with slow agitation.

This scheme of chemical treatment results in an extract of slightly yellowish color. The effect of chemical treatment on the decolorization of extract is summarized in TABLE 6.

TABLE 6

| Stage | pH | $E_{370}$ of the filtrate |
|---|---|---|
| After CaO-I | 8.5-10.0 | 2.5 |
| After FeCl$_3$ | 3.0-4.0 | 1.6 |
| After CaO-II | 8.5-9.0 | 0.8 |

The separation of precipitate can be carried out in any type of filtration system.

The filtrate was subjected to the preliminary deionization by treatment with a cation-exchange resin such as Amberlite FPC22H (H$^+$) followed with an anion-exchange resin such as Amberlite FPA53 (OH$^-$) in a conventional manner in continuous conditions. Generally any type of strong cation-exchanger and weak anion-exchangers can be used in this stage. The flow rate in the case of both resins was maintained between bed volumes (BV) of 0.5-1.0 hour$^{-1}$. The anion-exchanger shows significant decolorizing ability. After this treatment the $E_{370}$ value of the filtrate decreases up to 0.12-0.15. Upon completion of the mixture, the ion-exchange resin columns were washed with RO water to recover the steviol glycosides left in the columns. The deionization stage is important for the decolorizing of product, for more efficient further adsorption of steviol glycosides on specific resins, and for prevention of adsorbent resin damage.

The deionized solution was passed through consecutively connected columns packed with specific polar macroporous polymeric adsorbent. The adsorption rate of some impurities such as sterebins is significantly higher than that for steviol glycosides. On the other hand during desorption stage the impurities desorb faster than sweet compounds, which results in a low quality of final extract. In particular, the steviol glycosides content is only about 85-86% and the $E_{370}$ is around 0.13. To solve this problem and increase the efficiency of this stage, an additional column with specific adsorbent was applied in the first position as an "impurities catcher". The size of the "catcher column" was about ⅓ of the others. The BV was around 1.0 hour$^{-1}$. Upon complete passage of solution, the resin sequentially was washed with 1 volume of water, 2 volumes of 0.5% NaOH, 1 volume of water, 2 volumes of 0.5% HCl, and finally with 2 volumes of water until it reached a neutral pH.

Desorption of the adsorbed steviol glycosides was carried out with 50-52% ethanol at BV=1.0-1.5 hour$^{-1}$. Desorption of the first "catcher column" was carried out separately and its eluate was separated from the main solution obtained from other columns. The $E_{370}$ of the filtrate obtained from the "catcher column" was about 0.8, while for the other columns it was around 0.035-0.04. Steviol glycoside content in the "catcher column" was significantly low as well. The quality of extract from different columns with specific macroporous adsorbent is shown in TABLE 7.

TABLE 7

| Columns | Total steviol glycosides, % | $E_{370}$ of the filtrate |
|---|---|---|
| "Catcher" | 62.3 | 0.80 |
| First | 82.4 | 0.041 |
| Second | 87.6 | 0.040 |
| Third | 92.8 | 0.040 |
| Fourth | 93.2 | 0.039 |
| Fifth | 93.4 | 0.039 |
| Sixth | 93.4 | 0.039 |

During the adsorption process the column outlets were monitored and samples were taken from first glycoside containing fractions (first sweet fractions) of each column and analyzed. In a seven column system, where the first one is a "catcher", it was shown that if the quantity of the steviol glycosides passed through the columns was around 9.5-9.7% from total volume of the columns, the content of Stevioside decreased from 34.9% in the outlet of the "catcher" column to 9.0% in the sixth. At the same time the content of Reb A increased from 44.8% of initial extract to 73.0% in the first portion of the sixth column. Similarly the content of Reb D increased from 2.1% of initial extract to 12.0% in the first portion of the last column. Apparently, the adsorption rate of Reb D is lower compared with Stevioside and Reb A. In the case of Reb C and Dulcoside A the reverse correlation is revealed. The ratio of various glycosides at the outlet of each column (first sweet fraction) during adsorption, in the case of 120 g of total solids subjected to the treatment, is summarized in TABLE 8.

TABLE 8

| Column | Steviol glycosides, % |||||||||
|---|---|---|---|---|---|---|---|---|---|
| | St | RebA | RebC | RebD | RebB | RebE | RebF | StBio | DulA |
| "Catcher" | 34.9 | 45.2 | 13.9 | 2.3 | 1.1 | 0.7 | 0.9 | 0.1 | 0.9 |
| First | 26.3 | 52.9 | 13.3 | 3.8 | 1.0 | 0.8 | 1.0 | 0.1 | 0.8 |
| Second | 22.6 | 57.5 | 11.4 | 4.8 | 1.2 | 0.7 | 1.1 | 0.1 | 0.6 |
| Third | 14.8 | 65.0 | 8.3 | 6.9 | 2.3 | 1.0 | 1.4 | 0.1 | 0.2 |
| Fourth | 13.1 | 67.6 | 8.1 | 6.6 | 2.1 | 0.8 | 1.4 | 0.1 | 0.2 |
| Fifth | 11.1 | 68.7 | 7.3 | 7.7 | 2.1 | 1.3 | 1.5 | 0.1 | 0.2 |
| Sixth | 9.0 | 73.0 | 3.6 | 12.0 | 0.1 | 0.9 | 1.2 | 0.1 | 0.1 |
| Initial extract | 35.1 | 44.8 | 13.3 | 2.1 | 0.3 | 0.5 | 2.3 | 0.1 | 1.5 |

The content and ratio of various glycosides in the subsequent portions (after first sweet fraction) of column effluent changed significantly. Reb A, D, and B contents decreased with the volume of column effluent, while the quantity of Reb C and Stevioside increased. The contents of other glycosides were practically at the same level. However after saturation of the resin in all columns the composition of effluent was almost the same as that for the initial extract.

The content of various glycosides in various fractions of column effluent during adsorption is shown in TABLE 9.

Thus, Reb A, D, B, and F contents were increasing before resin saturation, but decreasing again after saturation of the resin. Stevioside and Reb C contents were decreasing during initial stages of adsorption, and increasing again with the volume of effluent. No significant changes were observed in the content of other glycosides. Therefore, to produce an extract with a high content of Reb A or low content of Stevioside the initial portions of solution at the outlet of the columns has to be collected separately. To increase the quantity of that type of product additional sections of the columns can be used. To produce Stevia extract with a low content of Reb D the solution has to be collected after saturation of the resin, i.e. the first sweet fractions of the column effluent have to be excluded. It is notable that the Reb D content in column effluent changes rapidly. The Stevia extract with a low content of Reb C can be produced if collecting an intermediate portion of column effluent. The Reb B quantity can be maintained at a low level, if the extraction and purification process is controlled.

TABLE 9

| Effluent:Resin ratio, vol/vol. | Steviol glycosides, % | | | | | | | | |
|---|---|---|---|---|---|---|---|---|---|
| | St | RebA | RebC | RebD | RebB | RebE | RebF | StBio | DulA |
| 1:1.2 | 9.0 | 73.0 | 3.6 | 12.0 | 0.1 | 0.9 | 1.2 | 0.1 | 0.1 |
| 1:1.3 | 12.2 | 71.0 | 6.1 | 6.2 | 2.2 | 0.9 | 1.2 | 0.1 | 0.1 |
| 1:1.4 | 16.0 | 67.7 | 7.9 | 5.0 | 1.3 | 0.8 | 1.1 | 0.1 | 0.1 |
| 1:1.6 | 19.0 | 64.8 | 8.6 | 4.3 | 1.1 | 0.7 | 1.2 | 0.1 | 0.2 |
| 1:2.0 | 25.1 | 58.5 | 10.2 | 3.3 | 0.7 | 0.6 | 1.2 | 0 | 0.4 |
| 1:2.3 | 27.0 | 56.7 | 10.6 | 2.9 | 0.6 | 0.6 | 1.1 | 0 | 0.5 |
| 1:2.5 | 28.6 | 55.1 | 10.9 | 2.8 | 0.3 | 0.5 | 1.2 | 0 | 0.6 |
| 1:3.0 | 29.1 | 54.0 | 11.5 | 2.7 | 0.5 | 0.4 | 1.2 | 0 | 0.6 |
| 1:3.5 | 31.8 | 50.4 | 12.1 | 2.6 | 0.5 | 0.7 | 1.1 | 0 | 0.8 |
| 1:4.0 | 33.5 | 48.7 | 12.6 | 2.2 | 0.4 | 0.4 | 1.1 | 0 | 1.1 |
| 1:4.5 | 34.4 | 47.7 | 13.4 | 2.2 | 0.5 | 0.5 | 1.2 | 0 | 0.1 |
| 1:5.0 | 35.0 | 46.9 | 13.6 | 2.2 | 0.5 | 0.5 | 1.2 | 0 | 0.1 |
| Initial extract | 35.1 | 44.8 | 13.3 | 2.1 | 0.3 | 0.5 | 2.3 | 0.1 | 1.5 |

A similar correlation was observed in the case of applying 7.5-8.0% of solids to the total volume of resin. The content of Stevioside among the adsorbed glycosides was higher in the initial columns and decreasing in the following ones while the content of Reb A increased from the first column to the sixth column. The affinity of Stevioside to the adsorbent is significantly higher than that of Reb A. The Reb C content adsorbed on the resin was practically unchanged in the first four columns and decreased significantly from the fifth column. The Reb D content adsorbed on the resin is significantly lower than in the column effluent; however, it is increasing in the final sections. The contents of Reb E, Reb F, and Dulcoside A decrease from the first to final section, as shown in TABLE 10, in the case of 90 g of total solids subjected to the treatment using six columns, with 200 mL resin in each column. Thus, if the elution of each column is carried out separately, the *Stevia* extract with a high content of Stevioside, Reb A or Reb D and desired amounts of other glycosides can be produced.

TABLE 10

| Column | Steviol glycosides, % | | | | | | | | |
|---|---|---|---|---|---|---|---|---|---|
| | St | RebA | RebC | RebD | RebB | RebE | RebF | StBio | DulA |
| Initial Extract | 35.1 | 44.8 | 13.3 | 2.1 | 0.3 | 0.5 | 2.3 | 0.1 | 1.5 |
| First | 40.7 | 39.1 | 11.1 | 1.5 | 0.2 | 0.5 | 2.4 | 0.1 | 4.4 |
| Second | 38.1 | 40.6 | 12 | 1.8 | 0.4 | 0.5 | 2.5 | 0 | 4.1 |
| Third | 36.4 | 42.1 | 12.6 | 2.5 | 0.6 | 0.4 | 2.7 | 0 | 2.7 |
| Fourth | 31.7 | 50 | 11.2 | 2.8 | 0.8 | 0.2 | 2.5 | 0 | 0.8 |
| Fifth | 20.1 | 63.7 | 8.1 | 4.2 | 1.8 | 0.2 | 1.5 | 0 | 0.4 |
| Sixth | 10.3 | 66.6 | 4.4 | 15.4 | 2.0 | 0.2 | 1.0 | 0 | 0.1 |

However, when the adsorbent is saturated with glycosides the ratio of various glycosides become practically the same in all the columns.

The decrease in the quantity of *Stevia* extract subjected to the chromatographic treatment results in an increase of Reb D content in the final column. However the quantity has to be enough for more than five columns in the case of a six column system. The correlation between *Stevia* extract quantity and Reb D content in the final column is summarized in TABLE 11, in the case of six columns which are each packed with 200 mL resin.

TABLE 11

| Quantity of Stevia extract, g | RebD content in the sixth column, % |
|---|---|
| 116.0 | 4.1 |
| 110.0 | 7.3 |
| 95.0 | 13.2 |
| 90.0 | 15.4 |
| 85.0 | 35.3 |

Figure 4:
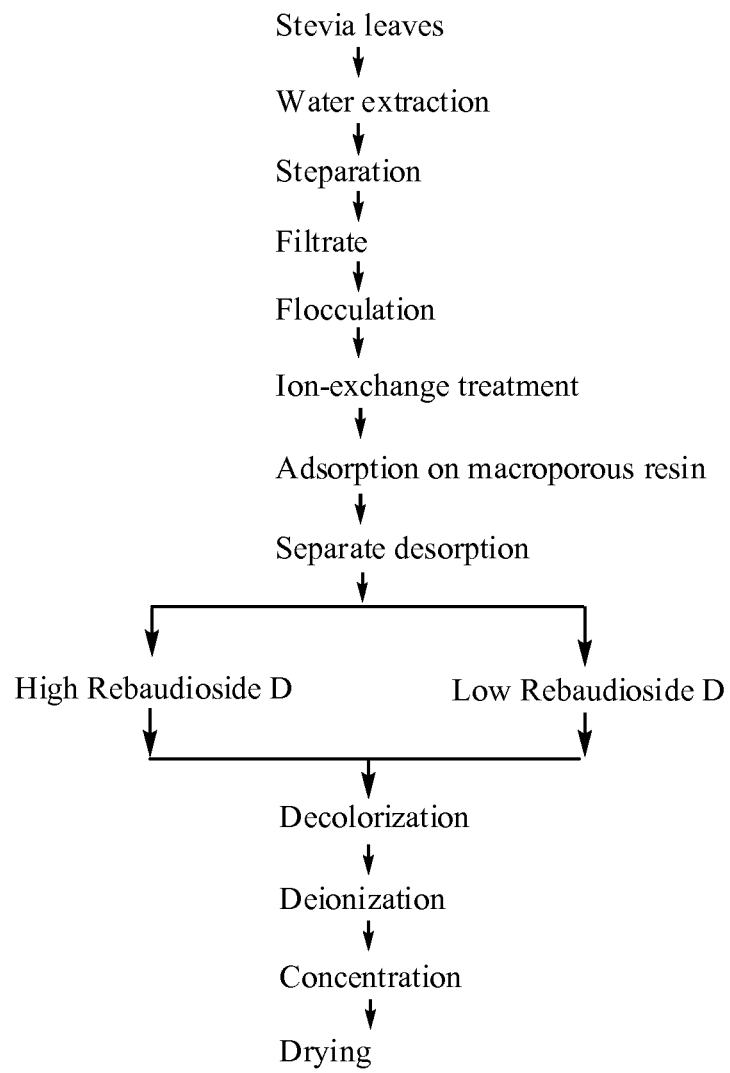
FIG. 4 is a diagram illustrating the purification of Rebaudioside D from the extraction stage.

A flow-chart of the isolation of the high Reb D and low Reb D containing fractions, during the extract purification stage on macroporous polar resin, is presented in FIG. 4.

Figure 5:
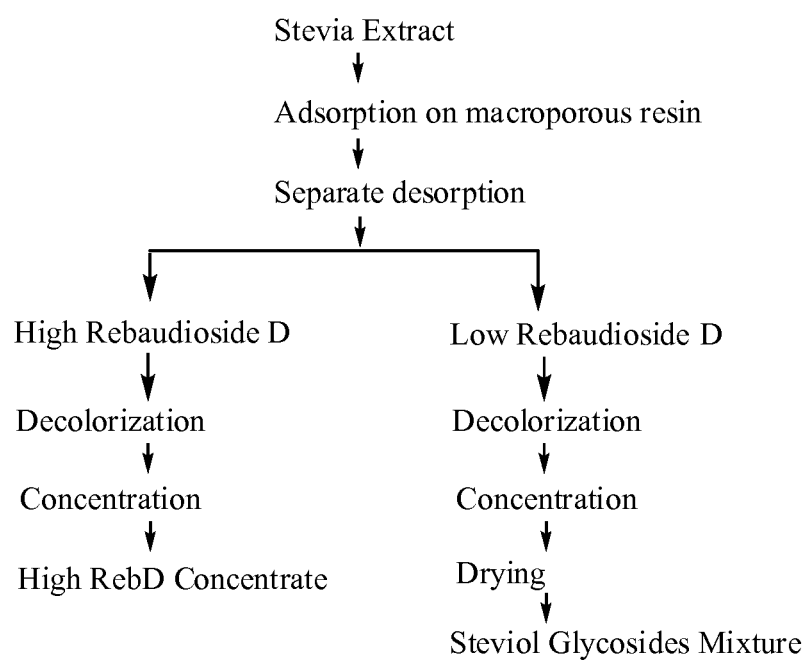
FIG. 5 is a diagram illustrating the isolation of Rebaudioside D fractions from the portion of a *Stevia* extract adsorbed on a macroporous resin.

FIG. 5 illustrates the isolation of high Reb D fractions from *Stevia* extract adsorbed on macroporous resin.

In the case when the steviol glycoside quantity in the feed exceeds the adsorption capacity of the resin, the steviol glycosides unable to adsorb due to saturation of the resin will "escape" through the system and form a water fraction. This water fraction is distinguished by a high content of Reb D and Reb A and low content of Stevioside. The content of steviol glycosides in different columns and water fractions, in the case of 130 g of *Stevia* extract subjected to the treatment using six columns packed with 200 mL of macroporous resin, is summarized in TABLE 12. The contents of Reb A and Reb D in the water fraction are decreasing with the increase of the quantity of feed extract. The content of steviol glycosides in the water fraction at various quantities of initial extract subjected to the treatment, using six columns which are each packed with 200 mL of macroporous resin, is summarized in TABLE 13.

TABLE 12

| Column | Steviol glycosides, % | | | |
|---|---|---|---|---|
| | Stevioside | RebA | RebC | RebD |
| Initial Extract | 33.7 | 53.2 | 11.3 | 1.8 |
| First | 40.9 | 45.9 | 12.3 | 0.9 |
| Second | 41.7 | 46.1 | 11.6 | 0.6 |
| Third | 40.3 | 48 | 10.7 | 1.0 |
| Fourth | 37.7 | 50.1 | 11.0 | 1.2 |
| Fifth | 35.1 | 52.9 | 10.7 | 1.3 |
| Sixth | 28.5 | 60.7 | 8.8 | 2.0 |
| Water fraction | 7.4 | 70.4 | 3.7 | 18.5 |

As mentioned above the adsorbed steviol glycosides are eluted during the desorption stage. Higher or lower concentrations of ethanol can be used for desorption. However, at concentrations lower than 50% desorption time increases significantly, while higher concentrations result in lower quality of the extract.

TABLE 13

| Quantity of Stevia extract, g | Steviol glycosides, % | | | |
|---|---|---|---|---|
| | Stevioside | RebC | RebA | RebD |
| Initial extract | 33.7 | 11.3 | 53.2 | 1.8 |
| 120.0 | 3.5 | 4.2 | 71.5 | 20.8 |
| 130.0 | 7.4 | 3.8 | 70.4 | 18.4 |
| 140.0 | 20.5 | 9.8 | 60.1 | 9.6 |

The combined solution of steviol glycosides eluted from macroporous adsorbent was treated with activated carbon. High Reb D fractions were collected separately. The solution from the "catcher column" was not mixed with others. The high Reb A and Stevioside fractions may also be collected separately. The quantity of the carbon was in the range of 0.1-0.8% (wt/vol.), and preferably 0.25-0.3% (wt/vol.). The suspension with continuous agitation was maintained at 20-25° C. for 20-120 min, and preferably for 25-35 min. Separation of used carbon was conducted on the plate-and-frame press filter; however, filtration can be performed by any other equipment suitable to separate fine particles from solution. This treatment is very efficient for decolorizing, and for decreasing the $E_{370}$ value of the steviol glycosides up to 0.03 absorbance units. Application of larger quantities of activated carbon is not desirable because of strong adsorption of steviol glycosides to the carbon and thus loss of the product.

The further purification and decolorization of the solution was accomplished by treatment with ion-exchange resins. For that purpose the ethanol solution of steviol glycosides, after treatment with activated carbon, was passed through columns packed with cation-exchange resin Amberlite FPC22H (H$^+$) followed with anion-exchange resin Amberlite FPA53 (OH$^-$). Generally any type of strong cation-exchanger and weak anion-exchangers can be used at this stage. The flow rate for both resins was between BV=0.5-1.0 hour$^{-1}$. This treatment has a significant decolorizing effect, decreasing the $E_{370}$ value of the filtrate up to 0.02 absorbance units. To wash out coloring substances adsorbed on the ion-exchangers, the columns were washed with 2% NaOH solution in 60% of ethanol.

After passing through the ion-exchange columns, the solution was collected and transferred to a distillation device. The recovery of ethanol may be carried out on any type of evaporator, with or without vacuum. The solids content in the final concentrate was about 13-15%.

The evaporated concentrate was subjected to additional treatment with a cation-exchange resin such as Amberlite FPC22H (H$^+$) followed by an anion-exchange resin such as Amberlite FPA53 (OH$^-$) in a conventional manner in continuous conditions. The flow rate in both columns was maintained between BV=0.5-1.0 hour$^{-1}$. After completely passing the solution through the columns, both resins were washed with tap water to recover the steviol glycosides left in the columns. After this treatment the $E_{370}$ of the filtrate was around 0.01-0.014 absorbance units.

The refined extract was transferred to the nano-filtration device and concentrated to about 52% of solids content. Alternatively, the concentration can be carried out in any evaporating device, preferably under reduced pressure conditions. However, nano-filtration is preferable, because it allows the removal of residual amounts of low-molecular weight impurities. Moreover, the process is carried out at ambient temperature and mild conditions. When vacuum evaporators or distillation devices are used there is a possibility of Reb B and Steviolbioside formation at elevated temperatures.

The purified extract was spray dried in a conventional manner.

Steviol glycoside content in an extract purified in this manner was in the range of 96-97%, and the $E_{370}$ of a 1% solution was about 0.012 absorbance units. The specific rotation was in the range of –30.5 to –36.6° depending on the Reb A and Stevioside content in the extract. Heavy metals content was less than 1 ppm and ash content was less than 0.1%.

The combined fractions with a high content of Reb D eluted from the specific resin were decolorized, deionized and concentrated as described above.

The content of Reb D in the solutions can be increased up to about 70-80%, after chromatographic re-treatment similar to that described above. Further purification of Reb D can be carried out either from concentrated solution or powder.

Figure 6:
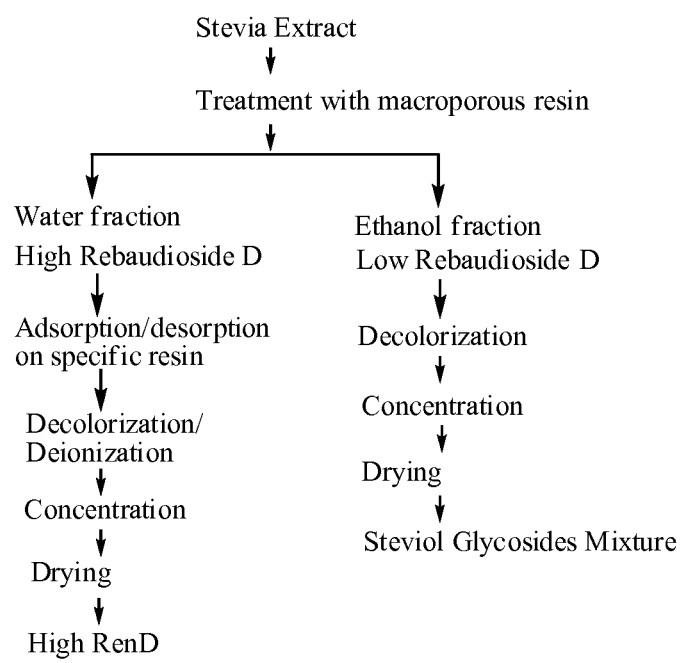
FIG. 6 is a diagram illustrating the isolation of Rebaudioside D fractions from the portion of a *Stevia* extract which was not adsorbed on a macroporous resin (i.e. the water fraction).

A flow chart illustrating the isolation of high Reb D containing fractions in the extraction stage, from the portion of *Stevia* extract not adsorbed on macroporous resin, is presented in FIG. 6.

To carry out the purification of Reb D from concentrated solution, the solution was mixed with anhydrous methanol and stirred at 20-22° C. for 24 hours. The best output was obtained at a 33-35% solids concentration. The effect of the solids concentration of the initial syrup, subjected to precipitation using anhydrous methanol in the ratio of 1:2 (vol/vol.), on the yield of crude Reb D is summarized in TABLE 14.

TABLE 14

| Concentration, % | Reb D yield, % from maximum |
|---|---|
| 25.0 | 21 |
| 30.0 | 36 |
| 33.0 | 100 |
| 35.0 | 100 |
| 37.0 | 95 |
| 40.0 | 62 |
| 50.0 | 23 |
| 60.0 | 12 |

The best ratio of Reb D concentrate to methanol was 1:2 (vol/vol.). At the lower ratios no precipitation took place, as shown in TABLE 15.

TABLE 15

| RebD Concentrate/Methanol Ratio | Reb D yield, % from maximum |
|---|---|
| 1:0.5 | 0 |
| 1:1.0 | 0 |
| 1:1.5 | 57 |
| 1:2.0 | 100 |
| 1:2.5 | 81 |
| 1:3.0 | 64 |
| 1:3.5 | 53 |
| 1:4.0 | 44 |

The purity of Reb D was in the range of 84-88%.

To effect further purification the crystals were suspended in a mixture of alcohol and water; agitated at 40-75° C., preferably 55-60° C., for 5-60 min, preferably 15-30 min; cooled down to 20-22° C.; and agitated for another 1-5 hours, preferably 1-2 hours.

At this stage both ethanol and methanol may be used. Water content is essential to produce high purity product. The effect of the solvent's water content when the ratio of crude Reb D to methanol-water solution is 1:3 (wt/vol.) is summarized in TABLE 16.

TABLE 16

| Concentration of methanol | RebD purity, % | Yield, % |
|---|---|---|
| Crude RebD | 84.3 | — |
| 99.0 | 85.6 | 98.4 |
| 95.0 | 86.1 | 98.2 |
| 90.0 | 87.2 | 97.9 |
| 85.0 | 87.8 | 97.6 |
| 80.0 | 88.6 | 97.5 |
| 75.0 | 89.3 | 97.2 |
| 70.0 | 89.6 | 96.8 |
| 65.0 | 92.4 | 95.1 |
| 60.0 | 95.8 | 91.7 |
| 55.0 | 95.8 | 88.3 |
| 50.0 | 95.1 | 73.3 |
| 45.0 | 95.1 | 71.6 |
| 40.0 | 94.9 | 69.3 |

When ethanol was used, the best results were obtained at the 45-55% concentration. However, when using ethanol the mixing time is preferably about 12-18 hours to get a high degree of purification.

At this stage the purification may also be carried out by washing with water.

To produce Reb D with 99% or greater purity, the step of washing with an alcohol-water solution or water may be repeated.

The purification of crude Reb D in powder form was carried out by crystallization from an alcohol-water solution or washing with water, as described above.

The purification of crude Reb D in powder or syrup form from the last column fraction of the specific resin was carried out according to the schemes described above.

Purification of Reb D Along with Reb A from *Stevia* Extract

In another embodiment of this invention Reb D purification is carried out using commercial *Stevia* extract as a starting material. The content of Reb D in the extract can vary depending on the *Stevia* plant variety or the technological scheme of the extract preparation.

In another embodiment of the present invention, the isolation and purification of Rebaudioside D and Rebaudioside A was carried using *Stevia* extract as a starting material. The method comprises the treatment of *Stevia* extract with alcohol or alcohol-water solutions to isolate Rebaudioside A with a relatively high content of Rebaudioside D; separation of the crystals and their treatment with alcohol or alcohol-water solutions to produce highly purified Rebaudioside A in precipitate, and a filtrate with high Rebaudioside D content; drying the precipitate to produce high purity Rebaudioside A; evaporation of alcohol from the filtrate; and treating the concentrated or dried solution of Rebaudioside D with alcohol or alcohol-water solutions at various temperatures and times to produce high purity Rebaudioside D.

Unless indicated otherwise, *Stevia* extract containing Stevioside at 22.63%, Reb A at 52.46%, Reb C at 7.52%, Reb D at 1.18%, Reb B at 0.55%, Reb E at 0.64%, Reb F at 1.79%, Steviolbioside at 0.10%, and Dulcoside A at 1.59%, with 88.46% total steviol glycosides content, was used as starting material in this embodiment.

In one embodiment of the present invention, *Stevia* extract was dissolved in an ethanol-water solution at 50-70° C., preferably 55-60° C.; incubated for about 10-30 min, preferably 15-20 min; and then at 15-40° C., preferably 20-22° C., for about 18-48 hours, preferably 20-24 hours, with agitation. When the temperature reached 22° C., 1-2% (wt/vol.) of highly purity (>97%) Reb A was added to the reaction mixture as a starter to initiate crystallization. The proportion of extract and ethanol-water solution varied depending on the content of minor compounds, particularly Reb B, D and Steviolbioside, and was between 1.0:2.5 and 1.0:10.0 (wt/vol.), and preferably between 1.0:3.0 and 1.0:5.0 (wt/vol.).

The concentration of ethanol may be from 75-99%, and preferably from 82-88%.

During incubation precipitate was formed, which was separated by filtration or centrifugation. The purity and yield of Reb A depended on the extract to ethanol ratio and concentration of ethanol (TABLES 17 and 18). The content of Reb A and Reb D in the final product ranged between 80-99% and 0.8-3.5% respectively. Therefore, this scheme is useful for the one-stage production of highly purified Reb A.

TABLE 17

| Ethanol, % | Extract:ethanol ratio, wt/vol. | Steviol glycosides, % | | | | Yield, % |
|---|---|---|---|---|---|---|
| | | St | RebC | RebA | RebD | |
| 75 | 1:3.0 | 0.1 | 0.2 | 98.9 | 0.8 | 19.2 |
| 78 | -"- | 0.1 | 0.2 | 98.6 | 1.1 | 21.3 |
| 80 | -"- | 0.1 | 0.2 | 98.3 | 1.4 | 23.4 |
| 82 | -"- | 0.1 | 0.2 | 97.9 | 1.8 | 23.7 |
| 85 | -"- | 0.1 | 0.2 | 97.7 | 2.0 | 24.1 |
| 87 | -"- | 0.3 | 0.4 | 96.8 | 2.5 | 25.6 |
| 88 | -"- | 0.4 | 0.5 | 95.6 | 3.5 | 33.0 |
| 89 | -"- | 1.0 | 0.7 | 94.8 | 3.5 | 35.4 |
| 90 | -"- | 1.4 | 1.2 | 94.4 | 3.0 | 35.7 |
| 95 | -"- | 3.2 | 3.1 | 91.2 | 2.5 | 41.6 |
| 99 | -"- | 7.2 | 10.3 | 80.4 | 2.1 | 48.3 |

TABLE 18

| Ethanol, % | Extract: ethanol ratio, wt/vol. | Yield of Product, % | RebA content, % | RebD content, % |
|---|---|---|---|---|
| 88.0 | 1:5.0 | 26.5 | 98.0 | 1.5 |
| 88.0 | 1:4.0 | 31.3 | 97.5 | 2.0 |
| 88.0 | 1:3.5 | 32.4 | 96.9 | 2.6 |
| 88.0 | 1:3.0 | 33.0 | 95.6 | 3.5 |
| 88.0 | 1:2.5 | 35.6 | 91.7 | 2.7 |
| 88.0 | 1:2.0 | 41.4 | 89.8 | 3.2 |

The Reb D content increases with the increase of ethanol concentration and decrease of solution to solids ratio. At the same time, the purity of Reb A increases in the case of more diluted ethanol solutions and higher ratios of ethanol to extract.

The precipitate, separated by filtration or centrifugation, was washed with about two volumes of absolute ethanol and dried.

The yield of the product (Reb A) at this stage for *Stevia* extracts with various contents of Reb A, after treatment with 88% ethanol (1:3 wt/vol. ratio), is summarized in TABLE 19. As could be expected, the yield of the product increases with the increase of the content of Reb A in the initial extract.

TABLE 19

| Reb A content in initial extract, % | Yield of Reb A at precipitation stage from initial extract, % |
|---|---|
| 42.0-43.0 | 28.0-30.0 |
| 45.0-46.0 | 32.0-35.0 |
| 50.0-53.0 | 32.0-38.0 |
| 55.0-59.0 | 41.0-42.0 |
| 60.0-62.0 | 45.0-46.0 |

If the initial extract contains high amounts of Reb B and Reb D, lower concentrations of ethanol and a higher ratio of ethanol to the extract are preferred for Reb A, and later Reb D, purification (TABLE 20; TABLE 21).

The yield of Reb A and Reb D can be increased by using ethanol for so-called "after-precipitation". For that purpose, at the end of crystallization 0.5-1.0 (vol/wt), preferably 0.5-0.8 (vol/wt), of absolute ethanol to the initial solids, was added to the mixture and the process was continued for another 2-3 hours. The yield and purity of the product from an extract with 48.7% of Reb A content are summarized in TABLE 22.

TABLE 20

| Ethanol, % | Ratio ethanol to solid, vol/wt | Purity of product at different Reb B content, % (Reb D content was 0.4%) | | | |
|---|---|---|---|---|---|
| | | 0% | 0.4% | 0.8% | 1.1% |
| 81.0 | 2.5 | 98.7 | 98.5 | 98.2 | 97.9 |
| | 3.0 | 98.9 | 98.7 | 98.4 | 98.1 |
| | 3.5 | 99.2 | 98.9 | 98.6 | 98.4 |
| 83.0 | 2.5 | 98.1 | 98.2 | 98.0 | 97.7 |
| | 3.0 | 98.5 | 98.4 | 98.2 | 97.9 |
| | 3.5 | 98.8 | 98.6 | 98.4 | 98.2 |
| 85.0 | 2.5 | 97.7 | 97.6 | 97.4 | 97.2 |
| | 3.0 | 98.2 | 97.9 | 97.6 | 97.4 |
| | 3.5 | 98.5 | 98.2 | 97.8 | 97.6 |
| 87.0 | 2.5 | 96.3 | 97.2 | 96.6 | 96.4 |
| | 3.0 | 97.5 | 97.6 | 97.4 | 97.0 |
| | 3.5 | 97.9 | 97.9 | 97.6 | 97.2 |
| 88.0 | 2.5 | 96.1 | 95.9 | 95.5 | 95.1 |
| | 3.0 | 97.3 | 97.1 | 96.4 | 95.8 |
| | 3.5 | 97.7 | 97.5 | 97.2 | 96.8 |
| 90.0 | 2.5 | 94.6 | 94.1 | 92.3 | 90.5 |
| | 3.0 | 96.3 | 95.8 | 92.8 | 91.2 |
| | 3.5 | 97.3 | 96.8 | 93.7 | 91.9 |

TABLE 21

| Ethanol, % | Ratio ethanol to solid, vol/wt | Purity of product at different content of Reb D, % (Reb B content was 0.1%) | | | |
|---|---|---|---|---|---|
| | | 0.5% | 1.2% | 1.7% | 2.6% |
| 81.0 | 2.5 | 98.7 | 98.0 | 97.5 | 97.1 |
| | 3.0 | 98.9 | 98.3 | 98.0 | 97.4 |
| | 3.5 | 99.2 | 98.5 | 98.2 | 97.7 |
| 83.0 | 2.5 | 98.1 | 97.7 | 97.3 | 97.0 |
| | 3.0 | 98.5 | 98.1 | 97.8 | 97.4 |
| | 3.5 | 98.8 | 98.4 | 98.0 | 97.6 |
| 85.0 | 2.5 | 97.7 | 97.5 | 97.1 | 96.8 |
| | 3.0 | 98.2 | 97.8 | 97.6 | 97.1 |
| | 3.5 | 98.5 | 98.1 | 97.8 | 97.2 |
| 87.0 | 2.5 | 96.3 | 96.2 | 95.8 | 94.2 |
| | 3.0 | 97.5 | 97.3 | 96.7 | 96.1 |
| | 3.5 | 97.9 | 97.6 | 97.4 | 96.9 |
| 88.0 | 2.5 | 96.1 | 95.7 | 95.2 | 93.7 |
| | 3.0 | 97.3 | 97.1 | 96.5 | 95.6 |
| | 3.5 | 97.7 | 97.4 | 97.0 | 96.6 |
| 90.0 | 2.5 | 94.6 | 94.2 | 93.5 | 93.0 |
| | 3.0 | 94.8 | 94.8 | 93.9 | 93.3 |
| | 3.5 | 95.7 | 95.4 | 94.4 | 93.5 |

TABLE 22

| Additional ethanol volume, vol/wt to solids | Yield and purity of RebA at different concentrations of ethanol (ratio of ethanol to extract = 1:3.5, wt/vol.) | | | | | | | |
|---|---|---|---|---|---|---|---|---|
| | 85% | | 86% | | 87% | | 88% | |
| | Yield, % | RebA, % | Yield, % | RebA, % | Yield, % | RebA, % | Yield, % | RebA, % |
| 0 | 29.5 | 98.5 | 30.6 | 98.3 | 32.7 | 97.9 | 33.3 | 97.8 |
| 0.5 | 31.4 | 98.5 | 31.6 | 98.2 | 33.4 | 97.9 | 33.8 | 97.6 |
| 0.6 | 32.3 | 98.2 | 32.7 | 98.2 | 34.3 | 97.8 | 34.7 | 97.6 |
| 0.7 | 33.5 | 97.9 | 33.9 | 97.7 | 35.4 | 97.6 | 35.9 | 97.5 |
| 0.8 | 34.1 | 97.9 | 35.2 | 97.7 | 36.3 | 97.6 | 36.7 | 97.4 |
| 0.9 | 34.3 | 97.8 | 35.4 | 97.6 | 36.7 | 97.5 | 37.4 | 97.4 |
| 1.0 | 34.5 | 97.8 | 35.7 | 97.5 | 36.9 | 97.4 | 37.7 | 97.2 |

To produce high purity Reb A the process can be carried out at 30-50° C. without a cooling stage. However, when this was done, although the purity of Reb A was higher the process resulted in a lower yield of the product. The quality of the product increased at higher washing temperatures. The results obtained using 3.5 volumes of 85% ethanol to one part of extract after 24 hours, and with and without an after-precipitation stage, are summarized in TABLE 23.

TABLE 23

| Temperature, °C. | Yield, % | | Content of Reb A | |
|---|---|---|---|---|
| | Without after-precipitation | With after-precipitation (0.8 vol. EtOH) | Without after-precipitation | With after-precipitation (0.8 vol. EtOH) |
| 22.0 | 29.6 | 33.5 | 98.2 | 98.5 |
| 30.0 | 28.7 | 32.8 | 98.4 | 98.6 |
| 35.0 | 27.5 | 32.2 | 98.7 | 98.9 |
| 40.0 | 27.0 | 31.4 | 98.8 | 99.2 |
| 45.0 | 25.4 | 28.9 | 99.0 | 99.4 |
| 50.0 | 24.3 | 25.6 | 99.2 | 99.5 |

Reb A, Reb B and Reb D contents in extract were 51.3, 0.2% and 0.7%, respectively.

When the content of Reb A in the final product was less than 97% mainly due to high content of Reb B and/or Reb D, the product was additionally washed with an aqueous solution of ethanol. The Reb A obtained after precipitation was suspended in the ethanol-water mixture at room temperature for 30-40 min. After homogeneous suspension was obtained the temperature was increased up to 35-50° C., preferably 38-42° C., and agitated for about 10-20 hours, preferably 12-15 hours, and then at 10-25° C., preferably 20-22° C., for about 3-20 hours, preferably 5-10 hours. The proportion of Reb A and ethanol was 1.0:2.0-1.0:5.0 (wt/vol.), preferably 1.0:2.5-4.0 (wt/vol.). The ethanol concentration was between 85-93%, and preferably 88-90%.

If the purity of Reb A was lower than 97% due to a high content of Stevioside, the product was washed with absolute ethanol in the same manner as described above for Reb B and Reb D contaminated product. The proportion of Reb A and ethanol was 1.0:2.0-1.0:5.0 (wt/vol.), and preferably 1.0:2.5-4.0 (wt/vol.)

Figure 7:
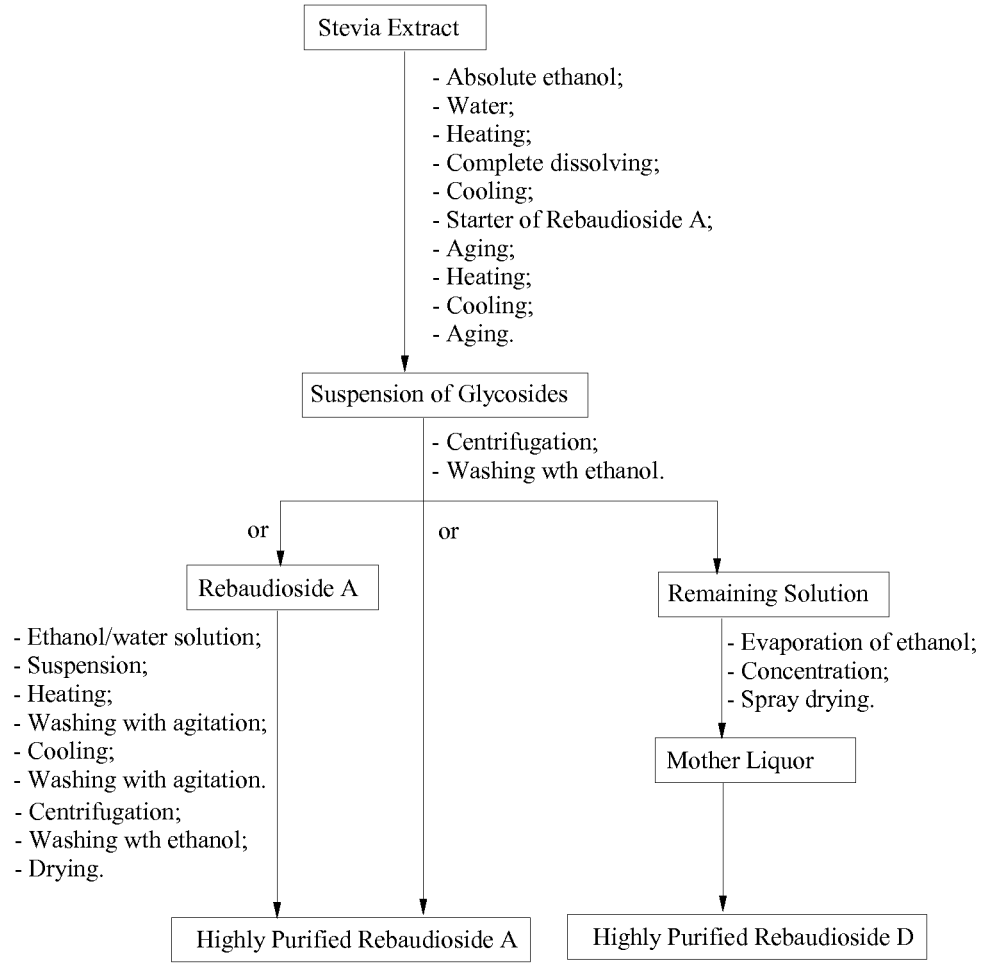
FIG. 7 is a diagram illustrating a one-stage purification scheme of Rebaudioside A using ethanol-water systems, followed by the isolation of Rebaudioside D from a remaining solution.
Figure 8:
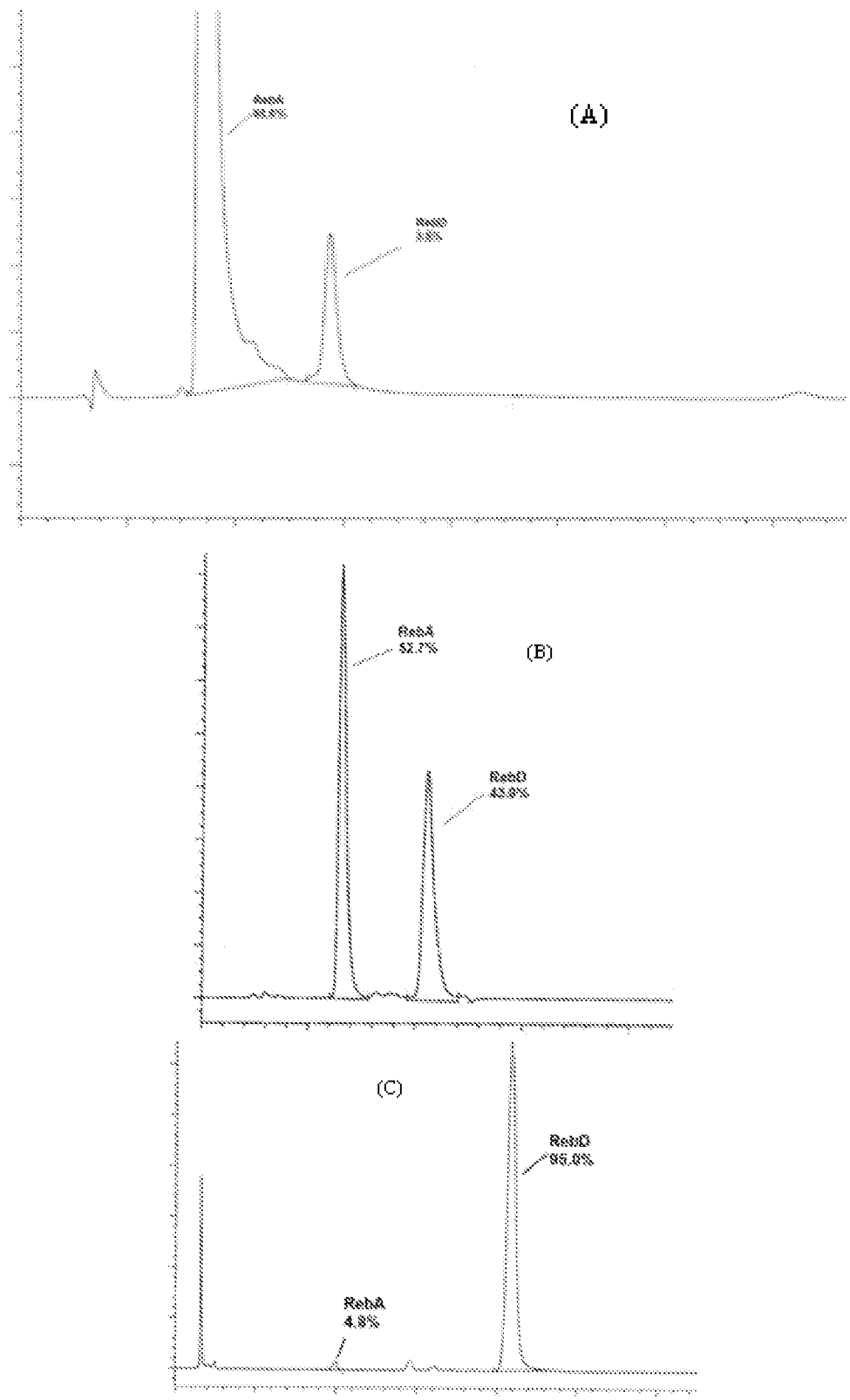
FIG. 8 includes HPLC charts of Rebaudioside D at various stages of purification.

FIG. 7 illustrates a one-stage purification scheme of Reb A using ethanol-water systems.

The purification of Reb D from the Reb A crystals with a relatively high content of Reb D was carried out using various schemes.

According to the one scheme, the material with a relatively high content of Reb D was mixed with an ethanol-water solution and incubated at 45-65° C., preferably 50-55° C., for 2-6 hours, preferably 3-4 hours, with agitation. Then, the mixture was cooled down to room temperature for 1-3 hours, preferably 0.5-1 hour. The precipitate with a high content of Reb D was separated by filtration or centrifugation.

The preferable ratio of solids to aqueous ethanol solution was 1:5, (wt/vol.), and the optimum concentration of ethanol was 78% (TABLE 24).

TABLE 24

| Ethanol, % | Ratio ethanol to solid, vol/wt | Purity of RebA, % | RebD in crystals, % |
|---|---|---|---|
| 75.0 | 4.0 | 98.5 | 18.4 |
| | 5.0 | 99.2 | 18.6 |
| | 6.0 | 99.4 | 18.6 |

TABLE 24-continued

| Ethanol, % | Ratio ethanol to solid, vol/wt | Purity of RebA, % | RebD in crystals, % |
|---|---|---|---|
| 77.0 | 4.0 | 98.4 | 18.7 |
| | 5.0 | 99.1 | 20.1 |
| | 6.0 | 99.2 | 20.3 |
| 78.0 | 4.0 | 98.4 | 19.2 |
| | 5.0 | 99.2 | 22.0 |
| | 6.0 | 99.4 | 22.1 |
| 79.0 | 4.0 | 98.1 | 19.0 |
| | 5.0 | 98.8 | 19.7 |
| | 6.0 | 99.0 | 19.8 |
| 80.0 | 4.0 | 98.0 | 17.3 |
| | 5.0 | 98.4 | 17.9 |
| | 6.0 | 98.9 | 18.2 |
| 82.0 | 4.0 | 97.7 | 15.2 |
| | 5.0 | 98.1 | 15.8 |
| | 6.0 | 98.7 | 16.4 |

The process can be completed in a shorter time period when an aqueous solution of ethanol is used, however even pure ethanol may be efficient.

In another embodiment an initial material containing 95.6% of Reb A and 3.5% Reb D (FIG. 8a) was mixed with 3.5 volumes of 78.0% ethanol, the mixture was boiled for 10-15 min and undissolved crystals were separated by hot filtration. The output of the crystals was in the range of 6.0-8.0%, with 52-53.0% and 43-45.0% of Reb A and Reb D (FIG. 8b) contents, respectively.

For the further purification the precipitate was suspended in 50% ethanol at the ratio of 1:2 (wt/vol.) and at 30-40° C., preferably 33-37° C., and maintained for 2-15 hours, preferably 10-12 hours, with agitation. The suspension was filtered and dried. The yield of precipitate with about 20-22.0% of Reb A and 80-82% of Reb D was in the range of 34-36.0%. Up to five volumes of aqueous ethanol can be applied at this stage. The concentration of ethanol can be in the range of 10-80%, preferably 45-50%.

The precipitate can be subjected to similar treatment to obtain a product with less than 5.0% of Reb A and about 95% of Reb D content (FIG. 8c). The yield of the product was around 58-60%.

Figure 9:
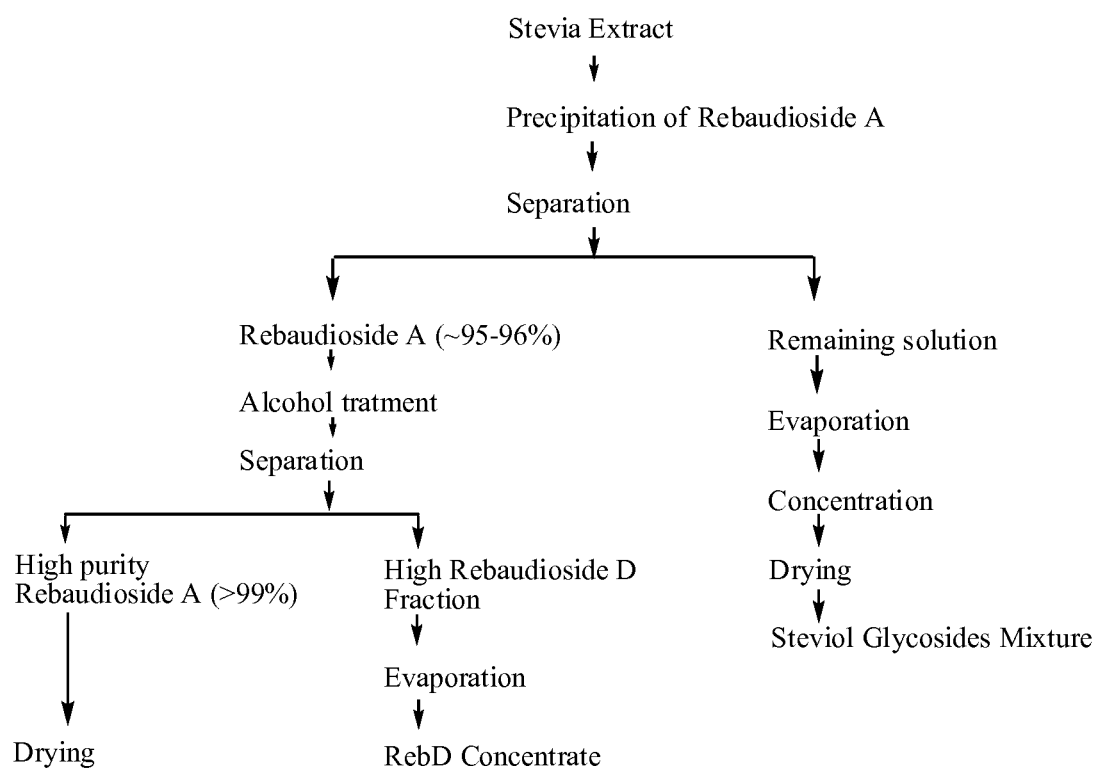
FIG. 9 is a diagram illustrating a purification scheme of Rebaudioside D along with Rebaudioside A, using ethanol at the first stage.

According to another scheme which is presented schematically in FIG. 9, the Reb A crystals with a relatively high Reb D content, obtained after precipitation with aqueous ethanol solution, were mixed with methanol or aqueous methanol solution and the mixture was maintained at 20-40° C., preferably 20-25° C., for 0.5-6 hours, preferably 1-2 hours. The ratio of methanol solution or pure methanol to solids was in the range of 1.5-10, preferably 1:2 (wt/vol.) to 1:3 (wt/vol.). At a higher ratio the resulting solution contains a higher level of Reb A. In all of the examples the purity of Reb A in the "washed" crystals was not less than 98% (TABLE 25).

Generally ambient temperature is sufficient to wash out Reb D; however, higher temperatures may also be used.

The precipitate was separated by filtration or centrifugation, washed with about two volumes of anhydrous methanol, and dried.

TABLE 25

| Methanol, % | Ratio methanol to solid, vol/wt | Purity of RebA crystals, % | RebD in filtrate, % dry basis |
|---|---|---|---|
| 100.0 | 2.0 | 98.3 | 24.5 |
| | 3.0 | 98.9 | 28.3 |
| | 5.0 | 99.3 | 22.2 |

TABLE 25-continued

| Methanol, % | Ratio methanol to solid, vol/wt | Purity of RebA crystals, % | RebD in filtrate, % dry basis |
|---|---|---|---|
| 80.0 | 2.0 | 98.5 | 19.7 |
|  | 3.0 | 98.9 | 20.6 |
|  | 5.0 | 99.3 | 18.6 |
| 70.0 | 2.0 | 98.5 | 19.7 |
|  | 3.0 | 99.1 | 21.5 |
|  | 5.0 | 99.4 | 20.2 |
| 60.0 | 2.0 | 98.7 | 25.5 |
|  | 3.0 | 99.3 | 28.6 |
|  | 5.0 | 99.5 | 22.3 |
| 50.0 | 2.0 | 98.7 | 25.9 |
|  | 3.0 | 99.4 | 29.3 |
|  | 5.0 | 99.5 | 22.4 |
| 40.0 | 2.0 | 98.7 | 21.6 |
|  | 3.0 | 99.4 | 24.5 |
|  | 5.0 | 99.5 | 20.4 |
| 30.0 | 2.0 | 98.8 | 21.9 |
|  | 3.0 | 99.5 | 24.8 |
|  | 5.0 | 99.6 | 20.8 |
| 20.0 | 2.0 | 98.4 | 20.3 |
|  | 3.0 | 98.5 | 21.5 |
|  | 5.0 | 98.5 | 20.1 |

The purity of Reb A was 98.3-99.6%.

The remaining solution and washed liquid were combined and methanol was removed by distillation.

For the further purification of Reb D the filtrate was concentrated and mixed with anhydrous methanol and the resulting mixture was intensively agitated for at least 24 hours. For the precipitation of Reb D the preferable concentration of solids in initial solution was in the range of 33-37% (TABLE 26).

TABLE 26

| Concentration of Remaining solution, % | Ratio of solids to methanol, wt/vol. | Purity of RebD, % |
|---|---|---|
| 20.0 | 1:2.0 | 42.4 |
| 25.0 | 1:2.0 | 47.3 |
| 30.0 | 1:2.0 | 55.4 |
| 33.0 | 1:2.0 | 84.4 |
| 35.0 | 1:2.0 | 84.3 |
| 37.0 | 1:2.0 | 83.6 |
| 40.0 | 1:2.0 | 75.1 |
| 45.0 | 1:2.0 | No precipitate |
| 50.0 | 1:2.0 | No precipitate |

The ratio of solid to liquid may vary in the range of 1:2.0-1:7.0 (wt/vol.), preferably 1:2.0-3.5 (wt/vol.). However at a higher ratio the output of precipitate decreases (TABLE 27).

TABLE 27

| Concentration of Remaining solution, % | Ratio of solids to methanol, wt/vol. | Purity of RebD, % |
|---|---|---|
| 33.5 | 1:1.5 | 73.5 |
| 33.5 | 1:2.0 | 84.5 |
| 33.5 | 1:2.5 | 84.7 |
| 33.5 | 1:3.0 | 84.7 |
| 33.5 | 1:3.5 | 83.5 |
| 33.5 | 1:4.0 | 75.7 |
| 33.5 | 1:5.0 | 71.6 |
| 33.5 | 1:6.0 | 64.3 |
| 33.5 | 1:7.0 | 61.1 |

The precipitate was separated by filtration or centrifugation, washed with about two volumes of anhydrous methanol and dried.

In order to obtain higher purity Reb D the precipitate was suspended in a methanol-water mixture. A concentration of methanol between 30-80% can be used, preferably 55-60%, which results in a higher purity and yield of Reb D. The suspension was heated up to 40-65° C., preferably 50-55° C., and maintained for 10-15 minutes, cooled down to 20-22° C. and maintained for an additional 1.0 to 4.0 hours, preferably 1.0-1.5 hours, with agitation. The preferred ratio of solid to methanol solution was from 1:3.0 to 1:5.0 (wt/vol.), more preferably 1:3.0 (TABLE 28).

TABLE 28

| Methanol, % | Solids to methanol ratio, wt/vol. | Purity of RebD, % |
|---|---|---|
| 30.0 | 1:2.0 | 98.5 |
|  | 1:3.0 | 98.7 |
|  | 1:4.0 | 98.6 |
|  | 1:5.0 | 98.3 |
| 40.0 | 1:2.0 | 97.6 |
|  | 1:3.0 | 98.5 |
|  | 1:4.0 | 98.5 |
|  | 1:5.0 | 98.2 |
| 50 | 1:2.0 | 98.6 |
|  | 1:3.0 | 98.9 |
|  | 1:4.0 | 98.8 |
|  | 1:5.0 | 98.5 |
| 60 | 1:2.0 | 98.8 |
|  | 1:3.0 | 99.1 |
|  | 1:4.0 | 99.1 |
|  | 1:5.0 | 98.3 |
| 70 | 1:2.0 | 98.4 |
|  | 1:3.0 | 98.6 |
|  | 1:4.0 | 98.5 |
|  | 1:5.0 | 97.5 |

The suspension was filtered and dried as described above.

The purity of Reb D was around 98-99% at the optimum conditions.

Alternatively the remaining solution was concentrated to 60-70% of solids, and after adding 1% (from total solids) Reb D crystals as a starter, it was allowed to incubate for 48-72 hours. The resulting mass was then mixed with 2-3 volumes of anhydrous methanol, and then the suspension was stirred at ambient temperature for 2-3 hours.

The crystals were separated and dried as described above. The purity of Reb D was about 84-85%.

The further purification of the material was carried out according to the procedure described above using a 55-60% methanol solution.

Purification of Reb D from Remaining Solution After Isolation of Reb A

In another embodiment of the present invention the isolation and purification of Rebaudioside D was developed from solutions remaining after the isolation of Rebaudioside A from *Stevia* extract. Rebaudioside A purification was carried out by a one-, two- or three-stage process, by treatment with various alcohols or alcohol-water systems at various temperatures and times. The isolation of a high Rebaudioside D fraction from remaining solutions was developed using chromatographic separation techniques at various conditions. From crude preparations, Rebaudioside D was purified by treatment with alcohol or alcohol-water solutions at various temperatures and times. Low Rebaudioside D fractions were combined, evaporated, deionized, decolorized, concentrated, and dried to produce a mixture of steviol glycosides with not less than 95% purity.

Commercial *Stevia* extract containing Stevioside at 24.3%, Reb A at 62.1%, Reb C at 8.8%, Reb D at 1.6%, Reb B at 0.2%, Reb E at 0.6%, Reb F at 1.0%, Steviolbioside at 0.10%, and Dulcoside A at 1.3%, with 87.9% of total steviol glycosides content, was used as a starting material in most of the experiments for this embodiment.

Stevia extract was dissolved in a methanol-water solution at 10-70° C., preferably 55-60° C., for about 10-30 min, preferably 15-20 min, and then at 15-40° C., preferably 20-22° C., for about 10-15 minutes, and maintained for 2-4 hours, preferably 1-2 hours, with agitation. When the temperature reached 20-22° C., 1-2% of highly purified Reb A was added to the reaction mixture as a starter to initiate crystallization. The proportion of extract and methanol-water solution depended on the content of Reb A and other compounds including minor glycosides, and was between 1.0:2.5-1.0:10.0 (wt/vol.), preferably 1.0:3.0-5.0, (wt/vol.).

The concentration of methanol may be between 75-99%, preferably 82-88%. The content of Reb A and Reb D in the final product ranges from 97% to 99% and 0.2-0.4% respectively at optimum and near to optimum conditions. Therefore this embodiment is useful for the one-stage production of highly purified Reb A.

The data are summarized in TABLES 29 and 30.

TABLE 29

| Methanol, % | Extract:methanol ratio, wt/vol. | Steviol glycosides, % | | | | Yield, % |
| | | St | RebC | RebA | RebD | |
|---|---|---|---|---|---|---|
| 75 | 1:3.0 | 0.2 | 0.5 | 99.2 | 0.1 | 14.4 |
| 78 | -"- | 0.3 | 0.5 | 99.1 | 0.1 | 19.6 |
| 80 | -"- | 0.4 | 0.6 | 98.8 | 0.2 | 21.2 |
| 82 | -"- | 0.5 | 0.7 | 98.6 | 0.2 | 32.2 |
| 85 | -"- | 0.6 | 0.6 | 98.5 | 0.3 | 40.3 |
| 87 | -"- | 0.5 | 0.8 | 98.4 | 0.3 | 42.5 |
| 88 | -"- | 0.8 | 1.0 | 97.9 | 0.3 | 44.4 |
| 89 | -"- | 1.0 | 1.0 | 97.7 | 0.3 | 45.6 |
| 90 | -"- | 1.1 | 1.2 | 97.3 | 0.4 | 48.1 |
| 95 | -"- | 1.8 | 1.6 | 96.2 | 0.4 | 48.6 |
| 99 | -"- | 3.2 | 4.7 | 91.4 | 0.7 | 49.3 |

TABLE 30

| Methanol, % | Extract:methanol ratio, wt/vol. | Steviol glycosides, % | | | | Yield, % |
| | | St | RebC | RebA | RebD | |
|---|---|---|---|---|---|---|
| 85 | 1:5.0 | 0.1 | 0.4 | 99.4 | 0.1 | 40.5 |
| 85 | 1:4.0 | 0.2 | 0.5 | 99.2 | 0.1 | 41.8 |
| 85 | 1:3.5 | 0.4 | 0.6 | 98.8 | 0.2 | 42.3 |
| 85 | 1:3.0 | 0.6 | 0.6 | 98.5 | 0.3 | 42.5 |
| 85 | 1:2.5 | 0.8 | 1.3 | 97.5 | 0.4 | 44.3 |
| 85 | 1:2.0 | 3.6 | 4.3 | 91.3 | 0.8 | 47.7 |

Under optimum conditions the major quantity of Reb D remains in the filtrate. In crystals the quantity of Reb D is increasing with a decrease of methanol solution to solids ratio. At the same time the purity of Reb A is increasing in cases of more diluted methanol solutions and higher ratios of methanol to extract.

The yield of Reb A from Stevia extract of various qualities after treatment with 85% methanol at 1:3 wt/vol. ratio is summarized in TABLE 31.

TABLE 31

| RebA content in initial extract, % | Yield of RebA, % |
|---|---|
| 42.0-43.0 | 19.0-23.0 |
| 45.0-46.0 | 25.0-28.0 |
| 50.0-54.0 | 28.0-31.0 |
| 55.0-59.0 | 33.0-37.0 |
| 60.0-62.0 | 38.0-43.0 |

The precipitate was separated by filtration or centrifugation, washed with about two volumes of absolute methanol and dried.

The yield of crystals may be increased using methanol for after-precipitation. For that purpose at the end of crystallization, 0.5-1.0% (vol/wt), preferably 0.7-0.8% (vol/wt), of absolute methanol to the initial solids, was added to the reaction mixture and the process was continued for another 20-30 minutes.

The yield and purity of the crystals and remaining solution for the extract with 62.1% Reb A and 1.6% Reb D content are summarized in TABLE 32.

TABLE 32

| Methanol, % | Extract:methanol ratio, wt/vol. | Additional methanol volume, vol/wt to solids | Steviol glycosides, % | | | | Yield, % |
| | | | St | RebC | RebA | RebD | |
|---|---|---|---|---|---|---|---|
| 85.0 | 1:3.0 | 0 | 0.6 | 0.6 | 98.5 | 0.3 | 42.5 |
| 85.0 | 1:3.0 | 0.2 | 0.6 | 0.7 | 98.4 | 0.3 | 43.4 |
| 85.0 | 1:3.0 | 0.5 | 0.6 | 1.0 | 98.1 | 0.3 | 44.3 |
| 85.0 | 1:3.0 | 0.7 | 0.6 | 1.2 | 98.0 | 0.2 | 46.9 |
| 85.0 | 1:3.0 | 0.8 | 0.5 | 1.4 | 98.0 | 0.1 | 47.4 |
| 85.0 | 1:3.0 | 0.9 | 0.5 | 1.6 | 97.7 | 0.2 | 47.5 |
| 85.0 | 1:3.0 | 1.0 | 0.5 | 1.9 | 97.4 | 0.2 | 47.5 |

When the content of Reb A in the crystals was less than 97%, the precipitate was washed with additional volumes of anhydrous methanol.

The process of purification of Reb A using methanol can be carried out in continuous conditions in fully automated systems.

Figure 10:
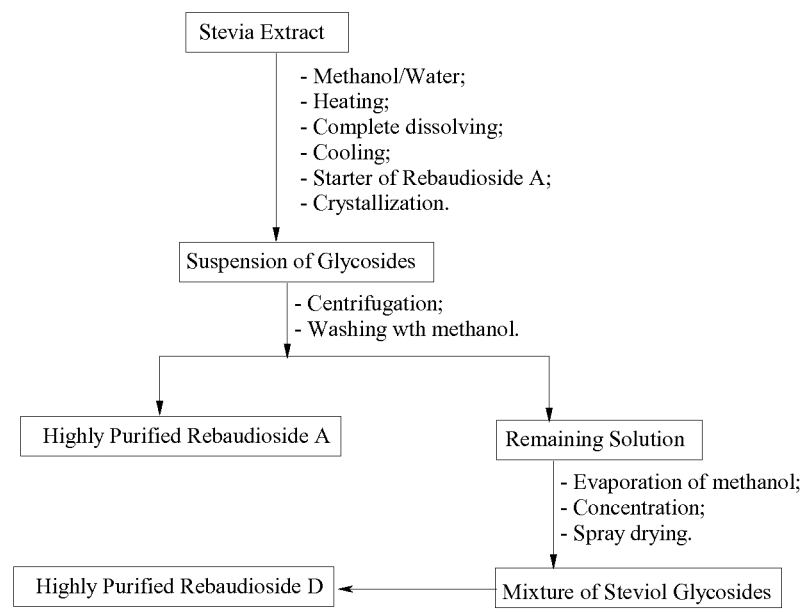
FIG. 10 is a diagram illustrating the isolation of Rebaudioside D from a remaining solution after the one-stage purification of Rebaudioside A, using methanol as solvent.

The one-stage purification scheme of Reb A using methanol as a sole solvent, and isolation of Reb D from the remaining solution, is presented in FIG. 10.

In another embodiment of the invention, a Reb A purification scheme was similarly developed using ethanol as a solvent.

The purification of Reb D from the remaining solution was developed using various schemes.

The remaining solution, after isolation of Reb A using ethanol or methanol solutions, was evaporated and passed through a series of eight consecutively connected columns with the rate equal to 1.0 bed volume per 1 hour. Each column was packed with 200 mL of specific polar macroporous polymeric resin. Upon completion of the adsorption the resin was washed with 5 volumes of water.

Desorption of the adsorbed steviol glycosides was carried out separately from each column with 50-52% ethanol at $BV=1.0\text{-}2.0\ hour^{-1}$.

Similarly to *Stevia* extract in the case of applying 9.5-10.0% of total solids to the total volume of resin, the content of Stevioside and Reb C is higher in the initial columns and decreases in the following ones, while the content of Reb A and Reb D increases from the first column to the eighth column. The data shows that affinity of Stevioside to the adsorbent is significantly higher than that of Reb A. The contents of Reb E, Reb F, and Dulcoside A decrease from the first to the final column. The steviol glycoside composition adsorbed on each column under conditions described above is presented in TABLE 33.

Thus, if the elution of each column is carried out separately a steviol glycoside mixture with a high content of Stevioside, Reb A, or Reb D and controlled amounts of other glycosides can be obtained.

The decrease in total solids subjected to the chromatographic treatment results in an increase of Reb D content in the final column. However the quantity has to be enough for steviol glycosides to reach the final column. The correlation between glycosides quantity subjected to the chromatographic separation and Reb D content in the final eighth column is shown in TABLE 34. Each column was packed with 200 mL of macroporous resin.

TABLE 34

| Quantity of Glycosides, g | Reb D content in the eight column, % |
|---|---|
| 160.0 | 6.7 |
| 152.0 | 19.6 |
| 150.0 | 21.3 |
| 145.0 | 25.8 |

Similarly to *Stevia* extract, in the case of higher quantities which exceed the adsorption capacity of the resins, the resulting "water fraction" contains high amounts of Reb D and Reb A and lower amounts of Stevioside. The yield of total product was in the range of 73-75%. Reb D and Reb A

TABLE 33

| Column | Steviol glycosides, % | | | | | | | | | Quantity, g |
|---|---|---|---|---|---|---|---|---|---|---|
| | St | RebA | RebC | RebD | RebB | RebE | RebF | StBio | DulA | |
| Initial mixture | 51.9 | 21.6 | 20.5 | 2.8 | 0.4 | 0.4 | 1.2 | 0.1 | 1.1 | 152.0 |
| First | 53.3 | 16.5 | 24.7 | 0.8 | 0.4 | 0.7 | 1.8 | 0.3 | 1.5 | 18.6 |
| Second | 53.6 | 17.0 | 24.0 | 0.8 | 0.4 | 0.7 | 1.8 | 0.2 | 1.5 | 17.2 |
| Third | 53.3 | 21.0 | 21.3 | 0.4 | 0.5 | 0.5 | 1.7 | 0.1 | 1.2 | 16.2 |
| Fourth | 51.8 | 23.0 | 20.5 | 1.0 | 0.5 | 0.4 | 1.5 | 0.1 | 1.2 | 14.3 |
| Fifth | 48.5 | 26.3 | 20.2 | 1.5 | 0.5 | 0.4 | 1.1 | 0.1 | 1.4 | 12.1 |
| Sixth | 39.8 | 34.7 | 19.6 | 2.7 | 0.5 | 0.3 | 1.0 | 0.0 | 1.4 | 12.3 |
| Seventh | 32.6 | 40.1 | 18.1 | 6.7 | 0.6 | 0.2 | 1.0 | 0.0 | 0.7 | 11.5 |
| Eighth | 20.9 | 48.5 | 9.0 | 19.6 | 0.4 | 0.2 | 0.8 | 0.0 | 0.6 | 7.8 |
| Yield, % | 70.7 | 98.0 | 79.2 | 90.4 | 94.5 | 89.4 | 92.6 | 87.9 | 88.9 | 72.3 |

However, when the adsorbent is saturated the ratio of various glycosides becomes practically the same in all columns.

recovery was around 90%. The content of steviol glycosides in different columns and water fractions is shown in TABLE 35.

TABLE 35

| Column | Steviol glycosides, % | | | | | | | | | Quantity, g |
|---|---|---|---|---|---|---|---|---|---|---|
| | St | RebA | RebC | RebD | RebB | RebE | RebF | StBio | DulA | |
| Initial mixture | 51.9 | 21.6 | 20.5 | 2.8 | 0.4 | 0.4 | 1.2 | 0.1 | 1.1 | 170.0 |
| First | 51.0 | 18.9 | 24.5 | 0.9 | 0.4 | 0.7 | 1.8 | 0.3 | 1.5 | 18.2 |
| Second | 51.2 | 20.0 | 23.6 | 0.6 | 0.4 | 0.7 | 1.8 | 0.2 | 1.5 | 17.5 |
| Third | 51.2 | 23.3 | 21.0 | 0.4 | 0.6 | 0.5 | 1.7 | 0.1 | 1.2 | 15.4 |
| Fourth | 50.4 | 24.4 | 21.0 | 0.4 | 0.6 | 0.4 | 1.5 | 0.1 | 1.2 | 14.5 |
| Fifth | 50.0 | 25.2 | 20.8 | 0.7 | 0.5 | 0.4 | 1.1 | 0.1 | 1.2 | 14.4 |
| Sixth | 49.0 | 25.5 | 20.4 | 1.5 | 0.5 | 0.3 | 1.1 | 0.1 | 1.6 | 12.3 |
| Seventh | 47.8 | 26.8 | 20.1 | 2.3 | 0.2 | 0.2 | 1.0 | 0.1 | 1.5 | 12.4 |
| Eighth | 36.1 | 31.8 | 18.6 | 11.2 | 0.2 | 0.1 | 1.0 | 0.0 | 1.0 | 11.5 |
| Water fraction | 17.5 | 36.8 | 16.2 | 27.6 | 0.5 | 0.6 | 0.7 | 0.0 | 0.5 | 7.7 |
| Yield, % | 72.0 | 90.9 | 81.5 | 90.3 | 86.5 | 86.0 | 90.0 | 96.8 | 93.5 | 72.9 |

The content of Reb A and Reb D in the "water fraction" decreases with the increase of total solids subjected to the purification, as shown in TABLE 36 for an eight column system, wherein each column is packed with 200 mL macroporous resin.

TABLE 36

| Total solid, g | Steviol glycosides, % | | | | |
|---|---|---|---|---|---|
| | St | RebC | RebA | RebD | Others |
| Initial solution | 51.9 | 20.5 | 21.6 | 2.8 | 3.2 |
| 180.0 | 30.7 | 19.6 | 31.9 | 13.3 | 4.5 |
| 170.0 | 17.5 | 16.2 | 36.8 | 27.6 | 1.9 |
| 167.0 | 17.3 | 13.9 | 38.5 | 28.7 | 1.6 |
| 164.0 | 17.0 | 13.2 | 39.2 | 29.3 | 1.3 |

The content of Reb D in the solutions increased up to 70-80% after chromatographic re-treatment, which is described above.

The desorption of steviol glycosides, and further treatment and purification of Reb D and other glycosides, was carried out in a similar manner as that described above for the Stevia extract.

Figure 11:
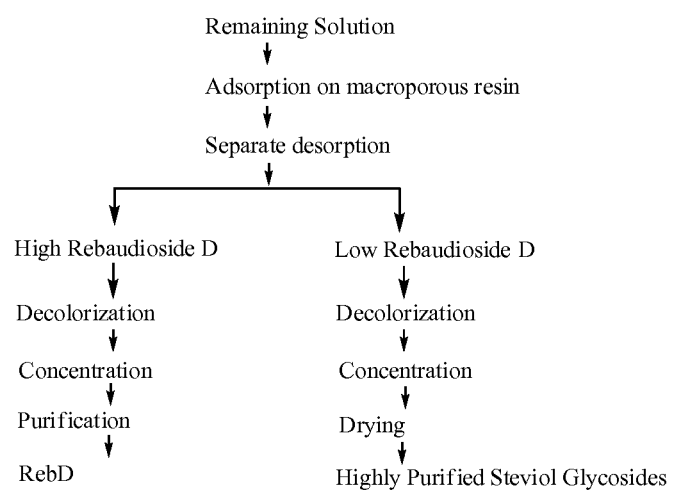
FIG. 11 is a diagram illustrating the separation of high and low Rebaudioside D fractions from part of a remaining solution after isolation of Rebaudioside A adsorbed on macroporous resin.
Figure 12:
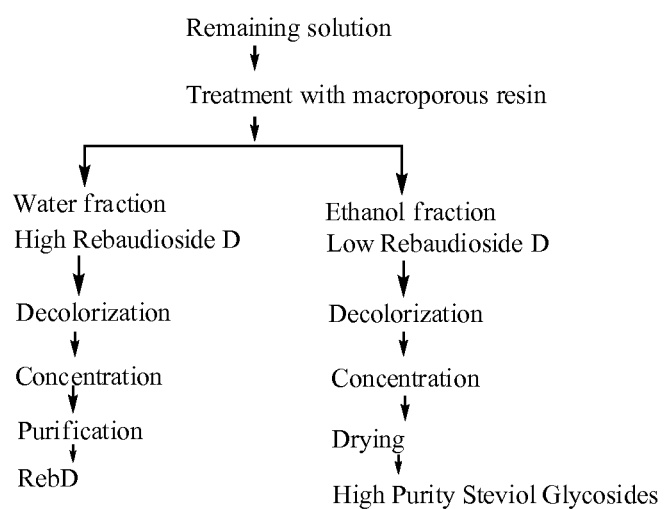
FIG. 12 is a diagram illustrating the separation of high and low Rebaudioside D fractions from part of a remaining solution after isolation of Rebaudioside A which was not adsorbed on macroporous resin (i.e. the water fraction).

Flow charts of chromatographic isolation of high Reb D fractions from the remaining solution after isolation of Reb A using methanol treatment are presented in FIGS. 11 and 12.

The purity of Reb D was about 98-99% at the optimum conditions.

The purity of the mixture of steviol glycosides after isolation of Reb D was not less than 95%.

Purification of Reb D from Remaining Solution After Isolation of Reb A and Steviol Glycosides In another embodiment of the present invention, the isolation and purification of Rebaudioside D was developed from remaining solutions which were obtained after the isolation of Rebaudioside A, and a highly purified mixture of other steviol glycosides, from a Stevia extract.

Rebaudioside A isolation from a steviol glycoside mixture containing a high amount of Rebaudioside D was carried out by a one-, two- or three-stage process using treatment with various alcohols or alcohol-water systems, at various temperatures and times. The combined remaining solution was treated with an alcohol solution, separated and dried to produce a highly purified mixture of steviol glycosides. The isolation of a high Rebaudioside D fraction from the remaining solutions was developed using chromatographic separation techniques. From the crude preparations, Rebaudioside D was purified by treatment with alcohol or alcohol-water solutions at various temperatures and times.

Commercial Stevia extract containing Stevioside at 21.4%, Reb A at 54.6%, Reb C at 7.7%, Reb D at 1.4%, Reb B at 0.2%, Reb E at 0.5%, Reb F at 0.9%, Steviolbioside at 0.10%, and Dulcoside A at 1.1%, with 91.2% of total steviol glycosides content, was used as starting material in most of the experiments of this embodiment.

Isolation of Reb A from Stevia extract using ethanol or methanol solutions was carried out as described above.

The content of steviol glycosides in the remaining solution (mother liquor) was: Stevioside (48.2%), Reb A (14.7%), Reb C (11.1%), Reb D (1.4%), Reb B (0.2%), Reb E (1.2%), Reb F (1.8%), Steviolbioside (0.4%), Dulcoside A (1.9%), and Rubusoside (1.4%). The total steviol glycosides content was 82.3%.

In order to produce a highly purified mixture of steviol glycosides the spray-dried mother liquor was dissolved in absolute methyl alcohol and maintained at 60-75° C., preferably 65-70° C., for about 5-20 min, preferably 5-10 min, and then at 10-35° C., preferably 20-25° C., for about 6-24 hours, preferably 9-12 hours, with agitation. The proportion of powdered mother liquor and methanol was 1.0:2.5 to 1.0:10.0 (wt/vol.), preferably 1.0:3.0 to 1.0:5.0 (wt/vol.). The precipitate was separated by filtration or centrifugation.

A higher methanol to solid ratio resulted in a higher purity of steviol glycosides and a higher content of Stevioside. At the lower amounts of methanol the yield of steviol glycosides was higher; however, the purity was lower. In contrast, higher amounts of methanol resulted in a higher purity and lower yield of the product. Different quantities of methanol resulted in different ratios of steviol glycosides (TABLE 37).

TABLE 37

| Solid to methanol, wt/vol. | Steviol glycosides, % | | | | | | | | | | TSG, % | Yield, % |
|---|---|---|---|---|---|---|---|---|---|---|---|---|
| | St | RebA | RebC | RebD | RebB | RebE | RebF | StBio | DulA | Rub | | |
| Initial mixture | 48.2 | 14.7 | 11.1 | 1.4 | 0.2 | 1.2 | 1.8 | 0.4 | 1.9 | 1.4 | 82.3 | — |
| 1:2.5 | 69.3 | 19.3 | 4.6 | 0.5 | 0.1 | 0.6 | 0.7 | 0.3 | 0.4 | 0.5 | 96.3 | 59.5 |
| 1:3.0 | 69.6 | 21.0 | 4.6 | 0.5 | 0.1 | 0.6 | 0.7 | 0.3 | 0.3 | 0.4 | 98.1 | 48.2 |
| 1:3.5 | 72.5 | 19.1 | 4.3 | 0.5 | 0.1 | 0.6 | 0.6 | 0.3 | 0.1 | 0.4 | 98.5 | 46.6 |
| 1:4.0 | 75.8 | 16.2 | 3.9 | 0.5 | 0.1 | 0.4 | 0.6 | 0.4 | 0.4 | 0.6 | 98.9 | 45.4 |
| 1:4.5 | 84.1 | 11.8 | 2.2 | 0.3 | 0.1 | 0.1 | 0.3 | 0.1 | 0.1 | 0.1 | 99.2 | 43.8 |
| 1:5.0 | 86.2 | 10.8 | 1.7 | 0.2 | 0.1 | 0.1 | 0.1 | 0.1 | 0 | 0 | 99.3 | 40.9 |
| 1:6.0 | 88.1 | 10.4 | 0.4 | 0.1 | 0.1 | 0 | 0.1 | 0.1 | 0 | 0 | 99.3 | 38.6 |
| 1:7.0 | 93.2 | 5.6 | 0.3 | 0.1 | 0.1 | 0 | 0.1 | 0.1 | 0 | 0 | 99.5 | 33.5 |

The precipitate was separated by filtration or centrifugation, washed with about two volumes of absolute methanol and dried.

The filtrate and washing liquid were combined and spray dried. The content of steviol glycosides in the filtrate after precipitation with 3.0 volumes of methanol was as follows: Reb A (15.6%), Stevioside (4.5%), Reb C (28.9%), Reb B (0.8%), Reb D (4.8%), Reb E (3.3%), Reb F (3.7%), Dulcoside A (4.2%), Steviolbioside (0.5%), and Rubusoside (2.2%). The total content of glycosides was 68.5%.

This stage may also be carried out using anhydrous ethanol or aqueous solutions of methanol and ethanol.

Purification of Reb D from the remaining solution was carried out by column chromatography using macroporous polar resins as carriers.

The remaining solution was passed through a series of six columns at a rate equal to 1.0 bed volume per 1 hour. Each column was packed with 200 mL of specific polar macroporous polymeric resin. Upon completion of the adsorption the resin was washed with 5 volumes of water.

In order to obtain higher quantity and quality of glycosides the number of the columns may be increased.

Desorption of the adsorbed steviol glycosides was carried out separately for each column with 50-52% ethanol at $BV=1.0\text{-}2.0\ \text{hour}^{-1}$.

When applying around 9.5-10.0% of total solids to the total volume of resin, all the glycosides were adsorbed on the resin. The contents of Stevioside and Reb C increased slightly in the first columns and decreased in later ones. The concentration of Reb A, Reb E, Reb F and Reb D increased gradually from the first column to the last one. Dulcoside A decreased from the first to final column. The purity of the mixture of glycosides was higher in the last columns.

The data obtained when passing the remaining solution containing 115 g of solids through the six columns, each packed with 200 mL of macroporous resin, are summarized in TABLE 38.

Reb D content in the last column increased to around 31%.

Similarly to the remaining solution obtained after isolation of Reb A, the decrease of the amount of total solids subjected to the chromatographic treatment results in an increase of Reb D content in the final column.

The correlation between total solids quantity subjected to the separation on the six columns, each with 200 mL volume, and Reb D content in the final column is summarized in TABLE 39.

TABLE 39

| Total solids, g | Reb D content in the sixth column, % |
|---|---|
| 117.0 | 23.6 |
| 115.0 | 31.3 |
| 110.0 | 39.4 |
| 107.0 | 42.9 |

In the case of higher quantities which exceed the adsorption capacity of the resins, the resulting "water fraction" contains a high amount of Reb D and Reb A and a lower content of Stevioside.

The content of steviol glycosides in different columns and the water fraction using 125 g of initial material is presented in TABLE 40.

The contents of Reb A and Reb D in the water fraction decrease with the increase in quantity of the total solids subjected to the purification. The content of steviol glycosides in the water fraction at various quantities of the initial mixture, when six columns, each packed with 200 mL of resin, were used is presented in TABLE 41.

TABLE 38

| Column | Steviol glycosides, % | | | | | | | | | | Purity, % |
|---|---|---|---|---|---|---|---|---|---|---|---|
| | St | RebA | RebC | RebD | RebB | RebE | RebF | StBio | Rub | DulA | |
| Initial mixture | 4.5 | 15.6 | 28.9 | 4.8 | 0.8 | 3.3 | 3.7 | 0.5 | 2.2 | 4.2 | 68.5 |
| First | 5.7 | 16.5 | 32.2 | 0.3 | 0.5 | 0.5 | 0.6 | 0.1 | 2.7 | 4.0 | 63.7 |
| Second | 7.2 | 20.8 | 33.9 | 0.3 | 0.5 | 0.5 | 1.9 | 0.2 | 2.3 | 3.2 | 70.8 |
| Third | 7.9 | 24.6 | 32.1 | 0.4 | 0.5 | 0.5 | 2.5 | 0.2 | 1.8 | 1.5 | 72.0 |
| Fourth | 7.2 | 29.8 | 30.6 | 0.5 | 0.5 | 0.5 | 2.8 | 0.1 | 1.2 | 1.1 | 74.3 |
| Fifth | 6.5 | 42.4 | 25.3 | 12.4 | 0.6 | 1.9 | 1.1 | 0.1 | 0.1 | 0.2 | 90.6 |
| Sixth | 2.2 | 45.9 | 6.7 | 31.3 | 0.7 | 5.4 | 4.9 | 0 | 0 | 0 | 97.1 |

TABLE 40

| Column | Steviol glycosides, % | | | | | | | | | | TSG, % |
|---|---|---|---|---|---|---|---|---|---|---|---|
| | St | RebA | RebC | RebD | RebB | RebE | RebF | StBio | Rub | DulA | |
| Initial mixture | 4.5 | 15.6 | 28.9 | 4.8 | 0.8 | 3.3 | 3.7 | 0.5 | 2.2 | 4.2 | 68.5 |
| First | 4.3 | 15.0 | 31.8 | 0.9 | 0.4 | 0.3 | 0.6 | 0.1 | 2.3 | 4.1 | 59.8 |
| Second | 4.2 | 25.7 | 31.6 | 0.9 | 0.4 | 0.3 | 0.7 | 0.2 | 2.0 | 2.8 | 68.8 |
| Third | 4.0 | 30.4 | 28.6 | 1.2 | 0.5 | 0.5 | 0.9 | 0.2 | 1.5 | 1.3 | 69.1 |
| Fourth | 3.1 | 36.9 | 28.2 | 1.6 | 0.5 | 0.7 | 1.2 | 0.1 | 1.1 | 1.1 | 74.5 |
| Fifth | 2.8 | 42.3 | 26.9 | 2.5 | 0.6 | 1.7 | 1.3 | 0.1 | 0.1 | 0.2 | 78.5 |
| Sixth | 1.3 | 46.5 | 25.7 | 6.3 | 0.7 | 2.1 | 2.4 | 0 | 0 | 0 | 85.0 |
| Water fraction | 0.9 | 18.4 | 12.4 | 26.3 | 0.9 | 4.8 | 4.7 | 0 | 0 | 0 | 68.4 |

The content of Reb D in the solutions increased up to 70-80% after chromatographic re-treatment, which is described above.

TABLE 41

| Total solid, g | Steviol glycosides, % | | | | |
|---|---|---|---|---|---|
| | St | RebC | RebA | RebD | Others |
| Initial mixture | 4.5 | 28.9 | 15.6 | 4.8 | 17.7 |
| 121.0 | 0.9 | 11.9 | 19.3 | 31.1 | 6.1 |
| 125.0 | 0.9 | 12.4 | 18.4 | 26.3 | 10.4 |
| 128.0 | 1.4 | 12.9 | 18.1 | 22.2 | 11.9 |
| 130.0 | 1.6 | 13.3 | 17.6 | 20.8 | 12.4 |

The desorption of steviol glycosides, and further treatment and purification of Reb D and other glycosides, was developed similarly to the methodology described above for the Stevia extract and remaining solution obtained after isolation of Reb A.

The purity of Reb D was around 98-99% at the optimum conditions.

The purity of the mixture of steviol glycosides after isolation of Reb D by a second chromatographic treatment using the same macroporous resin was not less than 95%.

Remaining solution for the purification of Reb D can be obtained by different schemes for the purification of Reb A and complex retreatment of Stevia extract. Depending on the purity of the initial extract, Reb A and minor compounds, especially Reb D and Reb B contents, the process can be carried out by a three-, two- or one-stage process. Reb D purification schemes after Reb A isolation by a one-stage process utilizing ethanol or methanol was described above. Reb D purification schemes after Reb A isolation by a three- and two-stage process is described below.

Description of the Purification of Reb D After Isolation of Reb A by a Three-Stage Process When Reb A content in the initial extract is low or Reb D and/or Reb B contents are high the three-stage process is preferred in order to prepare highly purified Reb A. In principle, by this process Reb A can be purified from almost any type of Stevia extract. For that purpose Stevia extract was dissolved in absolute ethyl alcohol and maintained at 70-90° C., preferably 80-85° C., for about 5-20 min, preferably 5-10 min, and then at 10-25° C., preferably 18-22° C., for about 6-24 hours, preferably 9-12 hours, with agitation. The proportion of extract and ethanol was 1.0:2.5 to 1.0:10.0, wt/vol., and preferably 1.0:3.0 to 1.0:5.0, wt/vol. The precipitate was separated by filtration or centrifugation.

Stevia extracts containing Stevioside (9.0-52.0%), Reb A (29.1-74.7%), Reb C (3.6-13.3%), Reb D (2.1-12.0%), Reb B (0.1-2.3%), Reb E (0.5-1.3%), Reb F (0.9-2.3%), Steviolbioside (0-0.1%), and Dulcoside A (0.1-1.5%), with 86-95% of total steviol glycosides content were used as starting material.

The higher the content of Reb A in the initial extract, the greater the amount of ethanol which is used at this stage. Higher ethanol:extract ratios result in higher purity of Reb A. If the amount of ethanol was decreased, the yield of crude Reb A was higher, but the purity was lower. In contrast, a higher amount of ethanol resulted in Reb A of higher purity but lower yield.

For this stage at least 98% ethanol is preferred. However, an ethanol-water solution can be used in a one- or two-stage purification process of Reb A, which will be discussed below.

If the extract contains more than 55% Reb A, the precipitation occurs without heating of the mixture but results in a low quality product.

Precipitation may also take place from extracts with lower than 40% Reb A content; however, the yield and quality of the final product is low and the process takes up to 20-24 hours.

The content of Reb A in the final product ranges between 75-85% and the yield depends on the Reb A content in the initial extract (TABLE 42) and the extract:ethanol ratio (TABLE 43).

TABLE 42

| RebA content in initial extract, % | Extract:Ethanol ratio, wt/vol. | Yield of crude RebA, % from initial extract | RebA content, % |
|---|---|---|---|
| 42.0-43.0 | 1:3.0 | 48.0-50.0 | 75.0-76.0 |
| 45.0-46.0 | -"- | 50.0-55.0 | 76.0-77.0 |
| 50.0-53.0 | -"- | 55.0-60.0 | 77.0-79.0 |
| 55.0-59.0 | -"- | 71.0-72.0 | 80.0-81.0 |
| 60.0-62.0 | -"- | 75.0-76.0 | 81.0-83.0 |

The precipitate was separated by filtration or centrifugation and washed with about one volume of absolute ethanol. The filtrate and washed liquid were combined and spray dried.

The typical compositions of the crystals and mother liquor in this stage are summarized in TABLE 44.

For further purification, the precipitate with about 75-83% of Reb A content was completely dissolved in the ethanol-water mixture by heating at 80-85° C. for 30-40 min with continuous agitation.

TABLE 43

| RebA content in initial extract, % | Extract:Ethanol ratio, wt/vol. | Yield of crude RebA, % from initial extract | RebA content, % |
|---|---|---|---|
| 52.6 | 1:2.0 | 58.2 | 72.1 |
| -"- | 1:2.5 | 57.6 | 75.4 |
| -"- | 1:3.0 | 56.4 | 79.8 |
| -"- | 1:3.5 | 54.3 | 80.1 |
| -"- | 1:4.0 | 53.1 | 81.2 |
| -"- | 1:4.5 | 52.7 | 82.3 |
| -"- | 1:5.0 | 52.0 | 82.6 |
| -"- | 1:6.0 | 49.8 | 82.9 |
| -"- | 1:7.0 | 47.4 | 83.5 |
| -"- | 1:8.0 | 44.1 | 83.9 |
| -"- | 1:9.0 | 38.2 | 84.5 |
| -"- | 1:10.0 | 34.4 | 85.1 |

TABLE 44

| | Steviol glycosides, % | | | | | | | | |
|---|---|---|---|---|---|---|---|---|---|
| Product | St | RebA | RebC | RebD | RebB | RebE | RebF | StBio | DulA |
| Crystals | 5-10.0 | 75.0-83.0 | 5-10.0 | 0.2-2.5 | <1.0 | <1.0 | 5-10.0 | <0.5 | <0.5 |
| Mother liquor | 55-67.0 | 14-19.0 | 9-15.0 | 1.5-3.5 | 0-1.5 | 0.2-1.5 | 0.2-4.0 | 0-0.4 | 0.7-2.0 |

The obtained solution was cooled to 20-25° C. and pure Reb A was added in the amount of 1-2% from solids. The suspension was cooled further to a temperature of 14-15° C., and maintained for 12-14 hours with slow agitation. Then, 0.5-1.5, vol/wt, preferably 0.7-1.0, vol/wt, of absolute ethanol to the initial solids was added to the crystallization mixture. Reb A continued to crystallize for another 12-14 hours.

The precipitate was separated by filtration or centrifugation and washed with about one volume of absolute ethanol. The purity of Reb A in this stage was 95-96% with a yield of 75-77%.

The filtrate and wash liquid were combined, spray dried and used for the purification of Reb D as described above for remaining solutions.

The purity of Reb A increased at lower concentrations and larger amounts of ethanol.

The process is preferably carried out without drying of intermediate crude Reb A, as the solubility of the product and purification efficiency decreases significantly after drying. In the case of dried material, ethanol with lower concentrations must be applied, which results in lower yields of product. The concentration of ethanol can be between 70-90%, preferably 75-85%. The ratio of solid to liquid may vary in the range of 1:2.0-1:5.0, wt/vol., preferably 1:2.2-3.5, wt/vol. At higher concentrations of ethanol, use of a higher ratio is preferred and vice versa. The optimum concentration of ethanol in this stage was 80.5% and the best ratio of solid to ethanol solution was 1:2.3, wt/vol. (TABLE 45; TABLE 46).

TABLE 45

| Ethanol concentration, % | Crude RebA:ethanol ratio, wt/vol. | Yield of Product, % | RebA content, % |
|---|---|---|---|
| 70.0 | 1:3 | 32-34 | 99.2 |
| 71.0 | -"- | 32-34 | 99.0 |
| 72.0 | -"- | 33-35 | 98.8 |
| 73.0 | -"- | 36-37 | 98.5 |
| 74.0 | -"- | 44-46 | 98.2 |
| 75.0 | -"- | 50-53 | 97.9 |
| 76.0 | -"- | 52-54 | 97.5 |
| 77.0 | -"- | 56-59 | 97.3 |
| 78.0 | -"- | 60-62 | 97.2 |
| 79.0 | -"- | 63-66 | 96.9 |
| 80.0 | -"- | 69-70 | 96.7 |
| 80.5 | -"- | 71-72 | 96.4 |
| 81.0 | -"- | 73-74 | 96.1 |
| 81.5 | -"- | 75-76 | 96.1 |
| 82.0 | -"- | 76-78 | 96.0 |
| 83.0 | -"- | 76-79 | 96.0 |
| 85.0 | -"- | 81-82 | 95.8 |
| 86.0 | -"- | 82-83 | 95.6 |
| 87.0 | -"- | 82-85 | 95.6 |
| 88.0 | -"- | 84-89 | 95.5 |
| 89.0 | -"- | 85-89 | 95.2 |
| 90.0 | -"- | 87-90 | 95.0 |
| 91.0 | -"- | 91-92 | 93.1 |

TABLE 46

| Ethanol concentration, % | Crude RebA:ethanol ratio, wt/vol. | Yield of RebA, % | RebA content, % |
|---|---|---|---|
| 80.5 | 1:5.0 | 50-55 | 96.9 |
| 80.5 | 1:4.0 | 59-60 | 96.6 |
| 80.5 | 1:3.5 | 67-68 | 96.5 |
| 80.5 | 1:3.0 | 71-72 | 96.4 |
| 80.5 | 1:2.65 | 72-73 | 96.4 |
| 80.5 | 1:2.5 | 73-74 | 96.4 |
| 80.5 | 1:2.4 | 74-75 | 96.4 |
| 80.5 | 1:2.3 | 75-77 | 96.3 |
| 80.5 | 1:2.2 | 77-78 | 94.7 |
| 80.5 | 1:2.0 | 77-78 | 94.5 |

The typical compositions of the crystals and mother liquor in this stage are summarized in TABLE 47.

TABLE 47

| | Steviol glycosides, % | | | | | | | | |
|---|---|---|---|---|---|---|---|---|---|
| Product | St | RebA | RebC | RebD | RebB | RebE | RebF | StBio | DulA |
| Crystals | <1.5 | >95.0 | <2.0 | <1.5 | <0.5 | <0.5 | <1.0 | <0.2 | <0.3 |
| Mother liquor | 18-30.0 | 45-55.0 | 18-25.0 | 0.5-4.0 | 0-1.5 | 0.2-1.0 | 1.0-7.0 | 0-0.5 | 0.2-3.0 |

Preparation of high purity Reb D was carried out similarly to the other types of remaining solutions.

Reb A with purity of 95-96% obtained at the second stage of purification was subjected to the re-crystallization in order to obtain a product with purity not less than 97%. The Reb A was completely dissolved in the ethanol-water mixture by heating at 80-85° C. for 30-40 min with continuous agitation. To increase the dissolution rate in some cases the Reb A may be dissolved in the solutions with lower concentrations of ethanol and, after complete dissolution, the remaining amount of ethanol can be added.

The obtained solution was cooled to 20-25° C. and pure Reb A was added in the amount of 1-2% from solids. The suspension continued to cool until 14-15° C., and maintained for 12-14 hours with slow agitation. Then, 0.5-1.5, vol/wt, preferably 0.7-1.0, vol/wt, of absolute ethanol to the initial solids, was added to the mixture, and crystallization continued for another 12-14 hours.

The precipitate was separated by filtration or centrifugation, washed with about one volume of absolute ethanol and dried. The purity of Reb A in this stage was in the range of 97.2-99.7% with a yield up to 86%.

The filtrate and wash liquid were combined and spray dried.

The quality of product increased at lower concentrations and larger amounts of ethanol.

It is preferable to carry out the process without drying the initial material, as the solubility of the product and purification efficiency decrease significantly after drying. In case of dried material, ethanol with lower concentrations has to be applied, which resulted in lower yields of product. The concentration of ethanol can be between 70-82%, preferably 75-80%. The ratio of solid to liquid may vary in the range of 1:2.0-1:5.0, wt/vol., preferably 1:2.5-3.5, wt/vol. At higher concentrations of ethanol, use of a higher ratio is preferred, and vice versa. The optimum concentration of ethanol in this stage was 77.7% and the best ratio of solid to ethanol solution was 1:3.0-3.5, wt/vol. (TABLE 48; TABLE 49; TABLE 50).

TABLE 48

| Ethanol concentration, % | Crude RebA:ethanol ratio, wt/vol. | Yield of RebA, % | RebA content, % |
|---|---|---|---|
| 70.0 | 1:3 | 46-47 | 99.7 |
| 71.0 | -"- | 48-50 | 99.7 |
| 72.0 | -"- | 57-58 | 99.6 |
| 73.0 | -"- | 65-66 | 99.1 |
| 74.0 | -"- | 70-71 | 99.0 |
| 75.0 | -"- | 79-80 | 98.9 |
| 76.0 | -"- | 79-80 | 98.8 |
| 77.0 | -"- | 80-81 | 98.8 |
| 78.0 | -"- | 82-83 | 98.2 |
| 79.0 | -"- | 82-83 | 98.0 |
| 80.0 | -"- | 82-84 | 97.7 |
| 80.5 | -"- | 84-85 | 97.4 |
| 81.0 | -"- | 84-85 | 97.3 |
| 81.5 | -"- | 84-85 | 97.2 |
| 82.0 | -"- | 85-86 | 97.2 |

TABLE 49

| Ethanol concentration, % | Crude RebA:ethanol ratio, wt/vol. | Yield of RebA, % | RebA content, % |
|---|---|---|---|
| 76.5 | 1:3 | 78-80 | 98.8 |
| 77.0 | -"- | 80-81 | 98.8 |
| 77.1 | -"- | 80-81 | 98.8 |
| 77.2 | -"- | 80-81 | 98.8 |
| 77.3 | -"- | 80-81 | 98.7 |
| 77.4 | -"- | 80-81 | 98.7 |
| 77.5 | -"- | 80-81 | 98.7 |
| 77.6 | -"- | 80-81 | 98.6 |
| 77.7 | -"- | 82-83 | 98.5 |
| 77.8 | -"- | 82-83 | 98.3 |
| 77.9 | -"- | 82-83 | 98.2 |
| 78.0 | -"- | 82-83 | 98.2 |

Final yields of highly purified Reb A from various types of extracts are summarized in TABLE 51.

The typical compositions of the final product and mother liquor in this stage are summarized in TABLE 52.

TABLE 50

| Ethanol concentration, % | Crude RebA:ethanol ratio, wt/vol. | Yield of RebA, % | RebA content, % |
|---|---|---|---|
| 77.7 | 1:5.0 | 71-72 | 99.6 |
| 77.7 | 1:4.0 | 74-75 | 99.1 |
| 77.7 | 1:3.5 | 82-83 | 98.7 |
| 77.7 | 1:3.0 | 82-83 | 98.5 |
| 77.7 | 1:2.65 | 83-84 | 97.6 |
| 77.7 | 1:2.5 | 85-86 | 97.4 |
| 77.7 | 1:2.4 | 85-86 | 97.4 |

TABLE 51

| RebA content in initial extract, % | Yield of RebA at precipitation stage from initial extract, % | Yield of RebA at crystallization stage from initial extract, % | Yield of RebA at recrystallization stage from initial extract (Final yield), % | Recovery of RebA from initial extract, % |
|---|---|---|---|---|
| 42.0-43.0 | 48.0-50.0 | 37-39 | 31-32 | 72-73 |
| 45.0-46.0 | 50.0-55.0 | 41-43 | 34-35 | 73-74 |
| 50.0-53.0 | 55.0-60.0 | 44-45 | 36-38 | 74-75 |
| 55.0-59.0 | 71.0-72.0 | 48-49 | 44-45 | 76-77 |
| 60.0-62.0 | 75.0-76.0 | 50-51 | 46-48 | 77-78 |

TABLE 52

| Product | Steviol glycosides, % | | | | | | | | |
|---|---|---|---|---|---|---|---|---|---|
| | St | RebA | RebC | RebD | RebB | RebE | RebF | StBio | DulA |
| Final product | <0.2 | >97.0 | <0.2 | <1.0 | <0.2 | <0.3 | <0.3 | <0.1 | <0.1 |
| Mother liquor | 3-8.0 | 75-87.0 | 3-8.0 | 2.0-5.0 | 0-0.5 | 0.2-1.5 | 0.5-2.0 | 0-0.5 | 0.2-1.0 |

The concentrated or spray dried filtrate was used as initial material for the purification of Reb D and a highly purified mixture of steviol glycosides, using the same methodology described for the other remaining solutions.

Figure 13:
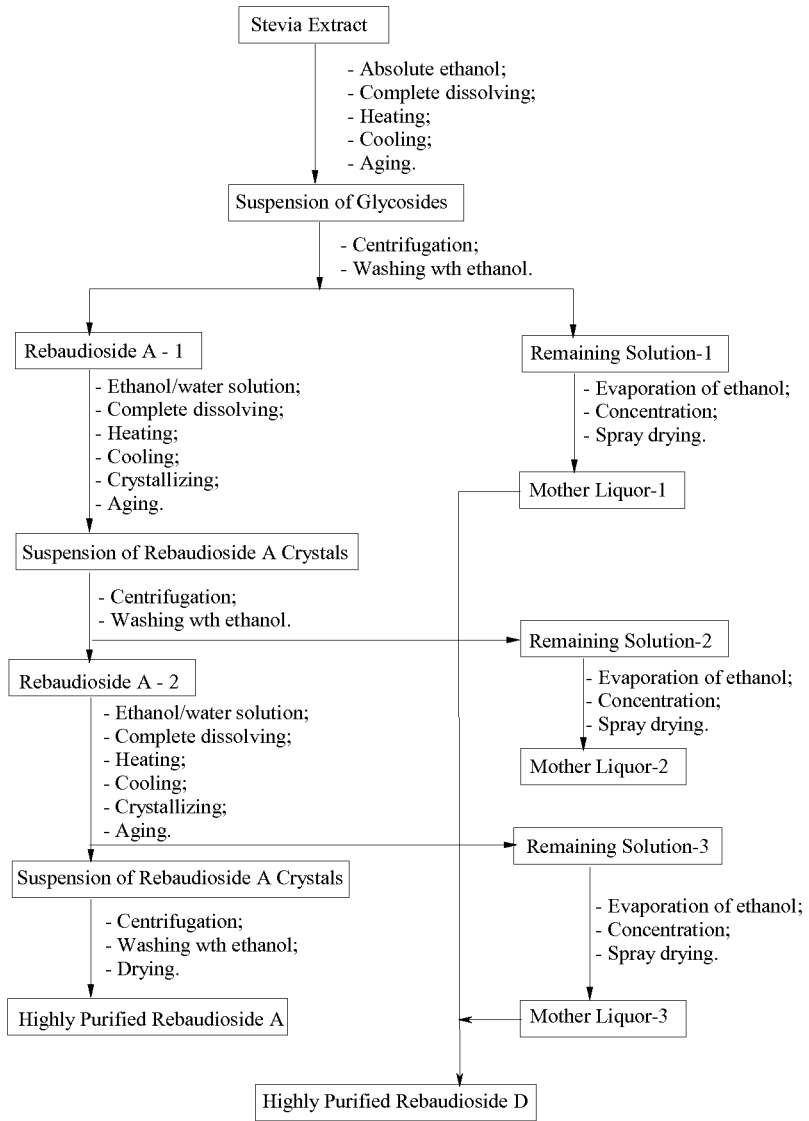
FIG. 13 is a diagram illustrating the isolation of Rebaudioside D from a remaining solution after a three-stage purification of Rebaudioside A.

The three-stage purification scheme of Reb A and isolation of Reb D fraction from remaining solutions is presented in FIG. 13.

Purification of Reb D After Isolation of Reb A by a Two-Stage Process

The first stage of purification was carried out similarly to the three-stage process described above.

When 70-75% of ethanol was used in the ratio of 1:2.5-3.0, wt/vol., during the re-crystallization stage the purity of product exceeded 98%, with about 50-53% yield in optimum cases. The purity of product increased with the decrease of ethanol concentration and increase of liquid volume. When the TSG content of initial extract is higher than 93% and the purity of crude Reb A after the first stage is 84% or more, the 78-81% of ethanol solution can be used in this stage. The ratio of crude Reb A to ethanol was 1:2.5-2.65, wt/vol., and crystallization time was 28-35 hours. The purity of product was around 98% with about 55-57% yield (TABLE 53).

TABLE 53

| Ethanol concentration, % | Yield of RebA, % Crude RebA:ethanol ratio, wt/vol. | | | RebA content, % Crude RebA:ethanol ratio, wt/vol. | | |
| --- | --- | --- | --- | --- | --- | --- |
|  | 1:2.5 | 1:2.65 | 1:3.0 | 1:2.5 | 1:2.65 | 1:3.0 |
| 70.0 | 34-36 | 33-35 | 31-32 | 98.8 | 99.1 | 99.2 |
| 71.0 | 38-39 | 37-38 | 32-34 | 98.7 | 99.0 | 99.0 |
| 72.0 | 40-42 | 37-38 | 35-37 | 98.6 | 98.7 | 98.8 |
| 73.0 | 43-44 | 41-42 | 37-39 | 98.5 | 98.4 | 98.5 |
| 74.0 | 45-46 | 44-46 | 42-44 | 98.1 | 98.2 | 98.2 |
| 75.0 | 52-55 | 50-53 | 50-51 | 97.9 | 98.1 | 97.9 |
| 76.0 | 54-56 | 53-55 | 51-53 | 97.6 | 97.7 | 97.5 |
| 77.0 | 57-61 | 57-60 | 53-55 | 97.2 | 97.4 | 97.3 |
| 78.0 | 62-64 | 61-63 | 56-58 | 96.9 | 97.3 | 97.2 |
| 79.0 | 66-68 | 64-66 | 59-61 | 96.6 | 97.0 | 96.9 |
| 80.0 | 73-75 | 70-72 | 67-69 | 96.1 | 96.6 | 96.7 |
| 81.0 | 76-78 | 73-74 | 70-72 | 95.7 | 96.2 | 96.1 |
| 82.0 | 79-80 | 76-78 | 74-75 | 95.4 | 95.7 | 96.0 |

The total final yield of highly purified Reb A from various types of extracts, using 75% ethanol solution with 1:2.65, wt/vol. ratio of solids to liquid, is summarized in TABLE 54.

TABLE 54

| RebA content in initial extract, % | Yield of RebA at precipitation stage from initial extract, % | Yield of RebA at crystallization stage from initial extract (Final product), % | Recovery of RebA from initial extract, % |
| --- | --- | --- | --- |
| 42.0-43.0 | 48.0-50.0 | 25-26 | 57-59 |
| 45.0-46.0 | 50.0-55.0 | 27-28 | 60-61 |
| 50.0-53.0 | 55.0-60.0 | 29-31 | 61-62 |
| 55.0-59.0 | 71.0-72.0 | 37-38 | 67-68 |
| 60.0-62.0 | 75.0-76.0 | 39-40 | 65-66 |

With this purification scheme, when using the same equipment as used in the three-stage process, the production capacity can be increased substantially.

The filtrate and washing liquid were combined and spray dried. The resulting material was highly suitable for the production of Reb D using chromatographic separation techniques as described above.

The typical compositions of the final product and mother liquor in this stage are summarized in TABLE 55.

TABLE 55

| Product | Steviol glycosides, % | | | | | | | | |
| --- | --- | --- | --- | --- | --- | --- | --- | --- | --- |
|  | St | RebA | RebC | RebD | RebB | RebE | RebF | StBio | DulA |
| Final product | <0.2 | >97.0 | <0.2 | <1.0 | <0.2 | <0.3 | <0.3 | <0.1 | <0.1 |
| Mother liquor | 18-27.0 | 40-48.0 | 18-28.0 | 1.0-5.0 | 0-1.0 | 0.4-1.0 | 2.0-7.0 | 0-0.5 | 0.2-3.0 |

Figure 14:
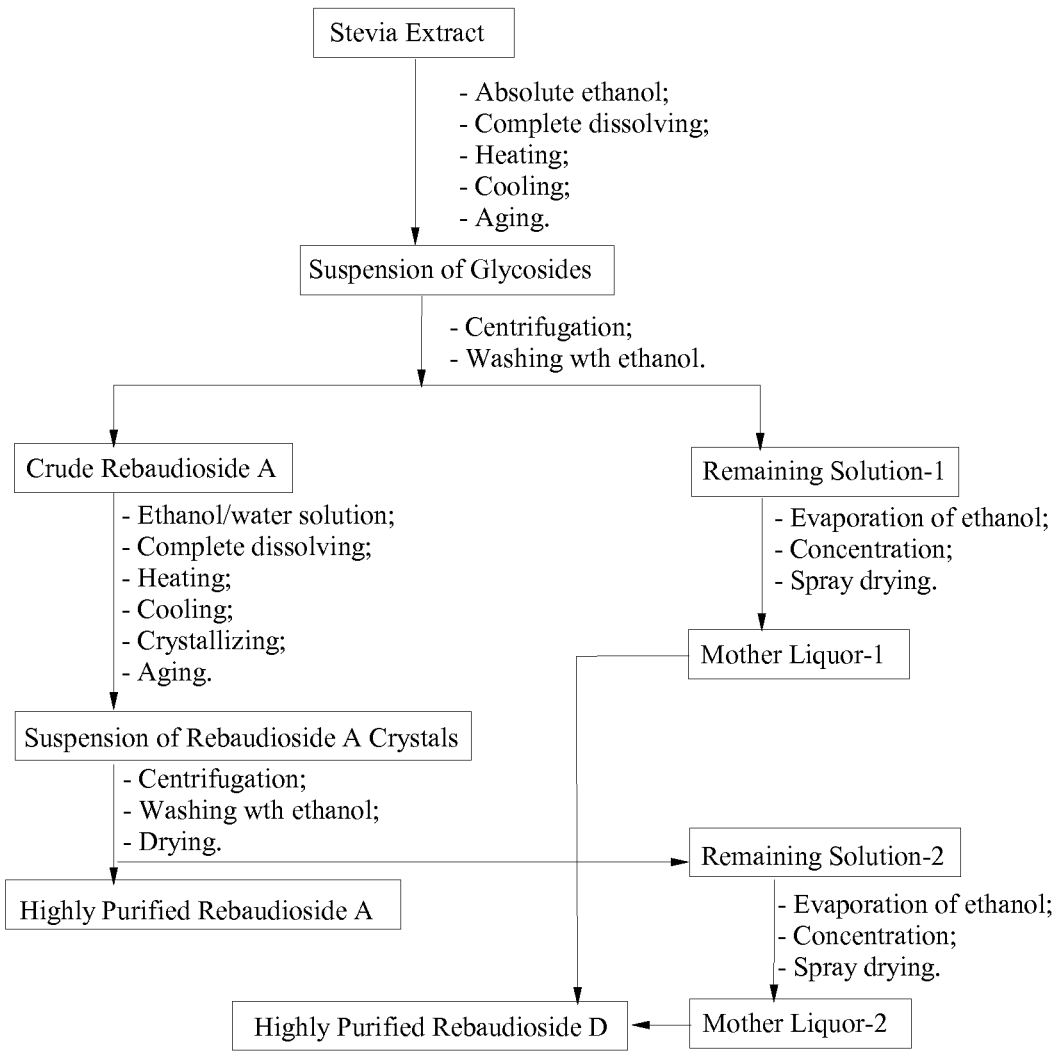
FIG. 14 is a diagram illustrating the isolation of Rebaudioside D from a remaining solution after a two-stage purification of Rebaudioside A by crystallization.

The two-stage purification scheme of Reb A, by crystallization and isolation of a high Reb D fraction, is presented in FIG. 14.

When the combined content of Reb B and Reb D in the initial extract is lower than 1.7%, the second stage can be carried out by a "washing" technique, without dissolution and crystallization of the product obtained after the first stage.

The crystals of crude Reb A obtained after precipitation were suspended in the ethanol-water mixture at room temperature for 30-40 min. After a homogeneous suspension was obtained the temperature was increased up to 35-55° C., preferably 40-45° C., and maintained for about 10-20 hours, preferably 12-15 hours, and then at 10-25° C., preferably 20-22° C., for about 3-20 hours, preferably 5-10 hours, with continuous agitation. Then, 0.5-1.5, vol/wt, preferably 0.7-1.0, vol/wt, of absolute ethanol to the initial solids, was added to the mixture and the process was continued for another 12-14 hours. The proportion of crude Reb A and ethanol depended on the content of minor compounds, especially Reb B and Reb D, and was between 1.0:2.0-1.0:5.0, wt/vol., preferably 1.0:2.5-3.5, wt/vol. The ethanol concentration was between 75-88%, and preferably between 79-85%.

The precipitate was separated by filtration or centrifugation, washed with about one volume of absolute ethanol, and dried. The purity of Reb A was greater than 97.0% with a 50-69% yield. The data obtained on crude Reb A material with 1.76% Reb D and 0.5% Reb B content is summarized in TABLE 56. The process was first carried out at 40° C. and then at 22° C. for 12 hours, adding 0.5 volume of ethanol for after-precipitation at each step.

TABLE 56

| Ethanol concentration, % | Yield of Product, % Crude RebA:ethanol ratio, wt/vol. | | | RebA content, % Crude RebA:ethanol ratio, wt/vol. | | |
|---|---|---|---|---|---|---|
| | 1:2.5 | 1:3.0 | 1:3.5 | 1:2.5 | 1:3.0 | 1:3.5 |
| 75.0 | 51-52 | 30-32 | 18-22 | 98.5 | 99.1 | 99.4 |
| 76.0 | 53-54 | 33-35 | 24-25 | 98.3 | 98.9 | 99.2 |
| 77.0 | 54-55 | 37-38 | 30-32 | 98.3 | 98.7 | 99.0 |
| 78.0 | 56-57 | 48-49 | 36-38 | 98.2 | 98.6 | 98.8 |
| 79.0 | 58-60 | 51-53 | 39-41 | 98.1 | 98.6 | 98.7 |
| 80.0 | 59-60 | 52-53 | 40-41 | 98.0 | 98.4 | 98.5 |
| 81.0 | 62-64 | 54-55 | 42-44 | 97.8 | 98.3 | 98.4 |
| 82.0 | 66-68 | 55-57 | 46-47 | 97.6 | 98.1 | 98.2 |
| 83.0 | 68-69 | 56-58 | 47-48 | 97.2 | 97.5 | 97.7 |
| 85.0 | 69-71 | 58-59 | 49-50 | 96.6 | 96.8 | 97.0 |
| 88.0 | 75-77 | 64-66 | 54-56 | 96.3 | 96.5 | 96.6 |
| 90.0 | 79-80 | 67-68 | 58-60 | 95.8 | 96.3 | 96.5 |
| 95.0 | 81-82 | 73-74 | 70-72 | 95.3 | 95.6 | 96.1 |

The ethanol precipitation of extracts with higher contents of Reb B, Reb D, Reb E and Reb F results in crude Reb A with higher contents of these compounds. Reb F and Reb E content decrease simultaneously with Reb C. The higher the content of Reb B and Reb D the lower the ethanol concentration should be, and the higher the ethanol to solids ratio. At higher concentrations of ethanol and a lower ratio of ethanol to solids, the yield of final product was higher but the purity was lower. Lower concentrations of ethanol and higher ratios result in a higher purity product with lower yield. From materials with low Reb B and Reb D content the yield and quality of product were higher. In this case, higher concentrations of ethanol can be used to increase the final yield of the product (TABLE 57, TABLE 58).

When the process was carried out without a cooling stage, the purity of Reb A was higher; however, it resulted in a lower yield of the product. The quality of the product increased at higher washing temperatures. Similar results were obtained during the process without an after-precipitation stage (TABLE 59).

TABLE 57

| Ethanol, % | Ratio ethanol to solid, vol/wt | Purity of product at different RebB content, % (RebD content was 1.1%) | | | |
|---|---|---|---|---|---|
| | | 0% | 0.2% | 0.6% | 0.9% |
| 79.0 | 2.5 | 98.1 | 98.0 | 97.9 | 97.4 |
| | 3.0 | 98.6 | 98.5 | 98.3 | 97.5 |
| | 3.5 | 98.7 | 98.5 | 98.0 | 97.7 |
| 80.0 | 2.5 | 98.0 | 98.0 | 97.7 | 97.2 |
| | 3.0 | 98.4 | 98.4 | 97.9 | 97.5 |
| | 3.5 | 98.5 | 98.5 | 98.1 | 97.8 |
| 82.0 | 2.5 | 97.6 | 97.6 | 97.4 | 97.1 |
| | 3.0 | 98.1 | 98.0 | 97.6 | 97.2 |
| | 3.5 | 98.2 | 98.2 | 97.9 | 97.0 |
| 85.0 | 2.5 | 96.6 | 96.5 | 96.2 | 95.6 |
| | 3.0 | 96.8 | 96.7 | 96.5 | 95.9 |
| | 3.5 | 97.0 | 97.0 | 96.7 | 96.3 |

TABLE 58

| Ethanol, % | Ratio ethanol to solid, vol/wt | Purity of product at different content of RebD, % (RebB content was 0.2%) | | | |
|---|---|---|---|---|---|
| | | 0.6% | 1.1% | 1.5% | 2.1% |
| 79.0 | 2.5 | 98.3 | 98.0 | 97.6 | 97.2 |
| | 3.0 | 98.5 | 98.5 | 97.8 | 97.5 |
| | 3.5 | 98.8 | 98.5 | 98.3 | 97.9 |
| 80.0 | 2.5 | 98.2 | 98.0 | 97.4 | 97.1 |
| | 3.0 | 98.4 | 98.4 | 97.9 | 97.3 |
| | 3.5 | 98.6 | 98.5 | 98.1 | 97.6 |
| 82.0 | 2.5 | 97.8 | 97.6 | 97.2 | 96.9 |
| | 3.0 | 98.2 | 98.0 | 97.6 | 97.1 |
| | 3.5 | 98.4 | 98.2 | 97.9 | 97.4 |
| 85.0 | 2.5 | 96.8 | 96.5 | 95.9 | 94.1 |
| | 3.0 | 97.2 | 96.7 | 96.4 | 94.4 |
| | 3.5 | 97.4 | 97.0 | 96.6 | 95.3 |

Thus, depending on the quality of initial material and goals of the process the optimal technological parameters can be varied to achieve the desired result.

The concentrated or spray dried filtrate was used as initial material for the purification of Reb D and a highly purified mixture of steviol glycosides using the same methodology as was described for the other remaining solutions.

Figure 15:
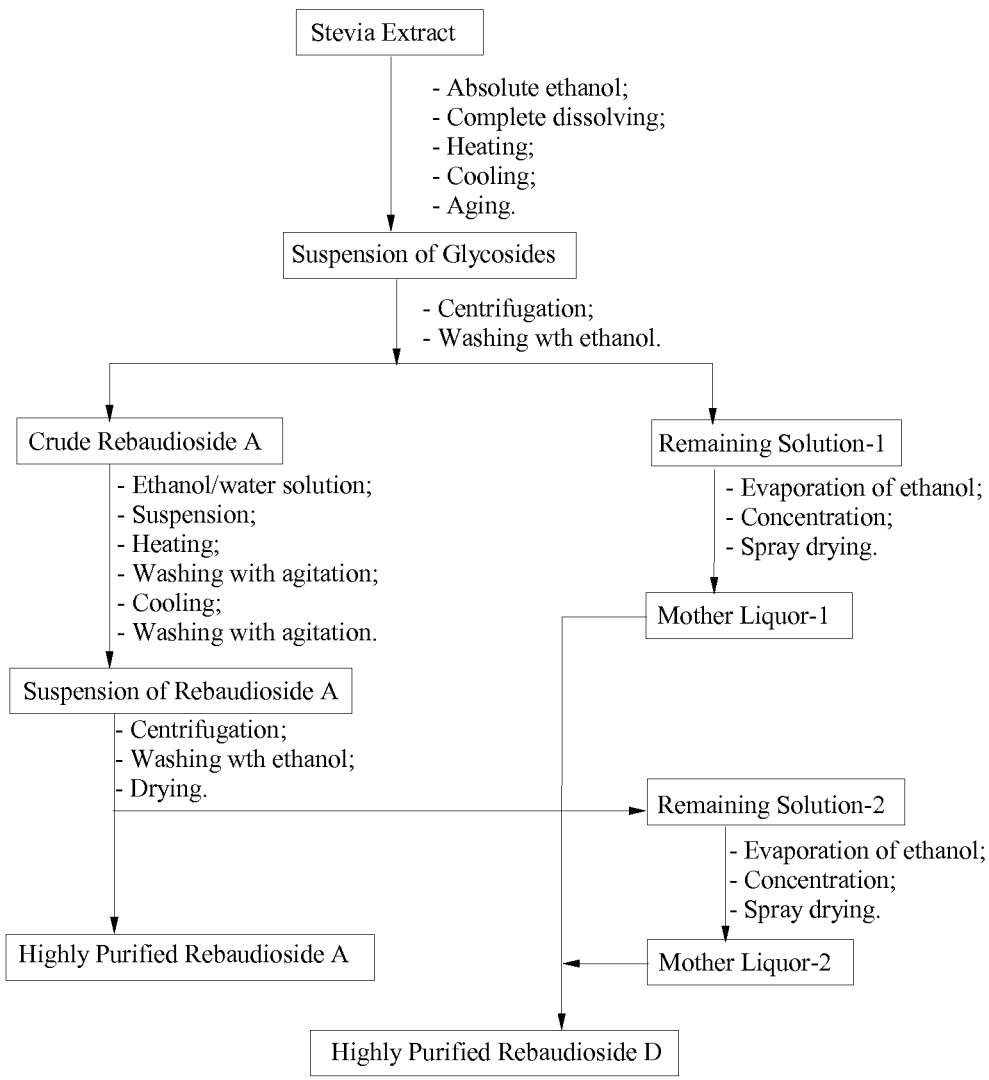
FIG. 15 is a diagram illustrating the purification of Rebaudioside D from a remaining solution after a two-stage purification of Rebaudioside A by washing.

The two-stage purification scheme of Reb A, using a "washing" technique and isolation of high Reb D fraction, is presented in FIG. 15.

TABLE 59

| Additional ethanol volume, vol/wt to solids | Quality of product washed with 82% ethanol with ratio of 1:2.5, wt/vol. | | | | | | | | | | | |
|---|---|---|---|---|---|---|---|---|---|---|---|---|
| | 22° C. | | 35° C. | | 40° C. | | 45° C. | | 50° C. | | 55° C. | |
| | A* | B** | A | B | A | B | A | B | A | B | A | B |
| 0 | 61.6 | 98.1 | 58.2 | 98.6 | 57.4 | 98.8 | 55.3 | 98.9 | 45.1 | 99.4 | 32.5 | 99.6 |
| 0.5 | 65.7 | 97.7 | 60.5 | 98.3 | 58.5 | 98.5 | 56.0 | 98.6 | 45.3 | 99.2 | 32.9 | 99.4 |
| 0.6 | 67.1 | 97.6 | 62.3 | 98.0 | 59.2 | 98.3 | 56.5 | 98.5 | 45.7 | 98.8 | 33.3 | 99.2 |
| 0.7 | 67.1 | 97.4 | 63.3 | 97.9 | 61.5 | 98.1 | 57.8 | 98.3 | 46.0 | 98.6 | 33.9 | 98.8 |
| 0.8 | 67.4 | 97.4 | 64.0 | 97.7 | 62.4 | 97.9 | 60.1 | 98.0 | 46.7 | 98.5 | 35.6 | 98.6 |
| 0.9 | 67.5 | 97.3 | 65.4 | 97.6 | 63.0 | 97.8 | 61.2 | 97.8 | 47.2 | 98.3 | 35.7 | 98.6 |
| 1.0 | 67.6 | 97.1 | 65.9 | 97.5 | 63.6 | 97.6 | 61.5 | 97.7 | 47.8 | 98.1 | 36.4 | 98.4 |

*(A), is Yield of the product, %;
**(B), is purity of the product (Reb A content), %.

Purification of Rebaudioside D After Isolation of Rebaudioside A by a One-stage Process When the Rebaudioside A content in the initial extract is not less than 40%, and the Rebaudioside D and/or Rebaudioside B combined contents are lower than 1.8%, a one-stage process can be performed in order to prepare highly purified Rebaudioside A. For that purpose *Stevia* extract was dissolved in an ethanol-water solution at 50-70° C., preferably 55-60° C., for about 10-30 min, preferably 15-20 min, and then at 15-40° C., preferably 20-22° C., for about 18-48 hours, preferably 20-24 hours, with agitation. When the temperature reached 22° C., 1-3 vol. % of highly purified Rebaudioside A was added to the reaction mixture as a starter to initiate crystallization. The proportion of extract and ethanol depended on content of minor compounds, especially Rebaudioside B and Rebaudioside D, and was between 1.0:2.0-1.0:4.0, w/v, preferably 1.0:2.5-3.5, w/v. Ethanol concentration was between 80-90%, preferably 82-88%. At lower concentrations of ethanol, a lower ratio of ethanol to solid can be used, and vice versa. At 89-90% ethanol concentrations, the purity of Rebaudioside A was more than 97.0% with yields between 13-35% (TABLE 60).

TABLE 60

Yield (Y) and purity of product (RebA), %%, at different ratio of ethanol to extract (v/w)

| EtOH, % | 1:1.75 | | 1:2.0 | | 1:2.5 | | 1:3.0 | | 1:3.5 | | 1:3.65 | | 1:4.0 | |
|---|---|---|---|---|---|---|---|---|---|---|---|---|---|---|
| | Y, % | RebA, % | Y, % | RebA, % | Y, % | RebA, % | Y, % | RebA, % | Y, % | RebA, % | Y, % | RebA, % | Y, % | RebA, % |
| 80.0 | 25.2 | 98.5 | 20.4 | 98.7 | 20.0 | 98.7 | 18.2 | 99.1 | 17.8 | 99.4 | 17.1 | 99.5 | 13.2 | 99.6 |
| 81.0 | 25.8 | 98.2 | 24.2 | 98.5 | 22.6 | 98.7 | 21.1 | 98.9 | 20.4 | 99.2 | 18.3 | 99.4 | 13.6 | 99.4 |
| 82.0 | 27.0 | 97.7 | 26.3 | 98.4 | 25.7 | 98.5 | 24.5 | 98.7 | 23.3 | 99.1 | 22.2 | 99.0 | 14.1 | 99.4 |
| 83.0 | 28.3 | 97.4 | 27.2 | 98.4 | 26.8 | 98.1 | 26.0 | 98.5 | 25.2 | 98.8 | 24.6 | 99.0 | 17.9 | 99.1 |
| 84.0 | 30.5 | 97.1 | 29.6 | 97.1 | 29.5 | 97.9 | 28.8 | 98.4 | 28.1 | 98.6 | 27.7 | 98.7 | 20.8 | 98.7 |
| 85.0 | 35.1 | 96.7 | 33.8 | 96.6 | 31.1 | 97.7 | 30.4 | 98.2 | 29.5 | 98.5 | 29.1 | 98.6 | 25.6 | 98.7 |
| 86.0 | 36.2 | 96.5 | 33.9 | 96.2 | 32.5 | 97.5 | 31.7 | 97.7 | 30.6 | 98.3 | 30.0 | 98.6 | 28.8 | 98.6 |
| 87.0 | 40.4 | 96.1 | 34.2 | 95.7 | 34.2 | 96.3 | 33.5 | 97.5 | 32.7 | 97.9 | 31.6 | 98.2 | 29.4 | 98.4 |
| 88.0 | 42.5 | 94.7 | 35.4 | 94.5 | 34.8 | 94.8 | 34.1 | 97.3 | 33.3 | 97.8 | 32.5 | 97.9 | 30.6 | 98.1 |
| 89.0 | 42.9 | 92.9 | 39.7 | 93.8 | 38.4 | 94.2 | 37.8 | 94.7 | 37.1 | 96.6 | 37.6 | 97.4 | 35.3 | 97.6 |
| 90.0 | 43.4 | 92.1 | 41.2 | 93.5 | 40.7 | 93.9 | 40.1 | 94.5 | 39.4 | 96.5 | 38.5 | 96.8 | 38.8 | 97.1 |

RebA content in the initial extract was 48.5%; RebD - 0.4%

The precipitate was separated by filtration or centrifugation, washed with about two volumes of absolute ethanol and dried. Any type of equipment which allows the separation of precipitate from liquid, such as various centrifuges or filtration systems, can be used in this stage. Different type of dryers, such as a rotary vacuum dryer, fluid bed dryer, rotary tunnel dryer or plate dryer, are suitable to produce Rebaudioside A in powder form.

If the initial extract contains a high amount of Rebaudioside B and Rebaudioside D for the purification of Rebaudioside A, lower concentrations of ethanol and a higher ratio of ethanol to the extract is used (TABLE 61; TABLE 62). Rebaudioside A content in the initial extract was 48.7%.

TABLE 61

| | Ratio ethanol | Purity of product at different RebB content, % (RebD content was 0.4%) | | | |
|---|---|---|---|---|---|
| Ethanol, % | to solid, v/w | 0% | 0.4% | 0.8% | 1.1% |
| 81.0 | 2.5 | 98.7 | 98.5 | 98.2 | 97.9 |
| | 3.0 | 98.9 | 98.7 | 98.4 | 98.1 |
| | 3.5 | 99.2 | 98.9 | 98.6 | 98.4 |
| 83.0 | 2.5 | 98.1 | 98.2 | 98.0 | 97.7 |
| | 3.0 | 98.5 | 98.4 | 98.2 | 97.9 |
| | 3.5 | 98.8 | 98.6 | 98.4 | 98.2 |
| 85.0 | 2.5 | 97.7 | 97.6 | 97.4 | 97.2 |
| | 3.0 | 98.2 | 97.9 | 97.6 | 97.4 |
| | 3.5 | 98.5 | 98.2 | 97.8 | 97.6 |
| 87.0 | 2.5 | 96.3 | 96.2 | 97.2 | 96.8 |
| | 3.0 | 97.5 | 97.6 | 97.4 | 97.0 |
| | 3.5 | 97.9 | 97.9 | 97.6 | 97.2 |

The yield of purified Rebaudioside A can be increased using ethanol for after-precipitation. For that purpose the temperature of the extract solution was adjusted to 35-45° C., preferably 37-40° C., and maintained for about 10-20 hours, preferably 12-15 hours, and then at 10-25° C., preferably 20-23° C., for about 10-20 hours, preferably 12-15 hours, with continuous agitation. Then, 0.5-1.0, v/w, preferably 0.5-0.8, v/w, of absolute ethanol to the initial solids, was added to the mixture and the process was continued for another 12-14 hours. The yields and purity of the product from an extract with a 49.3% Rebaudioside A content are summarized in TABLE 63.

TABLE 62

| | Ratio ethanol | Purity of product at different content of RebD, % (RebB content was 0.1%) | | | |
|---|---|---|---|---|---|
| Ethanol, % | to solid, v/w | 0.5% | 1.2% | 1.7% | 2.6% |
| 81.0 | 2.5 | 98.7 | 98.0 | 97.5 | 97.1 |
| | 3.0 | 98.9 | 98.3 | 98.0 | 97.4 |
| | 3.5 | 99.2 | 98.5 | 98.2 | 97.7 |
| 83.0 | 2.5 | 98.1 | 97.7 | 97.3 | 97.0 |
| | 3.0 | 98.5 | 98.1 | 97.8 | 97.4 |
| | 3.5 | 98.8 | 98.4 | 98.0 | 97.6 |
| 85.0 | 2.5 | 97.7 | 97.5 | 97.1 | 96.8 |
| | 3.0 | 98.2 | 97.8 | 97.6 | 97.1 |
| | 3.5 | 98.5 | 98.1 | 97.8 | 97.2 |
| 87.0 | 2.5 | 96.3 | 96.2 | 95.8 | 94.2 |
| | 3.0 | 97.5 | 97.3 | 96.7 | 96.1 |
| | 3.5 | 97.9 | 97.6 | 97.4 | 96.9 |

TABLE 63

Yield and purity of RebA at different concentrations of ethanol
(Ratio of ethanol to extract = 1:3.5, w/v)

| Additional ethanol volume, v/w to solids | 85% Yield, % | 85% RebA, % | 86% Yield, % | 86% RebA, % | 87% Yield, % | 87% RebA, % | 88% Yield, % | 88% RebA, % |
|---|---|---|---|---|---|---|---|---|
| 0 | 29.5 | 98.5 | 30.6 | 98.3 | 32.7 | 97.9 | 33.3 | 97.8 |
| 0.5 | 31.4 | 98.5 | 31.6 | 98.2 | 33.4 | 97.9 | 33.8 | 97.6 |
| 0.6 | 32.3 | 98.2 | 32.7 | 98.2 | 34.3 | 97.8 | 34.7 | 97.6 |
| 0.7 | 33.5 | 97.9 | 33.9 | 97.7 | 35.4 | 97.6 | 35.9 | 97.5 |
| 0.8 | 34.1 | 97.9 | 35.2 | 97.7 | 36.3 | 97.6 | 36.7 | 97.4 |
| 0.9 | 34.3 | 97.8 | 35.4 | 97.6 | 36.7 | 97.5 | 37.4 | 97.4 |
| 1.0 | 34.5 | 97.8 | 35.7 | 97.5 | 36.9 | 97.4 | 37.7 | 97.2 |

When the process was carried out without a cooling stage, the purity of Rebaudioside A was higher; however, it resulted in a lower yield of the product. The quality of the product increased at higher washing temperatures. The results obtained using 3.5 volumes of 85% ethanol to one part of extract after 24 hours, with and without after-precipitation, are summarized in TABLE 64.

TABLE 64

| Temperature, °C. | Yield, % Without after-precipitation | Yield, % With after-precipitation (0.8 vol. EtOH) | Content of RebA Without after-precipitation | Content of RebA With after-precipitation (0.8 vol. EtOH) |
|---|---|---|---|---|
| 22.0 | 29.6 | 33.5 | 98.2 | 98.5 |
| 30.0 | 28.7 | 32.8 | 98.4 | 98.6 |
| 35.0 | 27.5 | 32.2 | 98.7 | 98.9 |
| 40.0 | 27.0 | 31.4 | 98.8 | 99.2 |
| 45.0 | 25.4 | 28.9 | 99.0 | 99.4 |
| 50.0 | 24.3 | 25.6 | 99.2 | 99.5 |

RebA, RebB and RebD contents were 51.3, 0.2% and 0.7%, respectively.

When the content of Rebaudioside A in the final product was less than 97% the product was subjected to additional washing as described above.

The filtrate and wash liquid were combined and spray dried. Purification of Rebaudioside D and a high purity mixture of steviol glycosides was developed using the same methodology used for other types of remaining solutions.

The typical compositions of the final product and mother liquor in this stage are summarized in TABLE 65.

TABLE 65

| Product | Steviol glycosides, % St | RebA | RebC | RebD | RebB | RebE | RebF | StBio | DulA |
|---|---|---|---|---|---|---|---|---|---|
| Final product | <0.5 | >97.0 | <0.5 | <0.8 | <0.2 | <0.3 | <0.5 | <0.1 | <0.2 |
| Mother liquor | 45-57.0 | 15-25.0 | 15-23.0 | 0.2-3.7 | 0-0.5 | 0.4-1.5 | 1.5-5.0 | 0-0.5 | 0.2-4.0 |

The one-stage purification scheme of Rebaudioside A and the isolation of a high Rebaudioside D fraction from the remaining solution is presented in FIG. 7.

Thus, when the initial *Stevia* extract is distinguished with a high content of Rebaudioside A, the initial stage of the reprocessing may start with the purification of this main compound. The suitable technological scheme can be chosen in accordance with the content of other compounds, especially Rebaudioside B and Rebaudioside D.

The production of highly purified Rebaudioside D was carried out either from crystals of Rebaudioside A or remaining solutions.

Properties of Rebaudioside D

Figure 3:
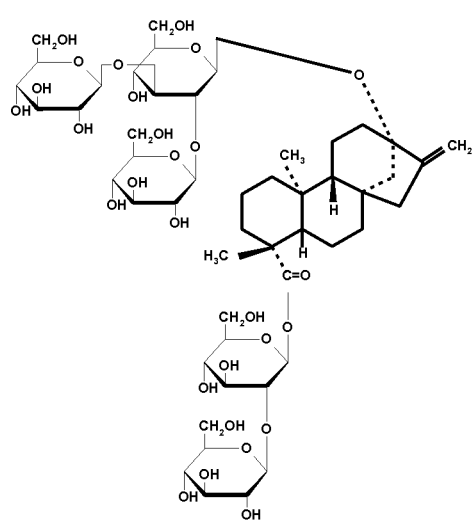
FIG. 3 shows the structure of Rebaudioside D.
Figure 16:
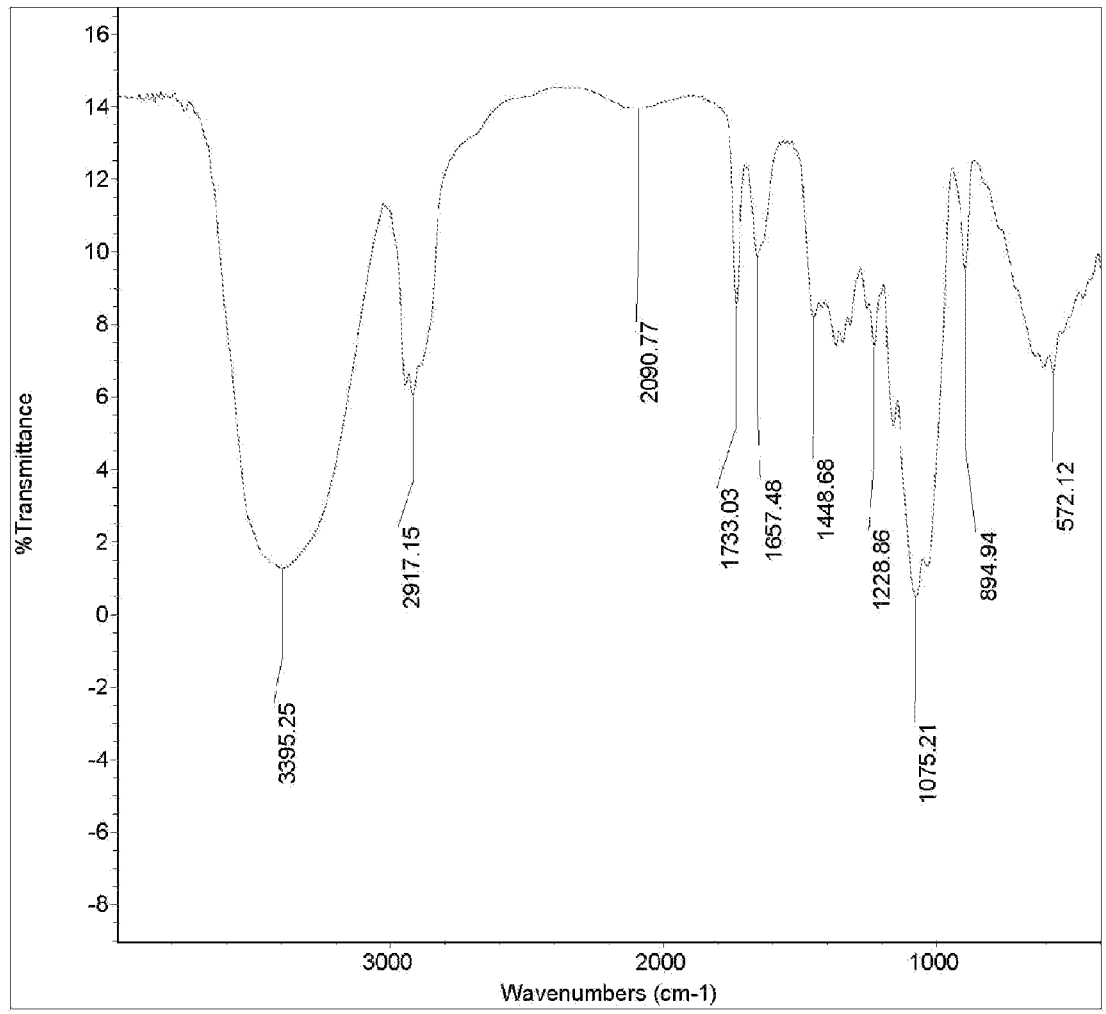
FIG. 16 is an FTIR spectrum of Rebaudioside D.

The high purity Reb D obtained in this invention, having a molecular weight of 1129.15, a molecular formula of $C_{50}H_{80}O_{28}$, and the structure presented in FIG. 3, is in the form of a white and odorless powder. The compound is about 180-200 times sweeter than sugar when compared to a 10% sucrose solution. The infrared absorption spectrum is shown in FIG. 16. Reb D exhibits a characteristic absorption maximum at around 1730 cm$^{-1}$.

Other properties of the pure Reb D compound include a melting point of 248-249° C., and a specific rotation of $[\alpha]_D^{25}$-29.5° in 50% ethanol (C=1.0). The solubility of Reb D in water is around 0.2%, and increases with an increase in temperature. Reb D precipitates upon cooling of the solution. It is highly soluble during the chromatographic separation stage and before crystallizing.

Reb D is soluble in diluted solutions of methanol, ethanol, n-propanol, and isopropanol. However, it is insoluble in acetone, benzene, chloroform, and ether.

Reb D obtained in accordance with the present invention is heat and pH-stable.

Reb D obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc. The examples which follow show representative proportions which may be employed.

Reb D as a sweetening compound may be employed as the sole sweetener, or it may be used together with other naturally occurring high intensity sweeteners such as Stevioside, Reb A, Reb B, Reb C, Reb E, Reb F, Steviolbioside, Dulcoside A, Rubusoside, mogrosides, brazzein, neohesperidin dihydrochalcone, glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, siamenoside and others.

Reb D may also be used in combination with synthetic high intensity sweeteners such as sucralose, potassium acesulfame, aspartame, alitame, saccharin, neohesperidin dihydrochalcone, cyclamate, neotame, dulcin, suosan, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

Moreover, Reb D can be used in combination with natural sweetener suppressors such as gymnemic acid, hodulcin, ziziphin, lactisole, and others. Reb D may also be combined with various umami taste enhancers. Reb D can be mixed with umami tasting and sweet aminoacids such as glutamate, aspartic acid, glycine, alanine, threonine, proline, serine, glutamate, and tryptophan.

Reb D may also be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Reb D may be combined with reduced calorie sweeteners such as D-tagatose, L-sugars, L-sorbose, L-arabinose, and others.

Reb D may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Reb D obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Reb D obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, Reb D can be used as a sweetener not only for drinks, foodstuffs, and other products dedicated for human consumption, but also in animal feed and fodder with improved characteristics.

Examples of products in which Reb D may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the sweetener obtained in this invention may be used in dry or liquid forms. It can be added before or after heat treatment of food products. The amount of the sweetener depends on the purpose of usage. As discussed above, it can be added alone or in combination with other compounds.

EXAMPLES

The following examples illustrate preferred embodiments of the invention for the isolation and purification of Reb D and related compounds and the use thereof in foodstuffs and pharmaceuticals. It will be understood that the invention is not limited to the materials, proportions, conditions and procedures set forth in the examples, which are only illustrative.

Example 1

Purification of Reb D from *Stevia Rebaudiana* Bertoni Plant Leaves

Two kg of *Stevia rebaudiana* Bertoni plant leaves were dried at 45° C. to an 8.0% moisture content and ground to 10-20 mm particles. The content of different glycosides in the leaves was as follows: Stevioside—2.55%, Reb A—7.78%, Reb B—0.01%, Reb C—1.04%, Reb D—0.21%, Reb E—0.02%, Reb F—0.14%, Dulcoside A—0.05%, and Steviolbioside—0.05%. The total content of steviol glycosides was 11.85%. The dried material was loaded into a continuous extractor and the extraction was carried out with 40.0 L of water at a pH of 6.5 at 40° C. for 160 min. The filtrate was collected and subjected to chemical treatment. Calcium oxide in the amount of 400 g was added to the filtrate to adjust the pH within the range of 8.5-9.0, and the mixture was maintained for 15 min with slow agitation. Then, the pH was adjusted to around 3.0 by adding 600 g of $FeCl_3$ and the mixture was maintained for 15 min with slow agitation. A small amount of calcium oxide was further added to adjust the pH to 8.5-9.0 and the mixture was maintained for 30 min with slow agitation. The precipitate was removed by filtration on a plate-and-frame filter press using cotton cloth as the filtration material. The slightly yellow filtrate was passed through the column, packed with cation-exchange resin Amberlite FCP22 ($H^+$) and then, through the column with anion-exchange resin Amberlite FPA53 ($OH^-$). The flow rate in both columns was maintained at $SV=0.8$ $hour^{-1}$. After completion both columns were washed with RO water to recover the steviol glycosides left in the columns and the filtrates were combined. The portion of combined solution containing 120 g total steviol glycosides was passed through seven columns, wherein each column was packed with specific macroporous polymeric adsorbent YWD-03 (Cangzhou Yuanwei, China). The first column with the size of ⅓ of the others acted as a "catcher column". The SV was around 1.0 $hour^{-1}$. After all extract was passed through the columns, the resin sequentially was washed with 1 volume of water, 2 volumes of 0.5% NaOH, 1 volume of water, 2 volumes of 0.5% HCl, and finally with water until the pH was 7.0. The "catcher column" was washed separately. Desorption of the adsorbed steviol glycosides was carried out with 52% ethanol at $SV=1.0$ $hour^{-1}$. Desorption of the first "catcher column" was carried out separately and the filtrate was not mixed with the main solution obtained from other columns. Desorption of the last column also was carried out separately. Eluates from the first to fifth columns were combined and treated separately.

The combined solution of steviol glycosides was mixed with 0.3% of activated carbon from the total volume of solution. The suspension was maintained at 25° C. for 30 min with continuous agitation. Separation of carbon was carried out on a press-filtration system. For additional decolorization the filtrate was passed through the columns packed with cation-exchange resin Amberlite FCP22 ($H^+$) followed with anion-exchange resin Amberlite FPA53 A30B ($OH^-$). The flow rate in both columns was around $SV=0.5$ $hour^{-1}$. The ethanol was distilled using a vacuum evaporator. The solids content in the final solution was around 15%. The concentrate was passed through the columns packed with cation-exchange resin Amberlite FCP22 ($H^+$) and anion-exchange resin Amberlite FPA53 ($OH^-$) with $SV=0.5$ $hour^{-1}$. After all the solution was passed through the columns, both resins were washed with RO water to recover the steviol glycosides left in the columns. The resulting refined extract was transferred to the nano-filtration device, concentrated to around 52% of solids content and spray dried to obtain a highly purified mixture of steviol glycosides. The yield was 100.7 g with 96.8% content of TSG. The mixture contained Stevioside—21.5%, Reb A—65.5%, Reb B—0.1%, Reb C—9.0%, Reb D—0.4%, Reb E—0.5%, Reb F—2.4%, Dulcoside A—0.5%, and Steviolbioside—0.1%.

The combined eluate from the last column, containing 13.3 g of steviol glycosides and around 28.4% Reb D, was deionized and decolorized as discussed above and concentrated to a 33.5% content of total solids.

The concentrate was mixed with two volumes of anhydrous methanol and maintained at 20-22° C. for 24 hours with intensive agitation.

The resulting precipitate was separated by filtration and washed with about two volumes of absolute methanol. The yield of Reb D was 3.9 g with around 86% purity.

For the further purification the precipitate was suspended in three volumes of 60% methanol and treated at 55° C. for 30 min, then cooled down to 20-22° C. and agitated for another 2 hours.

The resulting precipitate was separated by filtration and washed with about two volumes of absolute methanol and subjected to similar treatment with a mixture of methanol and water.

The yield of Reb D was 3.37 g with 99.3% purity.

The purity of the Rebaudioside D was determined using HPLC which was performed using a ZORBAX $NH_2$ column (150×4.6 mm, 5 μm) at a temperature of 30° C. The mobile phase comprised a solution of 20% buffer (0.0125% acetic acid and 0.0125% ammonium acetate) and 80% acetonitrile at a flow rate of 1.0 mL/min. 12 μL of each sample was injected in duplicate and the sample was analyzed using a UV detector at 210 nm (4 nm bandwidth) with a reference of 260 nm (100 nm bandwidth). The analysis required a run time ranging from 40 to 60 min.

A buffer solution of 0.0125% acetic acid and 0.0125% ammonium acetate was prepared by dissolving 0.125 g ammonium acetate and 125 µL glacial acetic acid in one liter of water. The retention time of Rebaudioside B was adjusted by varying the ratio of ammonium acetate to acetic acid while maintaining a total of 0.025% of both combined. Increasing the amount of acetic acid decreased the retention time of Rebaudioside B.

A diluent solution was prepared by mixing 500 mL of ethyl alcohol and 500 mL of the buffer solution. Rebaudioside D standards were prepared by diluting 10.0±0.5 mg (recorded to the nearest 0.1 mg) of the Rebaudioside D standard with 4 mL of the diluent solution to make a standard solution of approximately 2500 mg/L. The Rebaudioside D standard solution was injected at 10.8, 11.4, 12.6 and 13.2 µL. The moisture content was measured by Karl Fischer analysis every time a standard was prepared and corrections were made based on the solvent purity according to the certificate of analysis.

Stevioside standards were prepared by diluting 12.5±0.5 mg (recorded to the nearest 0.1 mg) of the stevioside standard with 5 mL of the diluent solution to make a standard solution of approximately 2500 mg/L standard (stock A) (correcting for moisture and purity). The stevioside standard was then diluted using one mL of stock A to ten mL of diluent to produce a 250 mg/L standard (stock B), and stock standards were diluted to final concentrations ranging from 2.5 to 50 mg/L.

Samples of the Rebaudioside D compositions were prepared by diluting 125±2 mg (recorded to the nearest 0.1 mg) of the Rebaudioside D composition with 50 mL of the diluent solution to make a sample solution of approximately 2500 mg/L (correcting for moisture). Individually prepared duplicate samples were injected at 12 µL. If the samples were not analyzed immediately, they were stored without headspace, under nitrogen, and desiccated.

The TABLE 66 provides a guideline for retention times for Rebaudioside D and other steviol glycosides. However, those of ordinary skill in the art should appreciate that the retention times may be modified as needed.

TABLE 66

| Compound | HPLC retention time, min |
| --- | --- |
| Stevioside | 5.4 |
| Rebaudioside A | 7.8 |
| Rebaudioside B | 28.6 |
| Rebaudioside C | 6.0 |
| Rebaudioside D | 15.7 |
| Rebaudioside E | 10.7 |
| Rebaudioside F | 6.4 |
| Steviolbioside | 17.7 |
| Dulcoside A | 4.5 |
| Rubusoside | 3.0 |

Example 2

Purification of Reb D and Reb A from *Stevia* Extract

One kg of *Stevia* extract containing Stevioside—22.63%, Reb A—52.46%, Reb C—7.52%, Reb D—1.18%, Reb B—0.55%, Reb E—0.64%, Reb F—1.79%, Steviolbioside—0.1%, and Dulcoside A—1.59%, with 88.46% of total steviol glycosides content, was dissolved in 3000 mL of 95% ethyl alcohol and maintained at 80° C. for 35 min, and then at 15° C. for 12 hours with agitation. When the temperature reached 22° C., 1.0% of highly purified Reb A was added to the reaction mixture as a starter to initiate crystallization.

Precipitate was separated by filtration and washed with about two volumes of 99.5% ethanol.

The yield of crystalline material was 47.1% with content of 81.7% and 3.3% of Reb A and Reb D respectively.

The precipitate was mixed with 5 volumes of 78% ethanol and incubated at 50° C. for 3 hours with agitation. Then, the mixture was cooled down to room temperature and the precipitate with 21.4% Reb D content was separated by filtration.

The remaining solution after isolation of Reb D was mixed with 1% Reb A as starter and left for crystallization at 22° C. for 12 hours. The crystals were separated by filtration and washed with about two volumes of ethanol. Reb A content in the crystals was 98.8%.

For further purification the high RebD precipitate was suspended in 50% ethanol at 1:2 wt/vol. ratio, and maintained for 12 hours at 35° C. with agitation. The suspension was filtered and precipitate was dried. The yield of precipitate with 21.7% of Reb A and 81.6% of Reb D contents was 35.5% from initial material. The precipitate was subjected to similar treatment to get a product with 3.7% of Reb A and 95.7% of Reb D content. The yield of this product was 58.5%.

The obtained Reb D was dissolved in 2 volumes of 30% methanol and treated with 0.3% of activated carbon at 60° C. for 30 min then subjected to hot filtration. Reb D spontaneously precipitated after filtration.

Highly purified Reb D (98.4%) was separated by filtration and dried at 80° C. for 12 hours.

Example 3

Purification of Reb D and Reb A from *Stevia* Extract

One kg of *Stevia* extract containing Stevioside—22.63%, Reb A—52.46%, Reb C—7.52%, Reb D—1.18%, Reb B—0.55%, Reb E—0.64%, Reb F—1.79%, Steviolbioside—0.1%, and Dulcoside A—1.59%, with 88.46% of total steviol glycosides content, was dissolved in 3000 mL of 88% ethyl alcohol and maintained at 55° C. for 15 min, and then at 22° C. for 24 hours with agitation. When the temperature reached 22° C., 1.0% of highly purified Reb A was added to the mixture as a starter to initiate crystallization. The precipitate was separated by filtration and washed with about two volumes of 99.5% ethanol.

The yield of crystalline material was 33.0% with content of 95.6% and 3.5% of Reb A and Reb D respectively.

The precipitate was mixed with 3.0 volumes of anhydrous methanol and incubated at 22° C. for 90 minutes, and the precipitate with content of 98.9% Reb A was separated by filtration, washed with about two volumes of anhydrous methanol and dried at 80° C. for 12 hours. The yield of the product from the initial extract was 29.3%.

Methanol was removed by vacuum evaporation and the liquid was concentrated to 33.5% solids.

The obtained syrup with 28.3% Reb D content was mixed with two volumes (vol/vol.) of methanol, and 1% of pure Reb D was added to start the crystallization process. The mixture was maintained at 22° C. for 24 hours with agitation.

The precipitate was separated by filtration and washed with about two volumes of anhydrous methanol and dried. The yield of the product was 10.4 g with 84.5% content of Reb D.

To achieve further purification, the precipitate was suspended in 60% methanol at 1:3, wt/vol. ratio, and maintained at 55° C. for 15 minutes, then cooled down to 22° C. and agitated for another 1.5 hours. The suspension was filtered. The precipitate was washed with about two volumes of anhydrous methanol and dried at 80° C. for about 12 hours.

The yield of precipitate with 99.1% of Reb D content was 9.0 g.

Example 4

Purification of Reb D from Remaining Solution After Isolation of Reb A

One kg of *Stevia* extract containing Stevioside—24.3%, Reb A—62.1%, Reb C—8.8%, Reb D—1.6%, Reb B—0.2%, Reb E—0.6%, Reb F—1.0%, Steviolbioside—0.10%, and Dulcoside A—1.3%, with 87.9% of total steviol glycosides content, was dissolved in 3000 mL of 85% methyl alcohol and maintained at 55° C. for 15 min, and then at 22° C. for 1.5 hours with agitation. When the temperature reached 22° C., 1.0% of highly purified Reb A was added to the reaction mixture as a starter to initiate crystallization.

The precipitate was separated by filtration and washed with about two volumes of anhydrous 99.5% methanol.

The yield of crystalline material was 42.5% with content of 98.5% and 0.3% of Reb A and Reb D respectively.

The combined total filtrate containing Stevioside (49.6%), Reb C (17.5%), Reb A (29.9%) and Reb D (3.0%) as the main substances was evaporated in order to remove methanol and concentrated up to a total solids content of about 10.0%.

The remaining solution, containing 115 g of total solids after isolation of Reb A, was passed through a series of eight columns with the rate equal to 1.0 bed volume (BV) per 1 hour. Each column was packed with 150 mL of specific polar macroporous polymeric resin. Upon completion of the adsorption the resin was washed with 5 volumes of water and desorption of the adsorbed steviol glycosides was carried out with 50-52% ethanol at BV=1.0-2.0 hour$^{-1}$.

Eluates from the last two columns, containing around 80% of total quantity of Reb D, were collected separately. Ethanol was removed by evaporation under vacuum and dried.

The operation was repeated several times to complete treatment of all remaining solution.

The average concentration and total quantity of Reb D was 21.4% and 10.1 g respectively.

For the sake of further purification, the material was suspended in 60% methanol at 1:3 wt/vol. ratio, and maintained at 55° C. for 15 minutes, cooled down to 22° C. and agitated for another 1.5 hours. The suspension was filtered; the precipitate was washed with about two volumes of anhydrous methanol.

The operation was repeated two times and the final product was dried at 80° C. for about 12 hours.

The yield of precipitate with 98.6% of Reb D contents was 9.4 g.

The remaining solution after isolation of Reb A and Reb D contained a mixture of steviol glycosides with a TSG content of 96.7%.

Example 5

Purification of Reb D from Remaining Solution After Isolation of Reb A

One kg of *Stevia* extract containing Stevioside (32.3%), Reb A (52.6%), Reb C (9.6%), Reb D (2.3%), Reb B (0.1%), Reb E (0.6%), Reb F (1.6%), Steviolbioside (0.1%), and Dulcoside A (0.8%) on a dry basis, with 86.3% of total steviol glycosides content, was dissolved in 3000 mL of 99.5% ethyl alcohol and maintained at 80° C. for about 10 min. During the heating crude Reb A was precipitated. The suspension was cooled down to 22° C. and maintained for 10 hours with agitation. The precipitate was separated by filtration and washed with 600 mL of 99.5% ethanol.

The obtained white precipitate contained Stevioside (7.55%), Reb A (79.87%), Reb C (7.76%), Reb D (1.55%), Reb B (0.14%), Reb E (0.41%), Reb F (2.25%), Steviolbioside (0.12%), and Dulcoside A (0.35%) on a dry basis. The total steviol glycosides content was 99.5%. The yield of the product was 56.4% from the initial extract.

The filtrate and washed liquid were combined and spray dried. The product contained Stevioside (64.32%), Reb A (17.32%), Reb C (11.98%), Reb D (3.27%), Reb B (0.05%), Reb E (0.85%), Reb F (0.76%), Steviolbioside (0.07%), and Dulcoside A (1.38%) on a dry basis. Around 436 g was obtained and it was named as RS-1.

The wet cake of crude Reb A was suspended in 2.3 volumes (wt/vol.) of 80.5% ethanol and completely dissolved by heating at 80° C. for about 30 min with continuous agitation. The solution was cooled to 20° C. and pure Reb A was added in the amount of 1.0% from solids. The cooling was continued to 15° C. and maintained for 12 hours with slow agitation. Then 1.0 volume (vol/wt) of 99.5% ethanol to the initial solids was added to the crystallization mixture and the suspension was maintained at the same temperature for another 12 hours.

The precipitate was separated by filtration and washed with about 850 mL of 99.5% ethanol. The obtained white precipitate contained Stevioside (1.1%), Reb A (95.3%), Reb C (1.3%), Reb D (1.28%), Reb B (0.10%), Reb E (0.32%), Reb F (0.4%), Steviolbioside (0.10%), and Dulcoside A (0.1%) on a dry basis. The yield of the product was 66.4% (374 g) from the initial solids at the first stage.

The filtrate and washing liquid were combined and spray dried. The product contained Stevioside (20.25%), Reb A (49.49%), Reb C (20.48%), Reb D (2.08%), Reb B (0.22%), Reb E (0.59%), Reb F (5.89%), Steviolbioside (0.16%), and Dulcoside A (0.84%) on a dry basis. The yield was 190 g and it was named as RS-2.

The further purification of the obtained product was carried out similarly to the second step described above with the application of 3.5 volumes (vol/wt) of 77.7% ethanol as the crystallization medium.

The crystals were separated and dried in a vacuum oven at 80° C. for 12-14 hours under reduced pressure. The product contained Stevioside (<0.1%), Reb A (98.71%), Reb C (<0.1%), Reb D (0.72%), Reb B (<0.10%), Reb E (0.12%), and Reb F (0.15%) on a dry basis. The yield of the product was 75.4% from the initial solids at the first stage. 282.0 g of product was obtained.

The spray dried mother liquor contained Stevioside (4.17%), Reb A (84.85%), Reb C (4.98%), Reb D (3.00%), Reb B (0.10%), Reb E (0.93%), Reb F (1.17%), Steviolbioside (0.41%), and Dulcoside A (0.41%) on a dry basis. The yield of the product was 92 g and it was named as RS-3.

Isolation and purification of Reb D from RS-1 was carried out similarly to the procedure described in EXAMPLE 4 for remaining solution. 145 g of the material was dissolved in 580 mL of water and the resulted 20% solution was passed through the series of ten columns with the rate equal to 1.0 bed volume (BV) per 1 hour. Each column was packed with 150 mL of specific polar macroporous polymeric resin. Upon completion of the adsorption the resin was washed with 5 volume of water and desorption of the adsorbed steviol glycosides was carried out with 50-52% ethanol at $BV=1.0$-$2.0$ hour$^{-1}$.

Eluates from the last two columns, containing around 80% of the total quantity of Reb D, were collected separately. The combined solution was mixed with 0.3% activated carbon from the total volume of solution. The suspension was maintained at 25° C. for 30 min with continuous agitation and carbon was separated by filtration.

The filtrate was evaporated and dried under vacuum.

The operation was repeated three times to complete the treatment of all RS-1.

The average concentration and total quantity of Reb D was 31.6% and 11.5 g respectively.

The resulting material was suspended in 60% methanol at 1:3 wt/vol. ratio, and maintained at 55° C. for 15 minutes, then cooled down to 22° C. and agitated for another 1.5 hours. The suspension was filtered and the precipitate was washed with about two volumes of anhydrous methanol.

The operation was repeated two times and the final product was dried at 80° C. for about 12 hours.

The yield of precipitate with 98.8% of Reb D contents was 9.2 g.

For the purpose of further retreatment, RS-2 was recycled to the first stage of enrichment with Reb A.

Isolation and purification of Reb D from RS-3 was similar to the procedure described in EXAMPLE 3.

The yield of Reb D was 1.8 g with 99.1% purity.
The yield of Reb A was 65.7 g with 98.5% purity.

Example 6

Purification of Reb D from Remaining Solution After Isolation of Reb A

A wet cake of crude Rebaudioside A and RS-1 was prepared in a manner similar to that described in EXAMPLE 5.

The wet cake of crude Reb A was suspended in 2.65 volumes (wt/vol.) of 75.0% ethanol and completely dissolved by heating at 80° C. for about 30 min with continuous agitation. The solution was cooled to 20° C. and pure Reb A was added in the amount of 1.0% from solids. The cooling was continued to 15° C. and maintained for 12 hours with slow agitation. Then 0.8 volume (vol/wt) of 99.5% ethanol to the initial solids was added to the crystallization mixture and the suspension was maintained at the same temperature for another 12 hours.

The precipitate was separated by filtration and washed with about 550 mL of 99.5% ethanol. The product contained Stevioside (0.41%), Reb A (98.05%), Reb C (0.22%), Reb D (0.61%), Reb B (0.11%), Reb E (0.24%), Reb F (0.26%), and Dulcoside A (0.10%) on a dry basis. The yield of the product was 369 g or 65.4% from the initial solids.

The filtrate was spray dried to make RS-2 which contained Stevioside (21.05%), Reb A (45.51%), Reb C (22.01%), Reb D (3.33%), Reb B (0.20%), Reb E (0.73%), Reb F (6.00%), Steviolbioside (0.35%), and Dulcoside A (0.82%) on a dry basis. The yield of product was 195 g. The product was recycled to the first stage of the Reb A isolation process.

The isolation and purification of Reb D from RS-1 was carried out in a method similar to that described in EXAMPLE 5.

The yield of precipitate with 99.1% of Reb D contents was 8.9 g.

Example 7

Purification of Reb D from Remaining Solution After Isolation of Reb A

One kg of Stevia extract containing Stevioside (37.1%), Reb A (48.2%), Reb C (10.2%), Reb D (0.9%), Reb B (0.1%), Reb E (0.8%), Reb F (1.1%), Steviolbioside (0.1%), and Dulcoside A (1.5%) on a dry basis, with 90.5% of total steviol glycosides content, was dissolved in 3000 mL of 99.5% ethyl alcohol and maintained at 80° C. for about 10 min. During the heating crude Reb A precipitated. The suspension was cooled down to 22° C. and maintained for 10 hours with agitation. The precipitate was separated by filtration and washed with 600 mL of 99.5% ethanol.

The obtained white precipitate contained Stevioside (9.06%), Reb A (78.89%), Reb C (9.42%), Reb D (0.61%), Reb B (0.1%), Reb E (0.60%), Reb F (0.95%), Steviolbioside (0.1%), and Dulcoside A (0.27%) on a dry basis. Total steviol glycosides content was 98.4%. The yield of the product was 53.7% from initial extract.

The filtrate and washing liquid were combined and spray dried (463 g). The product contained Stevioside (69.62%), Reb A (12.60%), Reb C (11.10%), Reb D (1.24%), Reb B (0.10%), Reb E (1.03%), Reb F (1.27%), Steviolbioside (0.10%), and Dulcoside A (2.94%) on a dry basis. 463 g of product (RS-1) was obtained.

The wet cake of crude Reb A was suspended in 3.0 volumes (wt/vol.) of 81.0% ethanol. After homogeneous suspension was obtained the temperature was increased to 40° C. and maintained for 12 hours. Then, the suspension was cooled down to 22° C., 0.5 volumes (vol/wt) of 99.5% ethanol was added, and the suspension was maintained for another 12 hours with continuous agitation.

The precipitate was separated by filtration and washed with about 600 mL of 99.5% ethanol. The product contained Stevioside (0.18%), Reb A (98.32%), Reb C (0.20%), Reb D (0.51%), Reb B (0.1%), Reb E (0.28%), Reb F (0.31%), and Dulcoside A (0.1%) on a dry basis. The yield of the product was 54.7% from the initial solids at the first stage. 349.0 g of highly purified Reb A was obtained with 34.9% output from initial extract.

The spray dried mother liquor contained Stevioside (25.54%), Reb A (42.82%), Reb C (26.54%), Reb D (0.80%), Reb B (0.10%), Reb E (1.19%), Reb F (2.14%), Steviolbioside (0.29%), and Dulcoside A (0.59%) on a dry basis. 188 g of product was obtained, and was recycled to the first stage of the initial isolation process of Reb A.

Isolation and purification of Reb D from RS-1 was carried out using a method similar to that described in EXAMPLE 5.

The yield of precipitate with 98.7% of Reb D contents was 3.5 g.

Example 8

Purification of Reb D from Remaining Solution After Isolation of Reb A

One kg of *Stevia* extract containing Stevioside (22.63%), Reb A (52.46%), Reb C (7.52%), Reb D (1.18%), Reb B (0.55%), Reb E (0.64%), Reb F (1.79%), Steviolbioside (0.1%), and Dulcoside A (1.59%) on a dry basis, with 88.46% of total steviol glycosides content, was dissolved in 3500 mL of 85.0% ethyl alcohol at 55° C. for about 15 min. The temperature of the solution was adjusted to 40° C. and maintained for 12 hours, and then at 22° C. for another 12 hours with continuous agitation. When the temperature reached 22° C., 1 vol. % of highly purified Reb A was added to the reaction mixture as a starter to initiate crystallization. Then, 0.8 volumes (vol/wt) of 99.5% ethanol to the initial solids, was added to the reaction mixture and the process was continued for another 12 hours. The precipitate was separated by filtration and washed with 1000 mL of 99.5% ethanol.

The product contained Stevioside (0.31%), Reb A (98.2%), Reb C (0.26%), Reb D (0.3%), Reb B (0.05%), Reb E (0.23%), Reb F (0.55%), and Dulcoside A (0.1%) on a dry basis. The yield of the product was 42.0% from the initial extract.

The spray dried mother liquor contained Stevioside (38.79%), Reb A (19.34%), Reb C (12.78%), Reb D (1.82%), Reb B (0.91%), Reb E (0.94%), Reb F (2.69%), Steviolbioside (0.17%), and Dulcoside A (2.67%) with 80.1% of total steviol glycosides content on a dry basis. The yield of the product was 580 g.

Isolation and purification of Reb D from RS-1 was carried out using a method similar to that described in EXAMPLE 5.

The yield of precipitate with 98.9% of Reb D contents was 7.1 g.

Example 9

Purification of Reb D from Remaining Solution After Isolation of Reb A and Steviol Glycosides One kg of spray dried remaining solution (RS-1) obtained after isolation of Reb A as per the scheme described in EXAMPLE 6, containing Stevioside (64.32%), Reb A (17.32%), Reb C (11.98%), Reb D (3.27%), Reb B (0.05%), Reb E (0.85%), Reb F (0.76%), Steviolbioside (0.07%), and Dulcoside A (1.38%) on a dry basis and with 82.3% total steviol glycosides content, was dissolved in 3000 mL of absolute methyl alcohol and maintained at 75° C. for about 10 min. During the heating, crude Stevioside precipitated. The suspension was cooled down to 25° C. and maintained for 10 hours with agitation. The precipitate was separated by filtration and washed with 900 mL of absolute methanol.

The yield of crystals containing Stevioside (93.2%), Reb A (3.6%), Reb C (2.1%), Reb D (0.2%), Reb B (0.05%), Reb E (0.2%), Reb F (0.2%), Steviolbioside (0.1%), and Dulcoside A (0.35%) was 53.3% from initial material, and the total steviol glycoside content was 97.7% on a dry basis.

The filtrate and washing liquid were combined and spray dried. The content of steviol glycosides was as follows: Stevioside (31.36%), Reb A (32.98%), Reb C (23.26%), Reb D (6.77%), Reb B (0.05%), Reb E (1.59%), Reb F (1.40%), Steviolbioside (0.04%), and Dulcoside A (2.56%). The yield of the product was around 467 g.

The isolation and purification of Reb D from the spray dried remaining solution was carried out using a method similar to that described in EXAMPLE 5.

The yield of precipitate with 98.9% of Reb D contents was 20.5 g.

Example 10

Purification of Reb D from Remaining Solution After Isolation of Reb A and Steviol Glycosides One kg of *Stevia* extract containing Stevioside—24.3%, Reb A—62.1%, Reb C—8.8%, Reb D—1.6%, Reb B—0.2%, Reb E—0.6%, Reb F—1.0%, Steviolbioside—0.10%, and Dulcoside A—1.3%, with 87.9% of total steviol glycosides content was dissolved in 3000 mL of 85% methyl alcohol and maintained at 55° C. for 15 min, and then at 22° C. for 1.5 hours with agitation. When the temperature reached 22° C., 1.0% of highly purified Reb A was added to the reaction mixture as a starter to initiate crystallization.

The precipitate was separated by filtration and washed with about two volumes of anhydrous 99.5% methanol.

The yield of crystalline material was 42.5% including Stevioside (0.3%), Reb A (98.5%), Reb C (0.4%), Reb D (0.3%), Reb B (0.1%), Reb E (0.1%), Reb F (0.1%), Steviolbioside (0.1%), and Dulcoside A (0.1%).

The combined total filtrate containing Stevioside (42.0%), Reb A (35.2%), Reb C (15.0%), Reb D (2.6%), Reb B (0.3%), Reb E (1.0%), Reb F (1.7%), Steviolbioside (0.1%), and Dulcoside A (2.2%) was agitated for another 12 hours at 22° C. after adding 2 g of high purity Stevioside for the initiation of crystallization.

The yield of crystals containing Stevioside (92.6%), Reb A (3.9%), Reb C (2.4%), Reb D (0.1%), Reb B (0.1%), Reb E (0.3%), Reb F (0.2%), Steviolbioside (0.1%), and Dulcoside A (0.3%) was 48.0% from initial material, and the content of total steviol glycosides was 97.3% on a dry basis.

The filtrate and washing liquid were combined and spray dried. The content of steviol glycosides was as follows: Stevioside (3.8%), Reb A (56.3%), Reb C (25.9%), Reb D (4.8%), Reb B (0.4%), Reb E (1.6%), Reb F (3.0%), Steviolbioside (0.1%), and Dulcoside A (4.0%). The yield of the product was around 299 g.

The isolation and purification of Reb D from the spray dried remaining solution was carried out using a method similar to that described in EXAMPLE 5.

The yield of precipitate with 99.3% of Reb D contents was 9.4 g.

Example 11

Purified Steviol Glycoside Mixture from *Stevia Rebaudiana* Bertoni Plant Leaves 2.5 kg of *Stevia rebaudiana* Bertoni dried plant leaves containing Stevioside—2.6%, Reb A—6.9%, Reb B—0.01%, Reb C—1.1%, Reb D—0.05%, Reb E—0.03%, Reb F—0.3%, Dulcoside A—0.2%, Rubusoside 0.1% and Steviolbioside—0.01% were extracted with 50.0 L of water at a pH of 6.5 at 40° C. for 160 min. The biomass was separated by filtration, 500 g calcium oxide was added to the filtrate to adjust the pH within the range of 8.5-9.0, and the mixture was maintained for 15 min with slow agitation. The pH was then adjusted to around 3.0 by adding 750 g of $FeCl_3$, and the mixture was maintained for 15 min with slow agitation. A small amount of calcium oxide was further added to adjust the pH to 8.5-9.0 and the mixture was maintained for 30 min with slow agitation. The precipitate was removed by filtration and the filtrate was passed through 4 columns, each packed with 1.5 liters of specific macroporous polymeric adsorbent YWD-03 (Cangzhou Yuanwei, China) at BV 1.0 hour$^{-1}$. Further, the resin sequentially was washed with 1 volume of water, 2 volumes of 0.5% NaOH, 1 volume of water, 2 volumes of 0.5% HCl, and finally with water until the pH was 7.0. Desorption of the adsorbed steviol glycosides was carried out with 52% ethanol at SV=1.0 hour$^{-1}$. Desorption of the last column was carried out separately, and the filtrate was not mixed with the main solution obtained from the other columns. First 20 L of eluate from the first three columns was collected and mixed with 0.3% of activated carbon from the total volume of solution. The suspension was maintained at 25° C. for 30 min with continuous agitation. Separation of carbon was carried out on a press-filtration system. The obtained filtrate was passed through the columns packed with cation-exchange resin Amberlite FCP22 (H$^+$) followed with anion-exchange resin Amberlite FPA53 A30B (OH$^-$). The flow rate in both columns was around SV=0.5 hour-1. The ethanol was distilled using a vacuum evaporator. The solids content in the final solution was around 15%. The concentrate was passed through the columns packed with 200 mL of LX-18 macroporous adsorbent resin (Xi'an SunResin Technology Ltd., China). A solution was obtained after the column was passed through cation-exchange resin Amberlite FCP22 (H$^+$) and anion-exchange resin Amberlite FPA53 (OH$^-$) with SV=0.5 hour$^{-1}$. The resulting solution was concentrated by a nano-filtration device to around 50% of solids content, and spray dried to obtain a highly purified mixture of steviol glycosides. The yield was 150.1 g with 97.5% TSG content, comprising Stevioside—22.4%, Reb A—60.0%, Reb B—0.1%, Reb C—9.1%, Reb D—0.4%, Reb E—0.3%, Reb F—2.6%, Dulcoside A—1.5%, Rubusoside 1.0% and Steviolbioside—0.1%.

Example 12

Purified Steviol Glycoside Mixture from Low Purity Steviol Glycoside Mixture

Six kg of steviol glycoside mixture with a TSG content of 85.29% (w/w on a dry basis), comprising 0.16% Rubusoside, 0.68% Dulcoside A, 26.20% Stevioside, 9.78% Rebaudioside C, 1.86% Rebaudioside F, 45.92% Rebaudioside A, 0.51% Rebaudioside D, 0.09% Steviolbioside, and 0.09% Rebaudioside B, was dissolved in 114 L of water.

The solution was passed through 6 consecutively connected columns, each packed with 20 L of YWD-03 (Cangzhou Yuanwei, China) macroporous resin at 1.0 BV per hour.

The columns were then washed consecutively with 200 liters of water, 120 liters of 0.5% NaOH, 200 liters of water, 120 liters of 0.5% HCl, 360 liters of water, and 120 liters of 10% aqueous ethanol.

The columns from the second column through the fifth column were disconnected and the adsorbed steviol glycosides were eluted with 40 liters of 50% aqueous ethanol. The obtained solution was evaporated, concentrated and spray dried to yield 2.5 kg purified steviol glycoside mixture with a TSG content of 98.56% (w/w on a dry basis) comprising 0.18% Rubusoside, 0.78% Dulcoside A, 30.31% Stevioside, 11.31% Rebaudioside C, 2.15% Rebaudioside F, 53.04% Rebaudioside A, 0.59% Rebaudioside D, 0.10% Steviolbioside, and 0.10% Rebaudioside B.

Example 13

Low-Calorie Orange Juice Drink with Reb D 60 g of concentrated orange juice were mixed with 1.1 g of citric acid, 0.24 g of vitamin C, 1.0 g of orange essence, 0.76 g of Reb D and water, to create a homogeneously dissolved mixture of 1000 mL, in total amount. Then, the mixture was sterilized for a period of 20 seconds at about 95° C. in order to prepare an orange juice similar to one made by conventional methods. The product had an excellent taste profile.

Juices from other fruits, such as apple, lemon, apricot, cherry, pineapple, etc. can be prepared using the same approach.

Example 14

Low-Calorie Carbonated Lemon-Flavored Beverage with Reb D

Sugar (30.0 kg), citric acid (2.5 kg), green tea extract (25.0 kg), salt (0.3 kg), lemon tincture (10.0 L), juniper tincture (8.0 L), sodium benzoate (0.17 kg) and Reb D (0.4 kg) were mixed well and dissolved in carbonated water making 1000 L of a mixture.

Example 15

Low-Calorie Carbonated Drink with Reb D

The formula for the beverage is provided in TABLE 67.

TABLE 67

| Ingredients | Quantity, % |
| --- | --- |
| Cola flavor | 0.340 |
| Phosphoric acid (85%) | 0.100 |
| Sodium citrate | 0.310 |
| Sodium benzoate | 0.018 |
| Citric acid | 0.018 |
| Sweetener | 0.030 |
| Carbonated water | to 100 |

Example 16

Chocolate with Reb D

A composition containing 30 kg of cacao liquor, 11.5 kg of cacao butter, 14 kg of milk powder, 44 kg of sorbitol, 0.1 kg of salt, and 0.1 kg of high purity Reb D was kneaded sufficiently, and the mixture was then placed in a refiner to reduce its particle size for 24 hours. Thereafter, the content was transferred into a conche, 300 grams of lecithin was added, and the composition was kneaded at 50° C. for 48 hours. Then, the content was placed in a shaping apparatus, and solidified.

The product is a low-cariogenic and low-calorie chocolate, with excellent texture and sensory characteristics.

Example 17

Ice Cream with Reb D 1.50 kg of whole milk was heated to 45° C., and 300 grams of milk cream, 100 grams of tagatose, 90 grams of sorbitol, 6 grams of carrageenan as a stabilizer, 3 grams of polysorbate-80 as an emulsifier, and 1.0 gram of Reb D as in EXAMPLE 10, were added into the milk and stirred until the ingredients completely dissolved. The mixture then was pasteurized at a temperature of 80° C. for 25 seconds. The homogenization of the obtained mixture was carried out at a pressure of 800 bars and the samples were kept at a temperature of 4° C. for 24 hours to complete the aging process. Vanilla flavor (1.0% of the mixture weight) and coloring (0.025% of the mixture weight) were added into the mixture after aging. The mixture was then transferred to an ice cream maker to produce ice cream automatically. Samples of produced ice creams were transferred to sealed containers and were kept in the freezer at a temperature of −18° C.

The application of sweeteners does not affect the physicochemical properties of ice cream, as well as the overall attributes of color, smoothness, surface texture, air cell, vanilla aroma intensity, vanilla taste, chalkiness, iciness and melting rate.

Example 18

Yoghurt with Reb D

In 5 kg of defatted milk, 4.0 grams of high purity Reb D prepared according to the invention was dissolved. After pasteurizing at 82° C. for 20 minutes, the milk was cooled to 40° C. A starter in the amount of 150 grams was added and the mixture was incubated at 37° C. for 6 hours. Then, the fermented mass was maintained at 10-15° C. for 12 hours.

The product is a low-calorie and low-cariogenic yoghurt, without foreign taste and odor.

Example 19

Tabletop Tablets with Reb D

A mixture, consisting of 58.5% lactose, 10% calcium silicate, 5% cross-carmellose, 5% L-leucine, 1% aerosil 200, 0.5% magnesium stearate, and 20% of high purity Reb D, obtained according to the invention from initial *Stevia* extract or remaining solution after isolation of Reb A and steviol glycosides, was kneaded sufficiently. Then the mixture was shaped with the use of a tabletting machine, equipped with punches of 6.2 mm diameter, into tablets of 70 mg each, 3.0 mm thick, and 10±1 kg hardness.

The tablets can be easily administered due to their favorable sweetness and fast solubility.

Example 20

Iced Lemon Tea Sweetened with Reb D

The formula for the beverage is provided in TABLE 68.

TABLE 68

| Ingredients | Quantity, % |
| --- | --- |
| High purity Reb D | 0.08 |
| Sodium benzoate | 0.02 |
| Citric acid | 0.27 |
| Ascorbic acid | 0.01 |
| Tea extract | 0.03 |
| Lemon flavor | 0.10 |
| Water | to 100 |

All ingredients were blended and dissolved in the water, and pasteurized. The product possessed excellent taste and flavor.

Example 21

Bread with Reb D 1 kg of flour, 37.38 grams of fructooligosaccharide syrup, 80 grams of margarine, 20 grams of salt, 20 grams of yeast, and 0.25 grams of high purity Reb D obtained according to the invention were placed into the blender and mixed well. 600 mL of water was poured into the mixture and kneaded sufficiently. At the completion of the kneading process, the dough was shaped and raised for 30 to 45 minutes. The raised dough was placed in an oven and baked for 45 minutes. Bread samples had a creamy white color and smooth texture.

Example 22

Diet Cookie with Reb D

Flour, 50.0%; margarine, 30.0%; fructose, 10.0%; maltitol, 8.0%; whole milk, 1.0%; salt, 0.2%; baking powder, 0.15%; vanillin, 0.1%; and Reb D, 0.55%, obtained according to this invention, were kneaded well in a dough-mixing machine. After molding of the dough the cookies were baked at 200° C. for 15 minutes.

The product is a low-calorie diet cookie with excellent properties and appropriate sweetness.

Example 23

Cake with Reb D 123 g of hen eggs, 45 g of sugar, 345 g of sorbitol liquid, 2.0 g of sucrose fatty acid ester, and 0.35 g of Reb D were mixed with 100 g of wheat flour and with 200 g of water in order to prepare a cake according to a common method. The product had an excellent taste with an optimal sweet flavor.

Example 24

Marshmallow with Reb D 100 g of egg whites were mixed with 280 g of sugar and after foaming was induced, the product was mixed with 480 g of gelatin and 144 g of water to create a homogeneous gelatin solution. Next, 126 g of 70% sorbitol liquid was added, as well as 1.7 g of Reb D and a small essence amount so that 1.13 kg of marshmallow was manufactured according to a conventional method. The product had an excellent taste with a sweet flavor.

Example 25

Soy Sauce with Reb D 0.8 g of Reb D was added to 1000 mL of soy sauce and mixed homogenously. The product had an excellent taste as well as a stable product quality.

Example 26

Tooth Paste with Reb D

A tooth paste was prepared by kneading a composition comprising calcium phosphate, 45.0%; carboxymethylcellulose, 1.5%; carrageenan, 0.5%; Glycerol, 18.0%; polyoxyethylene sorbitan mono-ester, 2.0%; beta-cyclodextrin, 1.5%; sodium laurylsarcosinate, 0.2%; flavoring, 1.0%; preservative, 0.1%; Reb D, obtained according to this invention, 0.2%; and water to 100%, in a conventional manner. The product possessed excellent foaming and cleaning abilities with excellent sweetness.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim:

1. A method for purifying steviol glycosides, comprising the steps of:
   a. providing a biomass of a *Stevia rebaudiana* plant;
   b. extracting steviol glycosides from the biomass by contacting the biomass with water, thereby producing an extract solution comprising steviol glycosides;
   c. providing a plurality of consecutively connected columns packed with a macroporous adsorbent resin capable of adsorbing steviol glycosides to create a multi-column system;
   d. passing the solution comprising steviol glycosides through the multi-column system to obtain at least two columns, each column having a different ratio of adsorbed steviol glycosides;
   e. removing impurities by washing the multi-column system with a washing solution; and
   f. eluting the adsorbed steviol glycosides from at least one column in the multi-column system with ethanol, to obtain an eluted solution comprising steviol glycosides.

2. The method of claim 1, wherein the washing solution comprises an aqueous alcohol solution having a water to alcohol ratio ranging from about 99.9:0.1 to about 60:40.

3. The method of claim 1, wherein the adsorbed steviol glycosides are eluted with an aqueous solution comprising water and ethanol and having a water to ethanol ratio ranging from about 60:40 to about 0.1:99.9.

4. The method of claim 1, wherein 3 to 15 columns are consecutively connected in series.

5. The method of claim 1, wherein a ratio of a volume of a first column of the plurality of columns to a volume of a second column of the plurality of columns is in the range of about 1:1 to about 1:10.

6. The method of claim 1, wherein a ratio of a volume of a last column of the plurality of columns to a volume of a penultimate column of the plurality of columns is in the range of about 3:1 to about 1:10.

7. The method of claim 1, further comprising eluting high Rebaudioside D fractions from the multi-column system to obtain an eluted Rebaudioside D solution.

* * * * *